(12) United States Patent
Zhou et al.

(10) Patent No.: US 6,465,656 B2
(45) Date of Patent: Oct. 15, 2002

(54) SYNTHESIS OF 1,3,5-TRISUBSTITUTED PYRAZOLES

(75) Inventors: Jiacheng Zhou, Hockessin, DE (US); Lynette May Oh, West Chester, PA (US); Pasquale N. Confalone, Greenville; Hui-Yin Li, Hockessin, both of DE (US); Philip Ma, West Chester, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/005,938

(22) Filed: Dec. 3, 2001

(65) Prior Publication Data

US 2002/0055641 A1 May 9, 2002

Related U.S. Application Data

(62) Division of application No. 09/685,127, filed on Oct. 10, 2000, now Pat. No. 6,329,527.
(60) Provisional application No. 60/161,666, filed on Oct. 21, 1999.

(51) Int. Cl.[7] ..................... C07D 261/20; C07D 231/04
(52) U.S. Cl. ..................................... 548/241; 541/369.7
(58) Field of Search ............................... 548/241, 369.7

(56) References Cited

FOREIGN PATENT DOCUMENTS

| WO | WO 98/57951 | 12/1998 |
|----|-------------|---------|
| WO | WO 98/28269 | 7/1999 |
| WO | WO 99/32454 | 7/1999 |
| WO | WO 99/50255 | * 10/1999 |

OTHER PUBLICATIONS

Tanaka, Kiyoshi et al: "Preparation of trifluoracetonitrile phenylimine and its reactions with some dipolarophiles" Chem. Lett. (1992), (4), 543–6, XP000973662 (the whole document).

* cited by examiner

*Primary Examiner*—T A Solola
*Assistant Examiner*—Joseph Murray
(74) *Attorney, Agent, or Firm*—David H. Vance

(57) ABSTRACT

A novel process for making 1,3,5-trisubstituted pyrazoles of the type shown below from appropriate phenyl hydrazines is described.

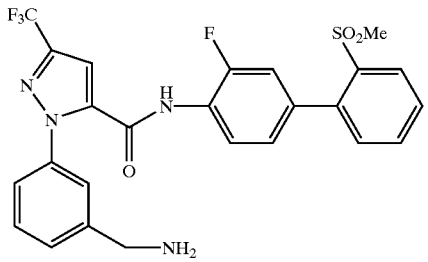

These compounds are useful as factor Xa inhibitors.

20 Claims, No Drawings

SYNTHESIS OF 1,3,5-TRISUBSTITUTED PYRAZOLES

This application is a Divisional of Ser. No. 09/685,127 filed on Oct. 10, 2000, now U.S. Pat. No. 6,329,527, which claims benefit of provisional No. 60/161,666 Oct. 21, 1999.

FIELD OF THE INVENTION

The present invention relates generally to processes for the preparation of 1,3,5-trisubstituted pyrazoles and intermediates for the synthesis of the same, such pyrazoles being useful as factor Xa inhibitors.

BACKGROUND OF THE INVENTION 1,3,5-Trisubstituted-pyrazole compounds of the type shown below are currently being studied as factor Xa inhibitors in clinical settings. As one of ordinary skill in the art understands, clinical trials and NDA submissions require practical, large-scale synthesis of the active drug.

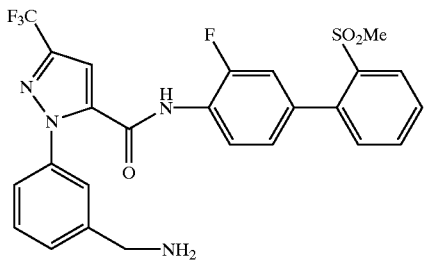

Consequently, it is desirable to find new synthetic procedures for making 1,3,5-trisubstituted pyrazoles.

SUMMARY OF THE INVENTION

Accordingly, one object of the present invention is to provide a novel process for making 1,3,5-trisubstituted pyrazoles.

It is another object of the present invention to provide novel intermediates for the syntheses of the same 1,3,5-trisubstituted pyrazoles.

These and other objects, which will become apparent during the following detailed description, have been achieved by the inventors' discovery that compounds of formula I can be formed from aryl hydrazines.

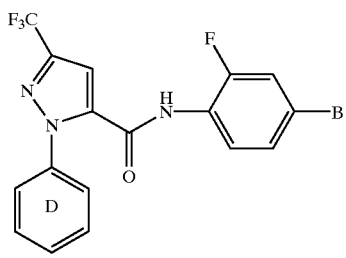

DETAILED DESCRIPTION OF THE INVENTION

Thus, in a first embodiment, the present invention provides a novel process for preparing a compound of formula I:

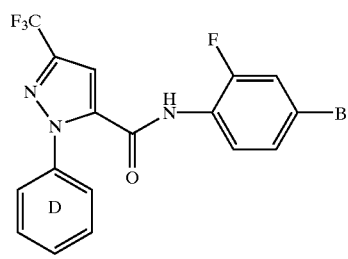

wherein ring D is selected from 2-(aminomethyl)phenyl, 3-(aminomethyl)phenyl, and (3-amino)benz[d]isoxazol-6-yl; and B is 2-MeSO$_2$-phenyl or 2-NH$_2$SO$_2$-phenyl, the process comprising:

(a) acylating a hydrazine of formula II to form a compound of formula III:

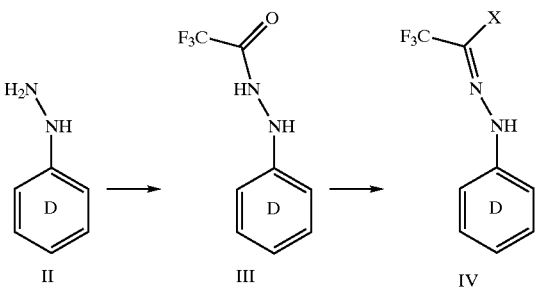

wherein ring D is selected from 2-cyanophenyl, 3-cyanophenyl, 3-cyano-4-fluorophenyl, 2-(PgNHCH$_2$)phenyl, and 3-(PgNHCH$_2$)phenyl, and Pg is an amine protecting group;

(b) converting a compound of formula III to a compound of formula IV, wherein X is selected from Cl, OMs, Br, OSO$_2$Ph, and OTs;

(c) contacting a compound of formula IV with a base to form a dipolar compound of formula V:

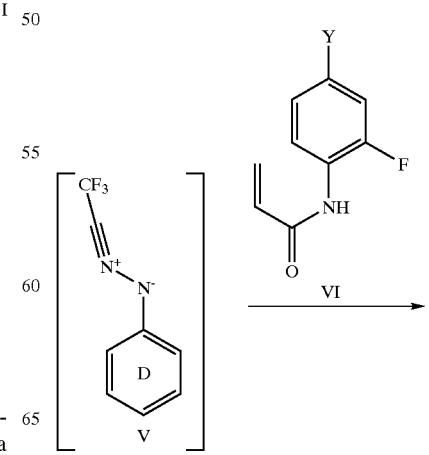

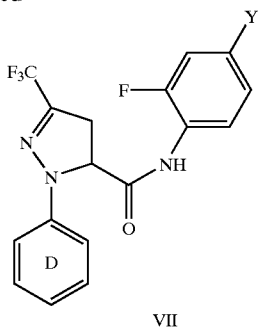

VII (d) contacting a compound of formula V in situ with a dipolarophile of formula VI to form a compound of formula VII, wherein Y is selected from Br, 2-MeSO$_2$-phenyl, 2-MeS-phenyl, 2-NH$_2$SO$_2$-phenyl, and 2-PgNHSO$_2$-phenyl;

(e) converting a compound of formula VII to a compound of formula I by subjecting it to the following reactions, which may be performed, when applicable, in any order:
(e1) oxidizing the pyrazoline to a pyrazole;
(e2a) when Y=Br, converting the Br group to 2-MeS-phenyl, 2-SO$_2$Me-phenyl, or 2-SO$_2$NH$_2$-phenyl;
(e2b) when Y=2-MeS-phenyl, converting the MeS-group to MeSO$_2$—;
(e3a) when ring D is cyanophenyl, converting this group to aminomethylphenyl or (PgNHCH$_2$)phenyl;
(e3b) when ring D is 3-cyano-4-fluorophenyl, converting this ring to (3-amino)benz [d]isoxazol-6-yl; and,
(e4) when Pg is present, removing the protecting group.

In another embodiment, step (b) is performed by contacting a compound of formula III with a sulfonyl chloride in the presence of an amine base, wherein the amine base is capable of forming a tertiary amine hydrogen chloride in situ and delivering a chloride in situ to form a compound of formula IV wherein X is Cl;
wherein the sulfonyl chloride is selected from methylsulfonyl chloride, phenylsulfonyl chloride and toluenesulfonyl chloride, the amine base is selected from triethylamine, diisopropylethylamine, and N-methylmorpholine.

In another embodiment, the sulfonyl chloride is phenylsulfonyl chloride and the amine base is diisopropylethylamine.

In another embodiment, step (b) is performed by contacting a compound of formula III with a sulfonyl chloride in the presence of an amine base, followed by contacting the resultant sulfonyl compound with a tertiary amine hydrogen chloride to form a compound of formula IV wherein X is Cl;
wherein the sulfonyl chloride is selected from methylsulfonyl chloride, phenylsulfonyl chloride and toluenesulfonyl chloride, the amine base is selected from triethylamine, diisopropylethylamine, and N-methylmorpholine.

In another embodiment, in (e) the compound of formula VII is converted to a compound of formula I by subjecting compound VII to the following reactions, that are performed, when applicable, in the order shown:
(e1) oxidizing the pyrazoline to a pyrazole;
(e2a) when Y=Br, converting the Br group to 2-MeS-phenyl, 2-SO$_2$Me-phenyl, or 2-SO$_2$NH$_2$-phenyl;
(e2b) when Y=2-MeS-phenyl, converting the MeS-group to MeSO$_2$—;
(e3a) when ring D is cyanophenyl, converting this group to aminomethylphenyl or (PgNHCH$_2$)phenyl;
(e3b) when ring D is 3-cyano-4-fluorophenyl, converting this ring to (3-amino)benz[d]isoxazol-6-yl; and,
(e4) when Pg is present, removing the protecting group.

In another embodiment, in (e) the compound of formula VII is converted to a compound of formula I by subjecting compound VII to the following reactions, that are performed, when applicable, in the order shown:
(e1) oxidizing the pyrazoline to a pyrazole;
(e3a) when ring D is cyanophenyl, converting this group to aminomethylphenyl or (PgNHCH$_2$)phenyl;
(e3b) when ring D is 3-cyano-4-fluorophenyl, converting this ring to (3-amino)benz[d]isoxazol-6-yl;
(e2a) when Y=Br, converting the Br group to 2-MeS-phenyl, 2-SO$_2$Me-phenyl, or 2-SO$_2$NH$_2$-phenyl;
(e2b) when Y=2-MeS-phenyl, converting the MeS-group to MeSO$_2$—; and,
(e4) when Pg is present, removing the protecting group.

In another embodiment, in (e) the compound of formula VII is converted to a compound of formula I by subjecting compound VII to the following reactions, that are performed, when applicable, in the order shown:
(e2a) when Y=Br, converting the Br group to 2-MeS-phenyl, 2-SO$_2$Me-phenyl, or 2-SO$_2$NH$_2$-phenyl;
(e2b) when Y=2-MeS-phenyl, converting the MeS-group to MeSO$_2$—;
(e1) oxidizing the pyrazoline to a pyrazole;
(e3a) when ring D is cyanophenyl, converting this group to aminomethylphenyl or (PgNHCH$_2$)phenyl;
(e3b) when ring D is 3-cyano-4-fluorophenyl, converting this ring to (3-amino)benz[d]isoxazol-6-yl; and,
(e4) when Pg is present, removing the protecting group.

In another embodiment, in (e) the compound of formula VII is converted to a compound of formula I by subjecting compound VII to the following reactions, that are performed, when applicable, in the order shown:
(e2a) when Y=Br, converting the Br group to 2-SO$_2$Me-phenyl or 2-SO$_2$NH$_2$-phenyl;
(e2b) when Y=2-MeS-phenyl, converting the MeS-group to MeSO$_2$—;
(e3a) when ring D is cyanophenyl, converting this group to aminomethylphenyl or (PgNHCH$_2$)phenyl;
(e3b) when ring D is 3-cyano-4-fluorophenyl, converting this ring to (3-amino)benz[d]isoxazol-6-yl;
(e1) oxidizing the pyrazoline to a pyrazole; and,
(e4) when Pg is present, removing the protecting group.

In another embodiment, in (e) the compound of formula VII is converted to a compound of formula I by subjecting compound VII to the following reactions, that are performed, when applicable, in the order shown:
(e3a) when ring D is cyanophenyl, converting this group to aminomethylphenyl or (PgNHCH$_2$)phenyl;
(e3b) when ring D is 3-cyano-4-fluorophenyl, converting this ring to (3-amino)benz[d]isoxazol-6-yl;
(e1) oxidizing the pyrazoline to a pyrazole;
(e2a) when Y=Br, converting the Br group to 2-MeS-phenyl, 2-SO$_2$Me-phenyl, or 2-SO$_2$NH$_2$-phenyl;
(e2b) when Y=2-MeS-phenyl, converting the MeS-group to MeSO$_2$—; and,
(e4) when Pg is present, removing the protecting group.

In another embodiment, in (e) the compound of formula VII is converted to a compound of formula I by subjecting compound VII to the following reactions, that are performed, when applicable, in the order shown:
(e3a) when ring D is cyanophenyl, converting this group to aminomethylphenyl or (PgNHCH$_2$)phenyl;

(e3b) when ring D is 3-cyano-4-fluorophenyl, converting this ring to (3-amino)benz[d]isoxazol-6-yl;
(e2a) when Y=Br, converting the Br group to 2-MeS-phenyl, 2-SO₂Me-phenyl, or 2-SO₂NH₂-phenyl;
(e2b) when Y=2-MeS-phenyl, converting the MeS-group to MeSO₂—;
(e1) oxidizing the pyrazoline to a pyrazole; and,
(e4) when Pg is present, removing the protecting group.

In a second embodiment, the present invention provides a novel process for preparing a compound of formula I:

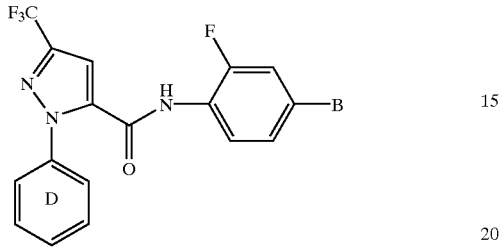

wherein ring D is 2-(aminomethyl)phenyl, 3-(aminomethyl)phenyl, or (3-amino)benz[d]isoxazol-6-yl and B is 2-MeSO₂-phenyl or 2-NH₂SO₂-phenyl, the process comprising:

(f) acylating a hydrazine of formula II to form a compound of formula III:

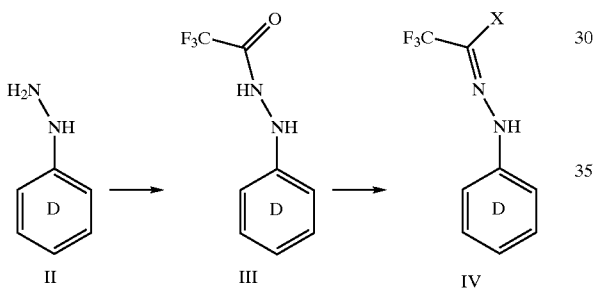

wherein ring D is selected from 2-cyanophenyl, 3-cyanophenyl, 3-cyano-4-fluorophenyl, 2-(PgNHCH₂)phenyl, and 3-(PgNHCH₂)phenyl, and Pg is an amine protecting group;

(g) converting a compound of formula III to a compound of formula IV, wherein X is selected from Cl, OMs, Br, OSO₂Ph, and OTs;

(h) contacting a compound of formula IV with a base to form a dipolar compound of formula V:

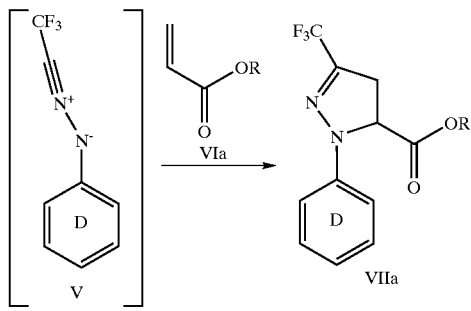

(i) contacting a compound of formula V in situ with a dipolarophile of formula VIa to form a compound of formula VIIa, wherein R is selected from H, Me, Et, and n-Pr;

(j) converting a compound of formula VIIa to a compound of formula I by subjecting it to the following reactions, which may be performed, when applicable, in any order:

(e1) oxidizing the pyrazoline to a pyrazole;
(j1) when R is other than H, hydrolyzing the compound of formula VIIa to its corresponding acid;
(j2) when R is H, contacting the acid of formula VIIa with an aniline of formula VIb to form an amide;

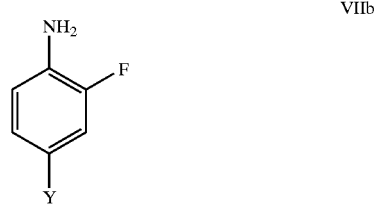

wherein Y is selected from Br, 2-MeSO₂-phenyl, 2-MeS-phenyl, 2-NH₂SO₂-phenyl, and 2-PgNHSO₂-phenyl;

(e2a') when Y=Br, converting the Br group to 2-MeS-phenyl, 2-SO₂Me-phenyl, or 2-SO₂NH₂-phenyl;
(e2b') when Y=2-MeS-phenyl, converting the MeS-group to MeSO₂—;
(e3a) when ring D is cyanophenyl, converting this group to aminomethylphenyl or (PgNHCH₂)phenyl;
(e3b) when ring D is 3-cyano-4-fluorophenyl, converting this ring to (3-amino)benz[d]isoxazol-6-yl; and,
(e4) when Pg is present, removing the protecting group.

In another embodiment, the present invention provides novel compounds of formula IX:

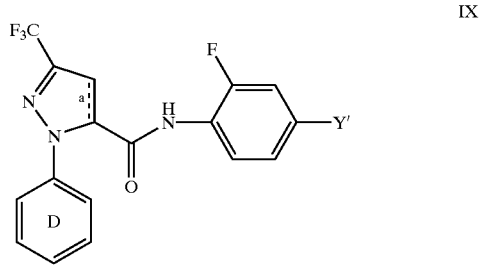

wherein ring D is 2-cyanophenyl, 2-(PgNHCH₂)phenyl, 2-(aminomethyl)phenyl, 3-cyanophenyl, 3-(PgNHCH₂)phenyl, 3-(aminomethyl)phenyl, 3-cyano-4-fluorophenyl, and (3-amino)benz[d]isoxazol-6-yl;

Y' is selected from Br, H, PgHNSO₂Ph, H₂NSO₂Ph, 2-MeSPh, and 2-MeSO₂Ph;

bond a is absent or is a single bond; and,

Pg is an amine protecting group selected from Boc and TFA.

In another embodiment, the present invention provides novel compounds of formula X:

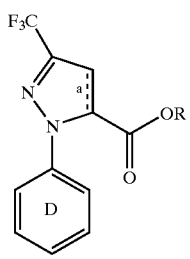

wherein R is selected from H, Me, Et, and n-Pr;
ring D is 2-cyanophenyl, 2-(PgNHCH₂)phenyl, 2-(aminomethyl)phenyl, 3-cyanophenyl, 3-(PgNHCH₂)phenyl, 3-(aminomethyl)phenyl, 3-cyano-4-fluorophenyl, and (3-amino)benz[d]isoxazol-6-yl;
bond a is absent or is a single bond; and,
Pg is an amine protecting group selected from Boc and TFA.

Definitions

The present invention can be practiced on multigram scale, kilogram scale, multikilogram scale, or industrial scale. Multigram scale, as used herein, is preferable in the sale wherein at least one starting material is present in 10 grams or more, more preferable at least 05 grams or more, even more preferably at least 100 grams or more. Multikilogram scale, as used herein, is intended to mean the scale wherein more than one kilo of at least one starting material is used. Industrial scale as used herein is intended to mean a scale which is other than a laboratory sale and which is sufficient to supply product sufficient for either clinical tests or distribution to consumers.

As used herein, equivalents are intended to mean molar equivalents unless otherwise specified.

As used herein, the term "amino protecting group" (or "N-protected") refers to any group known in the art of organic synthesis for the protection of amine groups. As used herein, the term "amino protecting group reagent" refers to any reagent known in the art of organic synthesis for the protection of amine groups that may be reacted with an amine to provide an amine protected with an amine-protecting group. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York, (1981), the disclosure of which is hereby incorporated by reference. Examples of amine protecting groups include, but are not limited to, the following: 1) acyl types such as formyl, trifluoroacetyl (TFA), phthalyl, and p-toluenesulfonyl; 2) aromatic carbamate types such as benzyloxycarbonyl (cbz) and substituted benzyloxycarbonyls, 2-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

Amine protecting groups may include, but are not limited to the following: 2,7-di-t-butyl-[9-(10,10-dioxo-10,10,10-tetrahydrothio-xanthyl)]methyloxycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl)ethyloxycarbonyl; benzyloxycarbonyl; p-nitrobenzyloxycarbonyl; 2-(p-toluenesulfonyl)ethyloxycarbonyl; m-chloro-p-acyloxybenzyloxycarbonyl; 5-benzyisoxazolylmethyloxycrbonyl; p-(dihydroxyboryl)benzyloxycarbonyl; m-nitrophenyloxycarbonyl; o-nitrobenzyloxycarbonyl; 3,5-dimethoxybenzyloxycrbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; 2-furanylmethyloxycarbonyl; phthalimide; dithiasuccinimide; 2,5-dimethylpyrrole; benzyl; 5-dibenzylsuberyl; triphenylmethyl; benzylidene; diphenylmethylene; and, methanesulfonamide.

Synthesis

By way of example and without limitation, the present invention may be further understood by the following schemes and descriptions.

Step (a): Acetylation of arylhydrazine (II) to prepare acetylated arylhydrazine (III)

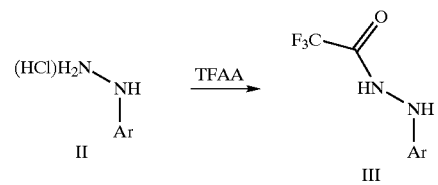

This reaction involves the acetylating of an arylhydrazine (II) or a salt thereof (e.g., HCl) with an acetylating reagent (e.g., trifluoroacetic anhydride (TFAA)) to produce the corresponding aceytlated arylhydrazine (III). From about 1.0–1.1 equivalents of acetylating reagent are used, preferably about 1.0 equivalent, especially when the reaction is run on large scale. Surprisingly, no base is necessary to run the acetylation. A base may be used, if desired. The preferred reaction temperature is about 0–25° C. In order to control the internal temperature and maintain it at or below 25° C., the acetylating reagent addition rate is adjusted accordingly. Such temperature control avoids formation of the bis-trifluoroacetylated by-product. The reaction is normally complete in about 1–2 h at from 0–25° C. Preferably, THF is used as solvent, though other aprotic solvents can be used. The product is isolated by stripping off most of the solvent (i.e., THF) in vacuo when the reaction is complete and titrating the residue with a non-polar solvent, such as a hydrocarbon (e.g., heptanes) to precipitate the product, that is pure enough to carry forward without further purification.

Step (b): Preparation of 1,3-dipole (nitrileimine) precursors, hydrazonoyl halides (IVa–b) and hydrazonoyl sulfonates (IVc–e)

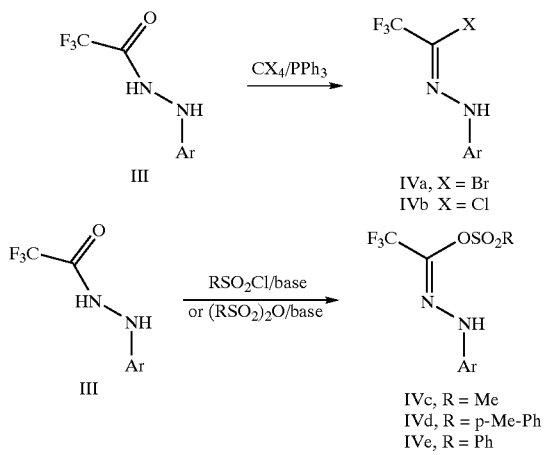

The 1,3-dipole used in the present invention is a nitrileimine (V), which is generated by treating its precursor (IV), such as hydrazonoyl halide (IVa or IVb) or a hydrazonoyl sulfate (IVC, IVd, or IVe), with a base. The in situ generated nitrileimine (V) can be directly reacted with a dipolarophile, such as a substituted alkene, to produce the corresponding cycloaddition product, such as a substituted pyrazoline. The procedure for preparation of the corresponding hydrazonoyl bromide (IVa) and hydrazonoyl chloride (IVb) has been previously described (see Chem. Pharm. Bull. 1988, 36(2), 800).

Sulfonyl Chloride as the Sulfonating Agent

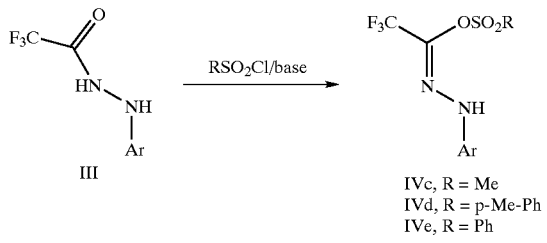

About 1.0–1.5 equivalents of sulfonyl chloride is used, with the preferred molar ratio being about 1.05–1.1. Preferred sulfonyl chlorides are methyl sulfonyl chloride, phenyl sulfonyl chloride and toluenyl sulfonyl chlorde, with phenyl sulfonyl chloride being most preferred. A base is used to initiate the sulfonation reaction. The preferred base is a trialkylamine (pKa 10–11), such as triethylamine or diisopropylethylamine (Hunig's base), or a cyclic tertiary amine (pKa 7–8), such as N-methylmorpholine (NMM), with diisopropylethylamine being most preferred. When substrate (III) contains electron-withdrawing functional group(s) on its aromatic ring, a cyclic tertiary amine is the preferred base; on the other hand, when substrate (III) contains electron-donating functional group(s) on its aromatic ring, a trialkylamine is preferred. The preferred reaction temperature is from 0–25° C. The reaction time depends on the reactivity of the substrate (III) and the sulfonating agent. Normally, the sulfonation reaction is complete in 1–4 h at 0–25° C. The preferred solvents for this sulfonation reaction are ethyl acetate (EtOAc), toluene or methylene chloride, with EtOAc being most preferred.

The regioselectivity of the sulfonation reaction (oxygen vs nitrogen) depends mainly on the reactivity of substrate (III). Selective O-sulfonation can be reached (oxygen vs nitrogen>20:1) when an electron-deficient arylhydrazine (III) (e.g., trifluoroacylated arylhydrazine) is used. However, the regioselectivity is reduced dramatically (oxygen vs nitrogen<4:1) when an electron-enriched trifluoroacylated arylhydrazine (III) is employed. Therefore, the nucleophilicity and basicity of the nitrogen atom connected to the aromatic ring is greatly affected by the ring substitution pattern. The choice of base can also affect this selectivity.

The present invention also provides a novel and efficient preparation of hydrazonoyl sulfonates (IVc, IVd, and IVe) as the corresponding 1,3-dipole precursors in the cycloaddition reaction.

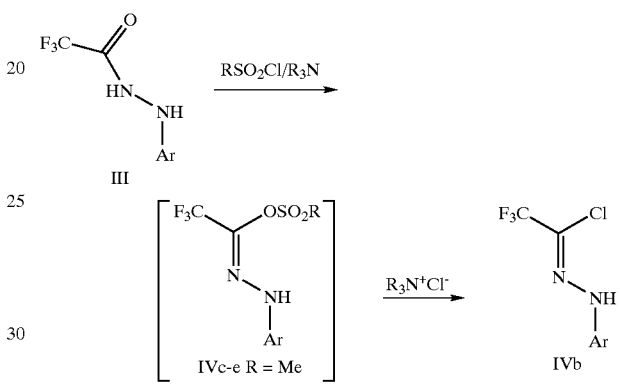

The hydrazonoyl sulfonates (IVc, IVd, or IVe) can be readily transformed in situ into the corresponding hydrazonoyl chloride (IVb) by reacting with an in situ generated tertiary amine hydrogen chloride salt. Phenyl sulfonyl chloride is the preferred sulfonating reagent for this in situ reaction. For large-scale synthesis, this protocol for the preparation of hydrazonoyl chloride (IVb) can be very convenient. Compared with the literature-reported protocol (see Chem. Pharm. Bull. 1988, 36(2), 800), this methodology eliminates the use of the toxic carbon tetrahalide and large amounts of triphenylphosphine.

Hydrazonoyl sulfonates (IVc, IVd, and IVe) can be quantitatively converted into the corresponding hydrazonoyl chloride (IVb) by reacting with in situ generated trialkylamine hydrogen chloride salt or cyclic tertiary amine hydrogen chloride salt. This is a particularly useful reaction for the preparation of the hydrazonoyl chloride (IVb). Hydrazonoyl chloride (IVb) formation through this in situ transformation from the corresponding hydrazonoyl sulfonates (IVc–e) is affected by the reactivity of the particular tertiary amine hydrogen chloride salt. Compared with the cyclic tertiary amine hydrogen chloride salt, the trialkylamine hydrogen chloride salt is a better chlorinating agent to affect this transformation. Consequently, diisopropylethylamine is a most preferred base for this in situ reaction. In general, hydrazonyl sulfates (IVc, IVd, and IVe) are the kinectically favored products and can be obtained by quenching the sulfonation reaction with water at lower temperatures in short reaction periods. However, the thermodynamic product will be hydrazonoyl chloride (IVb) exclusively if the reaction is conducted at higher temperatures for relatively longer periods of time.

Sulfonic Anhydride as Sulfonation Agent

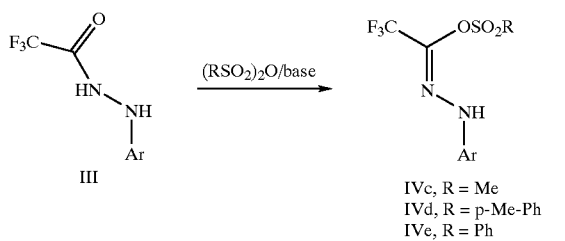

IVc, R = Me
IVd, R = p-Me-Ph
IVe, R = Ph

Preferably, about 1.0–1.1 equivalents of sulfonic anhydride agent are used. A weak base is used in the reaction to promote it. Pyridine (pKa 5.15) is a preferred base for this reaction, even though it is not strong enough to initiate the sulfonation reaction between sulfonyl chloride and trifluoroacylated arylhydrazine (III) in the alternative approach detailed above. The preferred reaction temperature is from 0–25° C. The reaction is usually complete in 1–2 h at 0–25° C. The preferred solvent is EtOAc.

Because the sulfonic anhydride is a relatively stronger sulfonating agent compared with the corresponding sulfonyl chloride used in approach A, the sulfonation reaction bwithdrawing functional group(s) on its aromatic ring and the setween the substrate (III) carrying the electron-ulfonic anhydride is more regioselective. However, for the substrate (TII) carrying the electron-donating functional group(s) on its aromatic ring, little improvement for the regioselectivity was observed in this alternative reaction.

This approach produces only the desired hydrazonoyl sulfonate (IVc–e), no corresponding hydrazonoyl chloride (IVb) is generated because of the absence of a chloride source, such as tertiary amine hydrogen chloride salt, in the reaction mixture. Therefore, it can be used as the method to prepare pure hydrazonoyl sulfonates (IVc–e).

Preparation of N-aryl and N-biaryl acrylamides (VIb and VIc) as dipolarophiles

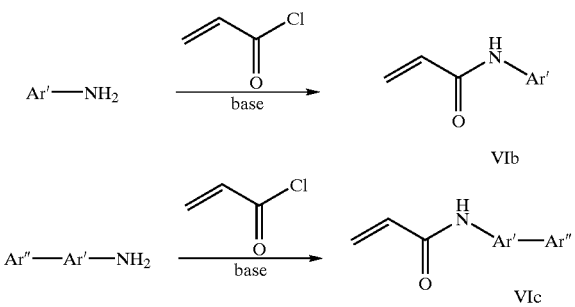

Acrylamides (VIb and VIc) are formed by reacting acryloyl chloride and a substituted aniline. A base is used to promote the reaction. Preferably, 1.0–2.0 equivalents of acryloyl chloride are used, more preferably about 1.2–1.5 equivalents. A trialkylamine, such as triethylamine, or a cyclic tertiary amine, such as N-methylmorpholine (NMM) is used as a base to promote this reaction, with NMM being preferred. A preferred solvent is EtOAc, THF, $CH_2Cl_2$, or acetonitrile, with EtOAc being more preferred. The reaction is preferably run at a temperature of from 0–25° C. and is usually complete in 1–4 h at 0–25° C. The product can be readily isolated by simple aqueous work-up.

Step (c) and Step (d): 1,3-Dipolar cycloaddition
(wherein Ar'=2-F-4-Y-phenyl)

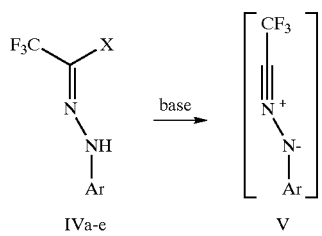 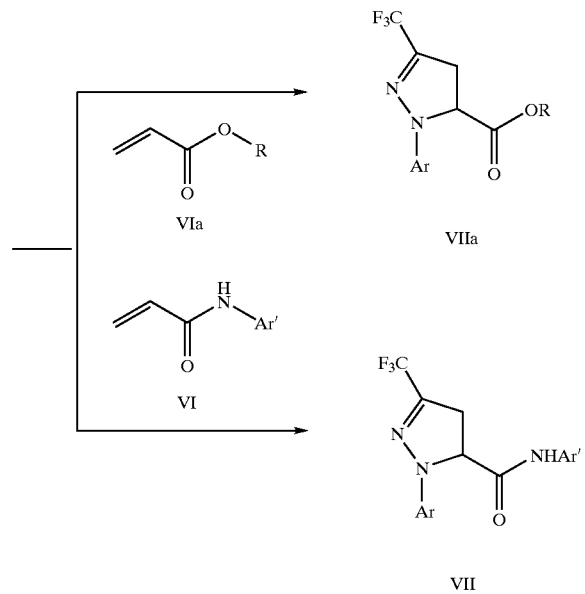

The 1,3-dipolar cycloaddition reaction of the present invention involves reaction between an in situ generated nitrileimine (V, 1,3-dipole) and a dipolarophile, such as a substituted alkene derivative (VI or VIa). This cycloaddition reaction regiospecifically generates the corresponding substituted pyrazoline (VII or VIIa). The preferred solvent for the cycloaddition reaction is EtOAc.

Generation of nitrileimine 1,3-dipole (V) can be achieved by reacting a base with its precursor (IVa–c). The preferred base is a trialkylamine, such as triethylamine or Hunig's base, or a cyclic tertiary amine, such as NMM. Preferably, about 2–3 equivalents of base are used.

Factors like the reactivities of 1,3-dipole precursors (IVa–e) and dipolarophiles (VI or VIa) can affect the cycloaddition reaction rate. Therefore, the reaction temperature and time may be varied. Qualitatively, the order of the reactivity of the 1,3-dipole precursors (IV) is: hydrazonoyl mesylate (IVc)>hydrazonoyl bromide (IVa), tosylate (IVd), benzenesulfonate (IVe)>>hydrazonoyl chloride (IVb). The order of the reactivity of the dipolarophile (VI) is: alkyl acrylate (VIa)>N-aryl acrylamide>N-biaryl acrylamide. When an alkyl acrylate (VIa is reacted with hydrazonoyl bromide (IVa) or hydrazonoyl sulfonates (IVc–e)), the cycloaddition reaction can be done at room temperature in about 4–12 h. However, the cycloaddition reaction between hydrazonoyl chloride (IVb) and dipolarophiles (VI or VIa) is preferably run at elevated temperature (50–80° C.) for 12–24 h.

With a monosubstituted alkene as dipolarophile (VI), such as ethyl acrylate (VIa) or N-aryl/biaryl acrylamide, the 1,3-dipolar cycloaddition reaction regiospecifically generates 5-substituted pyrazoline (VII or VIIa) as the only product.

Step (e1): Oxidation of Pyrazoline to Pyrazole

Even though there are many oxidative dehydrogenation methodologies reported in the literature for the preparation of substituted pyrazoles (VIII) from the corresponding pyrazolines (VII), none of them can be practically employed on a large-scale synthesis. Thus, the present invention involves two novel methods for the oxidation of the cycloaddition product pyrazoline (VII or VIIa) to pyrazole (VIII or VIIIa).

Electrophilic Chlorination of Pyrazoline (VII or VIIa) with NCS Followed by in situ Elimination of Hydrogen Chloride (wherein Ar'=2-F-4-Y-phenyl)

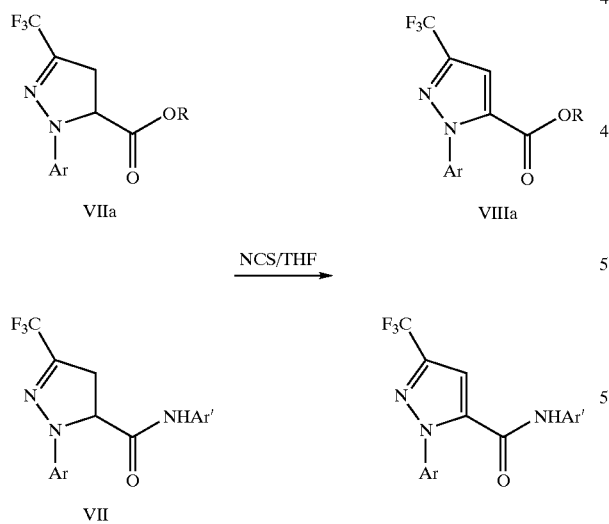

This process involves a reaction between a substituted pyrazoline (VII or VIIa) and N-chlorosuccinimide (NCS). The electrophilic chlorinated pyrazoline intermediate undergoes an in situ dehydrohalogenation to produce the corresponding pyrazole (VIII or VIIIa). Preferably, about 1.0–1.1 equivalents of N-chlorosucinimide (NCS) are used in the reaction. Excess NCS results in the undesired chlorination of the aromatic ring. Thus, it is preferable to minimize the amount of NCS used.

The preferred solvent for this aromatization reaction is THF. A polar solvent such as DMF was found to result in the formation of the aromatic ring chlorination by-product. The reaction is preferable run at 0–25° C. At room temperature, the reaction is usually complete in about 1–2 h.

Aromatic ring chlorination by-product is observed when the substrate pyrazoline (VII or VIIa) contains an electron-donating functional group(s) on its aromatic ring. Therefore, this method should be used only when the substrate pyrazoline (VII or VIIa) is substituted with electron-withdrawing functional group(s).

The oxidation product, pyrazole (VIII or VIIIa), can be isolated from the reaction mixture through routine aqueous work-up. The succinimide generated from the reaction dissolves in water. Therefore, it can be extracted readily into the aqueous layer of the work-up mixture.

Oxidation with Oxygen in Air Under Basic Conditions (wherein Ar'=2-F-4-Y-phenyl)

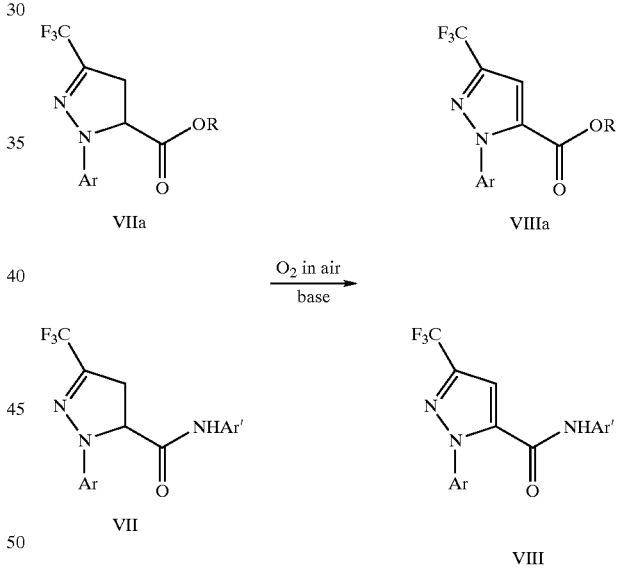

This process involves a reaction between a substituted pyrazoline (VII or VIIa) and oxygen in air under basic conditions. The enolate of 5-carboyxlate/carbamoyl substituted pyrazoline (VII or VIIa) is oxidized by oxygen in air to produce the corresponding pyrazole (VIII or VIIIa). Preferably, oxygen in air, 7% oxygen in nitrogen, or pure oxygen as is used as the oxidant. The preferred oxygen source of large scale reaction is oxygen in air (22%) or oxygen in nitrogen (7%). A relatively strong base is used to generate the corresponding substituted pyrazoline (VII or VIIa) enolate. The preferred base is potassium tert-butoxide.

A polar, aprotic solvent is preferred. The most preferred solvent is DMF or DMAC (N,N-dimethylaminoacetamide). The reaction is run from −25–25° C., with the preferred temperature range being −15–5° C. The reaction is usually complete in 1–8 h at −15–5° C. The reaction time is also dependent on the oxygen source employed.

This protocol is applicable to the oxidation of all the pyrazolines (VII or VIIa), no matter what their aromatic substitution patterns are. Therefore, it can be used for pyrazolines with electron-donating functional group(s) on their aromatic rings.

Step (e2a): Suzuki Coupling Reaction Between a Pyrazoline Or Pyrazole and an Arylboronic Acid

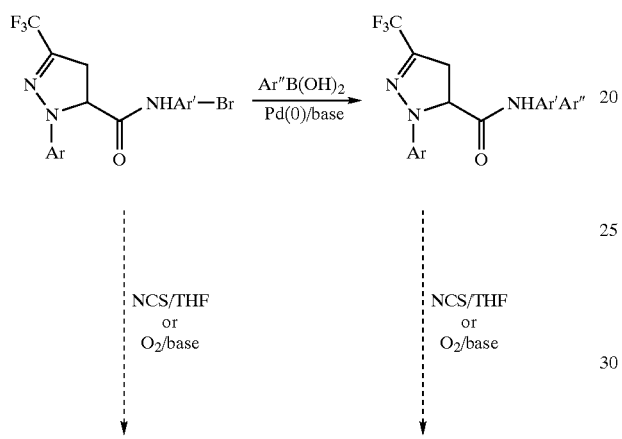

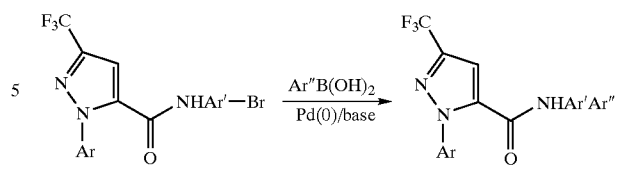

The Pd(0) catalyst used in the Suzuki coupling is preferably Pd(PPh$_3$)$_4$. About 1–5% equivalents of the catalyst are used to catalyze this coupling reaction with 2% being preferred. About 1.0–1.5 equivalents of an arylboronic acid are used, with 1–2 equivalents being preferred. A base is used to promote the Suzuki coupling reaction. The preferred base is an inorganic salt, such as potassium carbonate or sodium carbonate. The most preferred base is sodium carbonate. A mixed solvent system is used for this Suzuki coupling reaction. The preferred solvent system is toluene/ethanol/water (2–4:1:1 v/v/v). Preferably the reaction is run at elevated temperature, the preferred temperature range being 70–80° C. Usually, the reaction is complete in 4–20 h at 70–80° C.

Step (e2b): Oxidation of Thiomethyl (—SMe) Functionality to Sulfone (—SO$_2$Me)

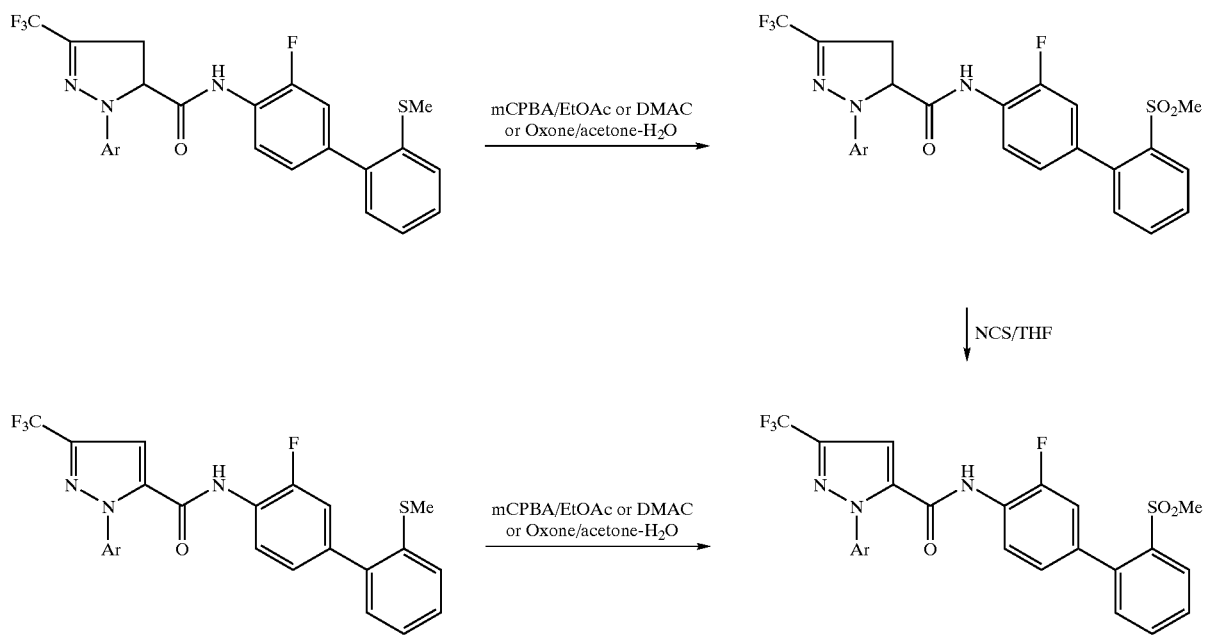

A selected class of oxidation reagents can be used to oxidize the thiomethyl (—SMe) functionality to the corresponding sulfone (—SO$_2$Me). The preferred oxidants are mCPBA and Oxone®. About 2–10 equivalents of mCPBA or Oxone® are used to do this oxidation reaction, with 2–5 eqivalents being preferred. Several different solvents or solvent systems are used for this oxidation reaction. The choice for the solvent or solvent system is dependent on the oxidant used for the reaction. With mCPBA as an oxidant, ethyl acetate (EtOAc) is preferred. With Oxone® as an oxidant, the preferred solvent system is a mixture of acetone and water in a volume ratio of one to one. The oxidation reaction can be run at 25–50° C., depending on the oxidant used for the reaction. With mCPBA as an oxidant, the oxidation reaction can be run at room temperature (20–25° C.). But, when Oxone® is used as an oxidant, the reaction is run at elevated temperature, the preferred temperature range being 40–50° C. Generally, the reaction is complete in 5–20 h at 20–50° C.

Step (e3a) and e3b): Converting Ring D to a benzyl amine or amino-benzisoxazole 1). Converting Ring D to a Benzylamine (e3a) (wherein Ar'=2-F-4-Y-phenyl)

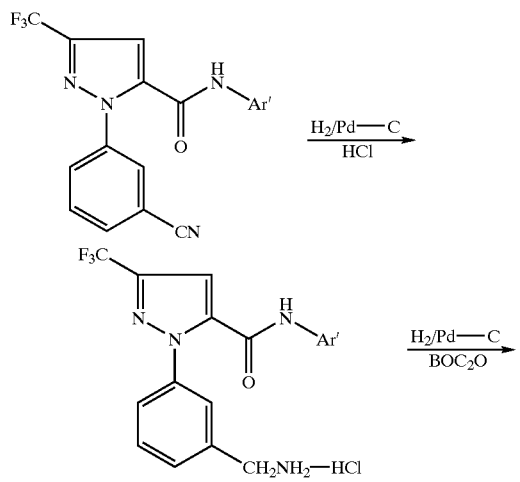

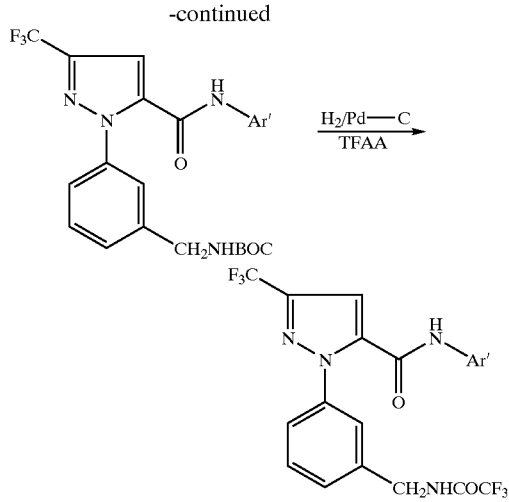

Reduction of the cyano group to a benzylamine can be achieved with a chemical reducing reagent, such as NaBH$_4$, or via Pd(0) catalyzed hydrogenation. The preferred reduction procedure is palladium catalyzed hydrogenation. About 1–2% (weight) of the palladium on charcoal (5% or 10%) can be used. The preferred solvent for the hydrogenation reaction is ethanol. The reaction is normally run at 20–25° C. Usually, the reaction is complete in 4–6 h at 20–25° C. under 50–55 psig hydrogen pressure. When the reaction is conducted in the existence of an acid, such as hydrochloric acid (HCl), the corresponding salt, such as benzylamine hydrochloride salt, is obtained. When the reduction reaction is conducted in the existence of an electrophile that is used for the in situ protection of the generated benzylamine, such as di-tert-butyl dicarbonate (Boc$_2$O) or trifluoroacetic acid anhydride (TFAA), the corresponding protected benzylamine (Boc or TFA) is obtained.

2). Converting Ring D to an Aminobenzisoxazole Ring (e3b) (wherein Ar'=2-F-4-Y-phenyl)

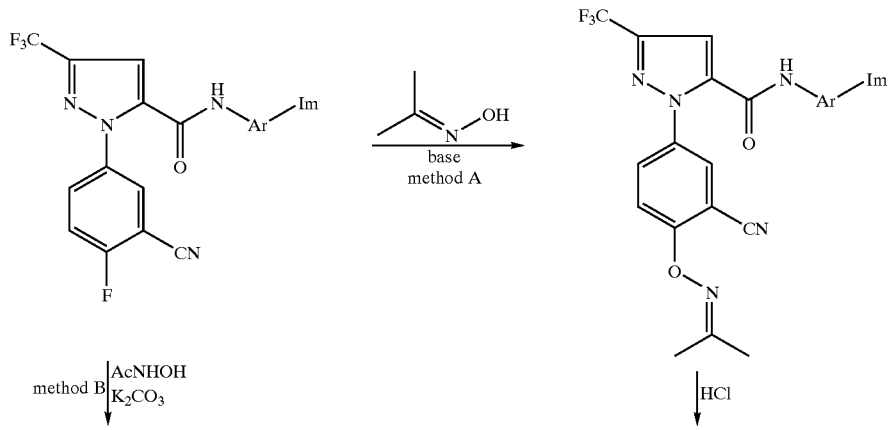

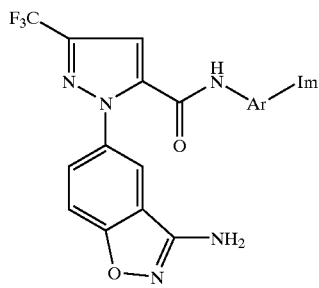
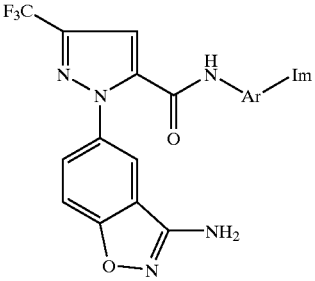

Converting of the ortho fluoro/cyano substituents to the corresponding aminobenzisoxazole functionality in ring D is achieved in two ways. The first method involves a two-step sequential reaction. Substitution of the fluoro functionality ortho to the cyano group with an acetone oxime in the existence of a base, such as potassium tert-butoxide or NaH, in anhydrous solvent, such as THF or DMF, generates the corresponding acetone oxime substituted intermediate. This intermediate is subsequently converted into the desired aminobenzisoxazole ring by treating with an acid. About 2–4 equivalents of acetone oxime are used for this substituted reaction. The preferred base is sodium hydride. The anhydrous DMF is the preferred solvent. At 0–25° C., the substution reaction is complete in 1–2 h.

The second method involves a one-step reaction between fluoro/cyano substituted substrate and an acetohydroxamic acid. Potassium carbonate is preferably used as the base to promote the reaction. Normally, 5–10 equivalents potassium carbonate is used for the reaction. The preferred solvent system is a mixture of DMF and water in a volume ratio 10–15 to 1. The reaction is conducted at 20–30° C. At such a temperature range, the reaction is usually complete in 10–15 h.

Step (e4): Removing Protection Group

1). Removing Boc Protection Group to the Corresponding

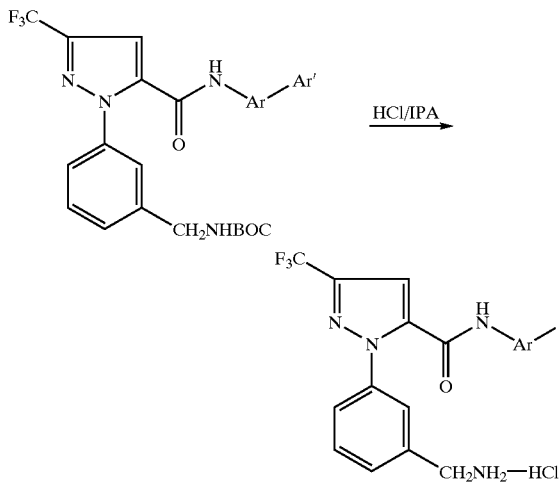

The Boc protection group is removed to release the corresponding benzylamine by treating the N-Boc benzylamine with an acid. The typical acid used for this deprotection reaction is hydrochloric acid (HCl). The preferred HCl form is 5 to 6 N HCl solution in isopropyl alcohol (IPA). By treatment the corresponding Boc protected benzylamine with excess amount of HCl solution in isopropyl alcohol (IPA) at 20–25° C. for several hours, the corresponding benzylamine hydrochloride salt is generated. Normally, 1–5 equivalents of HCl solution in isopropyl alcohol is used.

Trifluoroacetic acid (TFA) is also useful to remove the Boc group. The resulting deprotection product is the corresponding benzylamine trifluoroacetic acid salt. Normally, the excess amount of trifluoroacetic acid is used. The deprotection reaction is also run at 20–25° C. The reaction is usually complete in 2–10 h.

2). Removing TFA Protection Group to Release the Corresponding Benzylamine

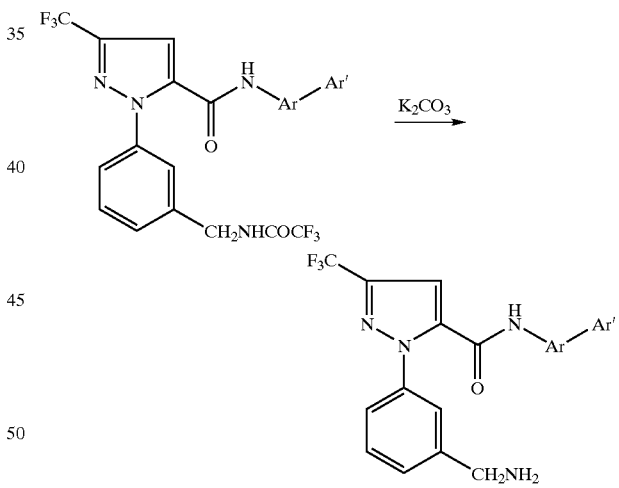

Trifluoroacetyl protection group of benzylamine is removed by treating the corresponding TFA protected benzylamine with an inorganic base, such as sodium hydroxide or potassium hydroxide, or an inorganic salt, such as potassium carbonate. The preferred base is potassium carbonate. Normally, 1 to 4 equivalents of potassium carbonate are used for the reaction. Alkyl alcohol, such as methanol or ethanol, is used as solvent. The reaction is run at 20–60° C. The preferred temperature range is 50–60° C. Normally, the reaction is complete in 2 to 10 h at 50–60° C. The deprotection reaction under such a condition generates the corresponding benzylamine as a free base.

3). Removing tert-Butyl Protection Group from Sulfamide To Release the Corresponding Sulfamide

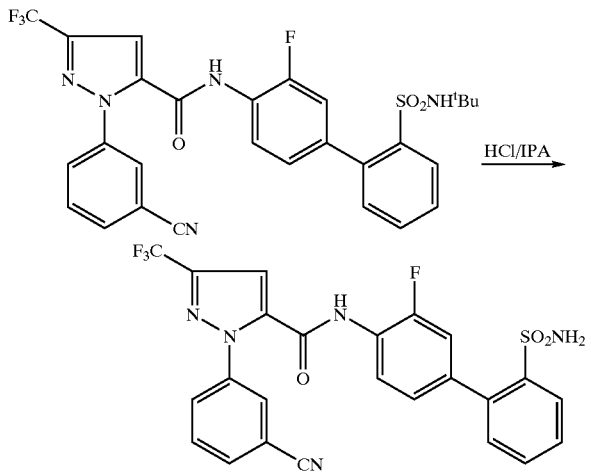

Removal of the tert-butyl group to release the corresponding sulfamide is also conducted in an acidic condition. The preferred acid used for this reaction is a 5 to 6 N hydrochloric acid solution in isopropyl alcohol. Normally, an excess of hydrogen chloride is employed. The isopropyl alcohol, which makes hydrogen chloride solution, is also a reaction solvent. The reaction is usually run at an elevated temperature. The preferred temperature range is 70–80° C. The reaction is usually complete in 30 to 50 hours at 70–80° C.

Other features of the invention will become apparent in the course of the following descriptions of examplary embodiments which are given for illustration of the invention and are not intended to be limiting thereof.

EXAMPLES

Example 1

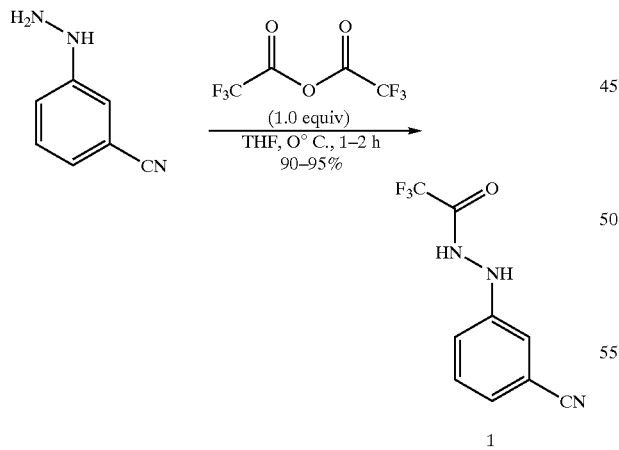

1-(3-Cyano)phenyl-2-(trifluoroacetyl)hydrazine (1)

A solution of 3-cyanobenzenehydrazine (107 g, 0.8 mol) in anhydrous THF (800 mL) was treated dropwise with a solution of trifluoroacetic anhydride (TFAA, 168.0 g, 113 mL, 0.8 mol, 1.0 equiv) in anhydrous THF (150 mL) at 5–7° C. under $N_2$. The resulting reaction mixture was then stirred at 5–15° C. for an additional 1 h. When HPLC showed the reaction was deemed complete, 700–750 mL of THF was removed in vacuo. The residual slurry was then treated with heptanes (1400 mL) with good stirring. The resulting solids were aged for 1 h at room temperature and then cooled to 0–5° C. in an ice-bath for an additional 1 h. The solids were collected by filtration, washed with heptanes (2×300 mL), and dried at 40–50° C. in vacuo for 12 h to afford the crude desired 1-(3-cyano)phenyl-2-(trifluoroacetyl)hydrazine (1, 178 g, 215 g theoretical, 83%), which was found to be essentially pure to do the following reaction without further purification. The analytically pure product (1) was obtained from recrystalization of the crude material obtained above from EtOAc/heptanes. For 1: CIMS m/z 228 ($M^+$–H, $C_9H_6F_3N_3O$).

Example 2

Method A

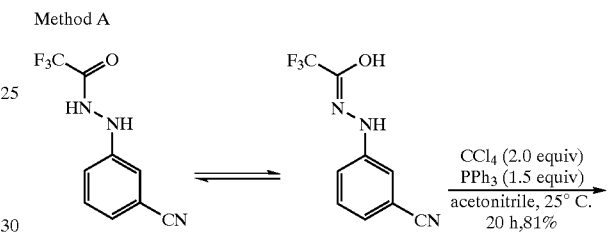

2,2,2-Trifluoro-N-(3-cyano)phenylethanehydrazonoyl chloride (2)

Method A. A suspension of 1-(3-cyano)phenyl-2-(trifluoroacetyl)hydrazine (1, 2.6 g, 11.3 mmol) in acetonitrile (20 mL) was treated with $CCl_4$ (3.48 g, 2.2 mL, 22.6 mmol, 2.0 equiv) and $PPh_3$ (4.4 g, 17.0 mmol, 1.5 equiv) at 25° C. under $N_2$. The resulting reaction mixture, which was turned into a clear solution after 10–20 min at room temperature, was then stirred at 25° C. for 14 h. When the HPLC showed that the reaction was deemed complete, the solvent was removed in vacuo. The oily residue was directly purified by the flash column chromatography ($SiO_2$, 5–20% EtOAc-hexanes gradient elution) to afford 2,2,2-trifluoro-N-(3-cyanophenyl)ethanehydrazonoyl chloride (2, 2.3 g, 2.85 g theoretical, 81%) as off-white solids. For 2: CIMS m/z 246/248 ($M^+$–H, $C_9H_5ClF_3N_3$).

Example 3

Method B

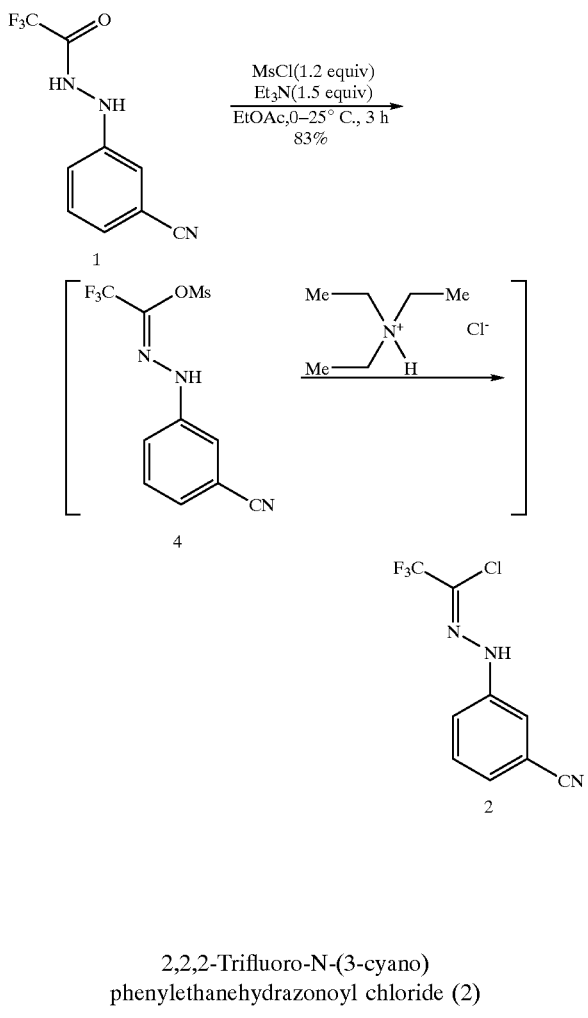

2,2,2-Trifluoro-N-(3-cyano)
phenylethanehydrazonoyl chloride (2)

Method B. A solution of 1-(3-cyano)phenyl-2-(trifluoroacetyl)hydrazine (1, 2.5 g, 10.9 mmol) in ethyl acetate (20 mL) was treated with methanesulfonyl chloride (1.50 g, 1.01 mL, 13.1 mmol, 1.2 equiv) at 0° C. under $N_2$, and the resulting reaction was added dropwise triethylamine (TEA, 1.65 g, 2.34 mL, 16.4 mmol, 1.5 equiv) at 0° C. under $N_2$. The reaction mixture was then stirred at 0° C. for 10 min before being gradually warmed to room temperature for 3 h. When the HPLC showed that the reaction was deemed complete, the reaction mixture was treated with water (20 mL) and EtOAc (20 mL). The two layers were separated, and the aqueous layer was extracted with EtOAc (20 mL). The combined organic extracts were washed with water (2×20 mL) and saturated NaCl aqueous solution (20 mL), dried over $MgSO_4$, and concentrated in vacuo. Flash column chromatography (SiO2, 10–25% EtOAc-hexanes gradient elution) afforded 2,2,2-trifluoro-N-(3-cyanophenyl) ethanehydrazonoyl chloride (2, 2.07 g, 2.47 g theoretical, 83.2%) as white solids, which was found to be identical with the material obtained from method A detailed above in every comparable aspect.

Example 4

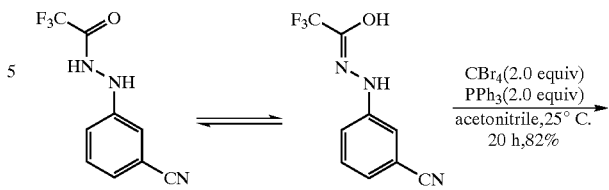

2,2,2-Trifluoro-N-(3-cyanophenyl)
ethanehydrazonoyl bromide (3)

A suspension of 1-(3-cyano)phenyl-2-(trifluoroacetyl) hydrazine (1, 2.29 g, 10.0 mmol) in acetonitrile (20 mL) was treated with $CBr_4$ (6.633 g, 20 mmol, 2.0 equiv) and $PPh_3$ (5.25 g, 20 mmol, 2.0 equiv) at 25° C. under $N_2$. The resulting reaction mixture, which was turned into a clear solution after 10–20 min at room temperature, was then stirred at 25° C. for 20 h. When the HPLC showed that the reaction was deemed complete, the solvent was removed in vacuo. The oily residue was directly purified by the flash column chromatography ($SiO_2$, 5–20% EtOAc-hexanes gradient elution) to afford 2,2,2-trifluoro-N-(3-cyanophenyl) ethanehydrazonoyl bromide (3, 2.39 g, 2.92 g theoretical, 82%) as pale-yellow solids. For 3: CIMS m/z 291/293 ($M^+$–H, $C_9H_5BrF_3N_3$).

Example 5

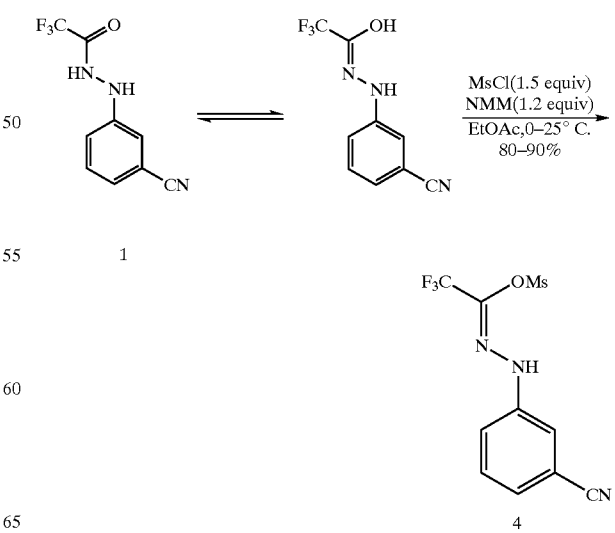

2,2,2-Trifluoro-N-(3-cyano)phenylethanehydrazonoyl mesylate (4)

A solution of 1-(3-cyano)phenyl-2-(trifluoroacetyl)hydrazine (1, 229 mg, 1.0 mmol) in ethyl acetate (3.0 mL) was treated with methanesulfonyl chloride (172 mg, 116 μL, 1.5 mmol, 1.5 equiv) at 0° C. under $N_2$, and the resulting reaction was added dropwise N-methylmorpholine (NMM, 121 mg, 132 μL, 1.2 mmol, 1.2 equiv) at 0° C. The reaction mixture was then stirred at 0° C. for 10 min before being gradually warmed to room temperature for 3–4 h. When the HPLC showed that the reaction was deemed complete, the reaction mixture was treated with water (5 mL) and EtOAc (5 mL). The two layers were separated, and the aqueous layer was extracted with EtOAc (5 mL). The combined organic extracts were washed with water (2×10 mL) and saturated NaCl aqueous solution (5 mL), dried over $MgSO_4$, and concentrated in vacuo. Flash column chromatography ($SiO_2$, 10–25% EtOAc-hexanes gradient elution) afforded 2,2,2-trifluoro-N-(3-cyanophenyl)ethane-hydrazonoyl mesylate (4, 252 mg, 311 mg theoretical, 81%) as white solids. For 4: CIMS m/z 306 ($M^+$–H, $C_{10}H_8F_3N_3O_3S$).

Example 6

Method A

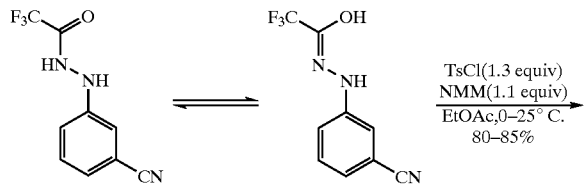

1

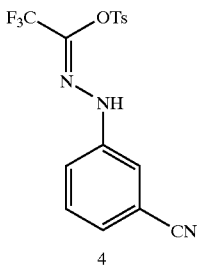

4

2,2,2-Trifluoro-N-(3-cyano)phenylethanehydrazonoyl tosylate (5)

Method A. A solution of 1-(3-cyano)phenyl-2-(trifluoroacetyl)hydrazine (1, 22.9 g, 0.1 mol) in ethyl acetate (180 mL) was treated with p-toluenesulfonyl chloride (24.8 g, 0.13 mol, 1.3 equiv) at 0° C. under $N_2$, and the resulting reaction was added dropwise a solution of N-methylmorpholine (NMM, 11.11 g, 12.1 mL, 0.11 mmol, 1.1 equiv) at 0° C. under $N_2$. The reaction mixture was then stirred at 0° C. for 10 min before being gradually warmed to room temperature for 3–4 h. When the HPLC showed that the reaction had a greater than 95% conversion, the reaction mixture was treated with water (200 mL) and EtOAc (300 mL). The resulting mixture was stirred at room temperature for 30 min. The two layers were then separated, and the aqueous layer was extracted with EtOAc (100 mL). The combined organic extracts were washed with water (2×100 mL) and saturated NaCl aqueous solution (100 mL), dried over $MgSO_4$, and concentrated in vacuo. The residual ethyl acetate solution (100 mL) was added heptanes (400 mL), and the resulting mixture was stirred at room temperature for 1 h to precipitate the desired tosylate. The solids were collected by filtration, washed with EtOAc-hexanes (1:5, 2×50 mL) and dried in vacuo. The crude desired 2,2,2-trifluoro-N-(3-cyanophenyl)ethanehydrazonoyl tosylate (5, 31.03 g, 38.3 g theoretical, 81%) was obtained as pale-yellow solids, which was found to be >96% pure by HPLC. The only observable impurity (3–4%) was found to be the corresponding iminoyl chloride (2), which will not affect the following cycloaddition reaction. The analytically pure product (5) was obtained from flash column chromatography ($SiO_2$, 5–20% EtOAc-hexanes gradient elution) purification or recrystalization (EtOAc/heptanes) of the crude 5 obtained above. For 5: CIMS m/z 382 ($M^+$–H, $C_{16}H_{12}F_3N_3O_3S$).

Example 7

Method B

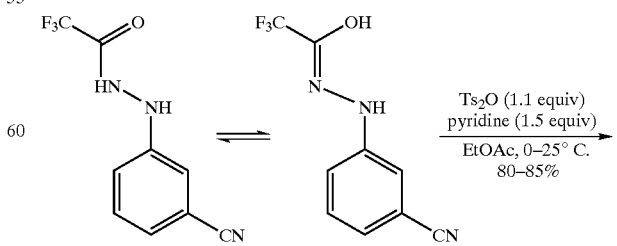

1

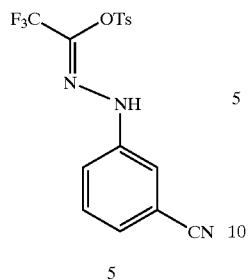

2,2,2-Trifluoro-N-(3-cyano)phenylethanehydrazonoyl tosylate (5)

Method B. A solution of 1-(3-cyano)phenyl-2-(trifluoroacetyl)hydrazine (1, 229 mg, 1.0 mmol) in ethyl acetate (3.0 mL) was treated with p-toluenesulfonyl anhydride (97% pure, 370 mg, 1.1 mmol, 1.1 equiv) at 0° C. under $N_2$, and the resulting mixture was treated dropwise with pyridine (118.7 mg, 121 μL, 1.5 mmol, 1.5 equiv) at 0° C. under $N_2$. The reaction mixture was then gradually warmed to room temperature for 2 h. When HPLC showed the reaction was deemed complete, the reaction mixture was treated with water (10 mL) and EtOAc (10 mL). The two layers were separated, and the aqueous layer was extracted with EtOAc (10 mL). The combined organic extracts were washed with water (2×10 mL) and saturated NaCl aqueous solution (10 mL), dried over $MgSO_4$, and concentrated in vacuo. The crude desired product (5, 375 mg, 383 mg theoretical, 98%), which was found to be identical with the material obtained from method A in every comparable aspect and to be essentially pure to do the following cycloaddition reaction without further purification.

Example 8

Method A

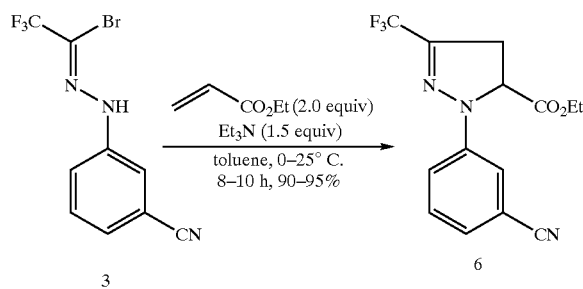

Ethyl 1-(3-cyano)phenyl-3-trifluoromethylpyrazoline-5-carboxylate (6)

Method A. A suspension of 2,2,2-trifluoro-N-(3-cyanophenyl)ethanehydrazonoyl bromide (3, 514 mg, 1.76 mmol) in toluene (5 mL) was treated with ethyl acrylate (352 mg, 373 μL, 3.52 mmol, 2.0 equiv) at 0° C. under $N_2$, and the resulting reaction mixture was treated dropwise with triethylamine (TEA, 267 mg, 377 μL, 2.64 mmol, 1.5 equiv) at 0° C. under $N_2$. The reaction mixture was then gradually warmed to room temperature for 10 h. When the HPLC showed the reaction was deemed complete, the reaction mixture was directly purified by flash column chromatography (SiO₂, 0–20% EtOAc-hexanes gradient elution) to afford ethyl 1-(3-cyano)phenyl-3-trifluoromethylpyrazoline-5-carboxylate (6, 504 mg, 547 mg theoretical, 92%) as the pale yellow oil, which was gradually solidified upon standing at room temperature. For 6: CIMS m/z 312 ($M^++H$, $C_{14}H_{12}F_3N_3O_2$).

Example 9

Method B

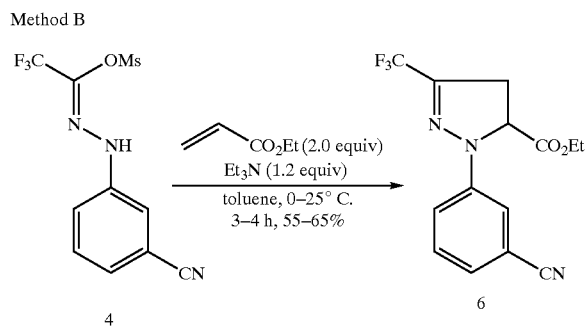

Ethyl 1-(3-cyano)phenyl-3-trifluoromethylpyrazoline-5-carboxylate (6)

Method B. A suspension of 2,2,2-trifluoro-N-(3-cyanophenyl)ethanehydrazonoyl mesylate (4, 31 mg, 0.1 mmol) in toluene (1 mL) was treated with ethyl acrylate (20 mg, 22 μL, 0.2 mmol, 2.0 equiv) at 0° C. under $N_2$, and the resulting reaction mixture was treated dropwise with triethylamine (TEA, 15 mg, 22 μL, 0.15 mmol, 1.5 equiv) at 0° C. under $N_2$. The reaction mixture was then gradually warmed to room temperature for 4 h. When the HPLC showed the reaction was deemed complete, the reaction mixture was directly purified by flash column chromatography (SiO₂, 0–20% EtOAc-hexanes gradient elution) to afford ethyl 1-(3-cyano)phenyl-3-trifluoromethylpyrazoline-5-carboxylate (6, 18 mg, 31.1 mg theoretical, 58%) as the pale yellow oil, which was found to be identical with the material obtained from method A in every comparable aspect and was gradually solidified upon standing at room temperature.

Example 10

Method C

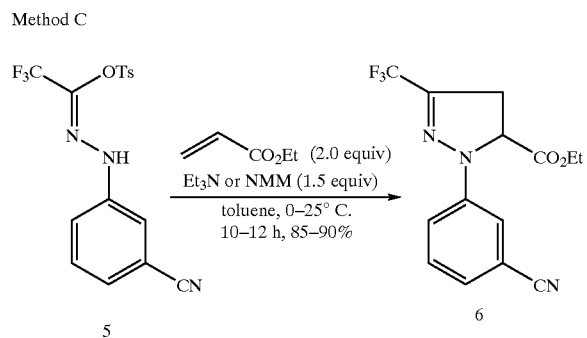

Ethyl 1-(3-cyano)phenyl-3-trifluoromethylpyrazoline-5-carboxylate (6)

Method C. A suspension of 2,2,2-trifluoro-N-(3-cyanophenyl)ethanehydrazonoyl tosylate (5, 79 mg, 0.2 mmol) in toluene (2 mL) was treated with ethyl acrylate (40 mg, 44 μL, 0.4 mmol, 2.0 equiv) at 0° C. under $N_2$, and the resulting reaction mixture was treated dropwise with triethylamine (TEA, 30 mg, 44 μL, 0.3 mmol, 1.5 equiv) at 0° C. under $N_2$. The reaction mixture was then gradually warmed to room temperature for 10 h. When the HPLC showed the reaction was deemed complete, the reaction mixture was directly purified by flash column chromatography (SiO$_2$, 0–20% EtOAc-hexanes gradient elution) to afford ethyl 1-(3-cyano)phenyl-3-trifluoromethylpyrazoline-5-carboxylate (6, 53 mg, 62.2 mg theoretical, 85%) as the pale yellow oil, which was found to be identical with the material obtained from method A and B in every comparable aspect and was gradually solidified upon standing at room temperature.

Example 11

Method D

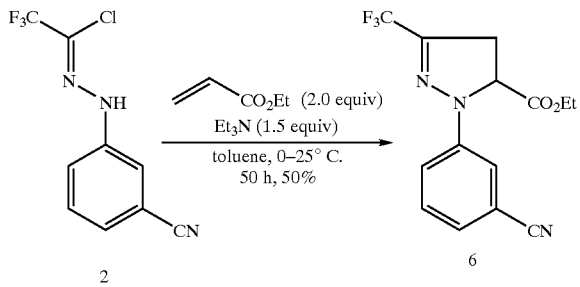

Ethyl 1-(3-cyano)phenyl-3-trifluoromethylpyrazoline-5-carboxylate (6)

Method D. A suspension of 2,2,2-trifluoro-N-(3-cyanophenyl)ethanehydrazonoyl chloride (2, 124 mg, 0.5 mmol) in toluene (2 mL) was treated with ethyl acrylate (100 mg, 108 μL, 1.0 mmol, 2.0 equiv) at 0° C. under N$_2$, and the resulting reaction mixture was treated dropwise with triethylamine (TEA, 76 mg, 108 μL, 0.75 mmol, 1.5 equiv) at 0° C. under N$_2$. The reaction mixture was then gradually warmed to room temperature for 50 h. The HPLC showed that 60% of the starting material (2) was converted into the corresponding cycloaddition product (6) and the rest of the 40% of starting material (2) was still existed in the reaction mixture. The reaction mixture was directly purified by flash column chromatography (SiO$_2$, 0–20% EtOAc-hexanes gradient elution) to afford ethyl 1-(3-cyano)phenyl-3-trifluoromethylpyrazoline-5-carboxylate (6, 78 mg, 156 mg theoretical, 50%) as the pale yellow oil, which was gradually solidified upon standing at room temperature and was found to be identical with the material obtained from method A, B and C detailed above in every comparable aspect.

Example 12

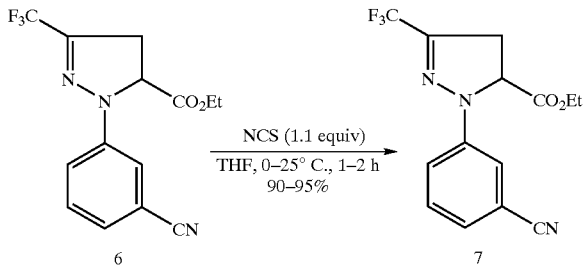

Ethyl 1-(3-cyano)phenyl-3-trifluoromethylpyrazole-5-carboxylate (7)

A solution of ethyl 1-(3-cyano)phenyl-3-trifluoromethylpyrazoline-5-carboxylate (6, 84 mg, 0.27 mmol) in THF (2 mL) was treated with N-chlorosuccinimide (NCS, 40 mg, 0.3 mmol, 1.1 equiv) at 0° C., and the resulting reaction mixture was gradually warmed to room temperature for 1 h. When the HPLC and TLC showed the reaction was deemed complete, the reaction mixture was treated with water (10 mL) and tert-butyl methyl ether (TBME, 10 mL). The two layers were then separated, and the aqueous layer was extracted with TBME (5 mL). The combined organic extracts were washed with water (2×5 mL) and saturated NaCl aqueous solution (10 mL), dried over MgSO$_4$, and concentrated in vacuo. The crude ethyl 1-(3-cyano)phenyl-3-trifluoromethylpyrazole-5-carboxylate (7, 79 mg, 83 mg theoretical, 95%) was obtained as white solids, which was found to be >99% pure by HPLC and can be used in the following hydrolysis reaction without further purification. The analytically pure product (7) was obtained from flash column chromatography (SiO$_2$, 10–30% EtOAc/hexanes gradient elution) purification or recrystalization (EtOAc/hexanes) of the crude 7 obtained above. For 7: CIMS m/z 310 (M$^+$+H, C$_{14}$H$_{10}$F$_3$N$_3$O$_2$).

Example 13

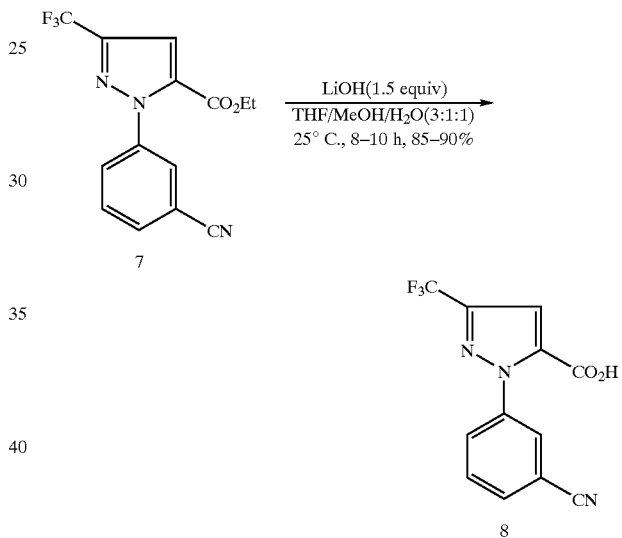

1-(3-Cyano)phenyl-3-trifluoromethylpyrazole-5-carboxylic acid (8)

A solution of ethyl 1-(3-cyano)phenyl-3-trifluoromethylpyrazole-5-carboxylate (7, 800 mg, 2.58 mmol) in THF-MeOH-H$_2$O (3:1:1 v/v, 6 mL) was treated with lithium hydroxide monohydrate (LiOH-H$_2$O, 155 mg, 3.88 mmol, 1.5 equiv) at room temperature, and the resulting reaction mixture was stirred at room temperature for 10 h. When HPLC and TLC showed that the reaction was deemed complete, the solvent was removed in vacuo, and the residue was treated with water (10 mL) and EtOAc (10 mL). The two layers were separated, and the aqueous layer was extracted with EtOAc (5 mL). The combined organic extracts were discarded. The aqueous layer was then acidified with 4 N aqueous HCl to pH 3.0 before being extracted with EtOAc (2×10 mL). The combined organic extracts were washed with H$_2$O (10 mL) and saturated NaCl aqueous solution (10 mL), dried over MgSO$_4$, and concentrated in vacuo. The crude 1-(3-cyano)phenyl-3-trifluoromethylpyrazole-5-carboxylic acid (8, 605 mg, 725 mg theoretical, 84%) was obtained as pale-yellow solids, which was found to be identical with the material obtained from another totally different synthetic method in every comparable aspect and to be >99% pure by HPLC. This crude product can be directly used in the following reaction without further purification. The analytically pure product (8) was obtained from flash column chromatography (SiO$_2$, 10–50% EtOAc/hexanes gradient elution) purification or recrystalization (EtOAc/hexanes) of the crude 8 obtained above. For 8: CIMS m/z 280 (M$^+$–H, C$_{12}$H$_6$F$_3$N$_3$O$_2$).

Example 14

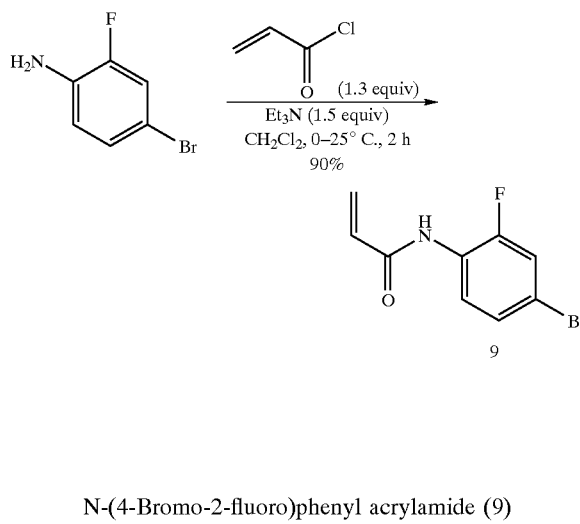

N-(4-Bromo-2-fluoro)phenyl acrylamide (9)

A solution of 4-bromo-2-fluoroaniline (19.0 g, 0.1 mol) in CH$_2$Cl$_2$ (100 mL) was treated with acryloyl chloride (12.35 g, 11.1 mL, 0.13 mmol, 1.3 equiv) at 0° C. under N$_2$, and the resulting mixture was treated dropwise with a solution of triethylamine (TEA, 15.15 g, 21.6 mL, 0.15 mmol, 1.5 equiv) in CH$_2$Cl$_2$ (50 mL) at 0° C. under N$_2$. The reaction mixture was then gradually warmed to room temperature and stirred at room temperature for 2 h before being quenched with water (300 mL). The solids precipitated from the mixture were collected by filtration, washed with water (100 mL) and TBME-hexane (1:2 v/v, 2×100 mL), and dried in vacuo at 40–45° C. for 12 h to afford the first batch of the crude desired N-(4-bromo-2-fluoro)phenyl acrylamide (9, 17.8 g, 24.4 g theoretical, 73%) as grey solids, which was found to be >99% pure by HPLC. The two layers of the filtrates were then separated, and the aqueous layer was extracted with CH$_2$Cl$_2$ (2×100 mL). The combined organic extracts were washed with H$_2$O (100 mL) and saturated aqueous NaCl solution (100 mL), dried over MgSO$_4$, and concentrated in vacuo to afford the second batch of the crude desired product (9, 4.3 g, 24.4 g theoretical, 17.6%; total 90% yield) as off-white solids, which was found to be pure enough to do the following reaction without further purification. The analytically pure product (9) was obtained from direct recrystalization of the crude 9 obtained above from EtOAc/heptanes. For 9: CIMS m/z 242/244 (M$^+$–H, C$_9$H$_7$BrFNO).

Example 15

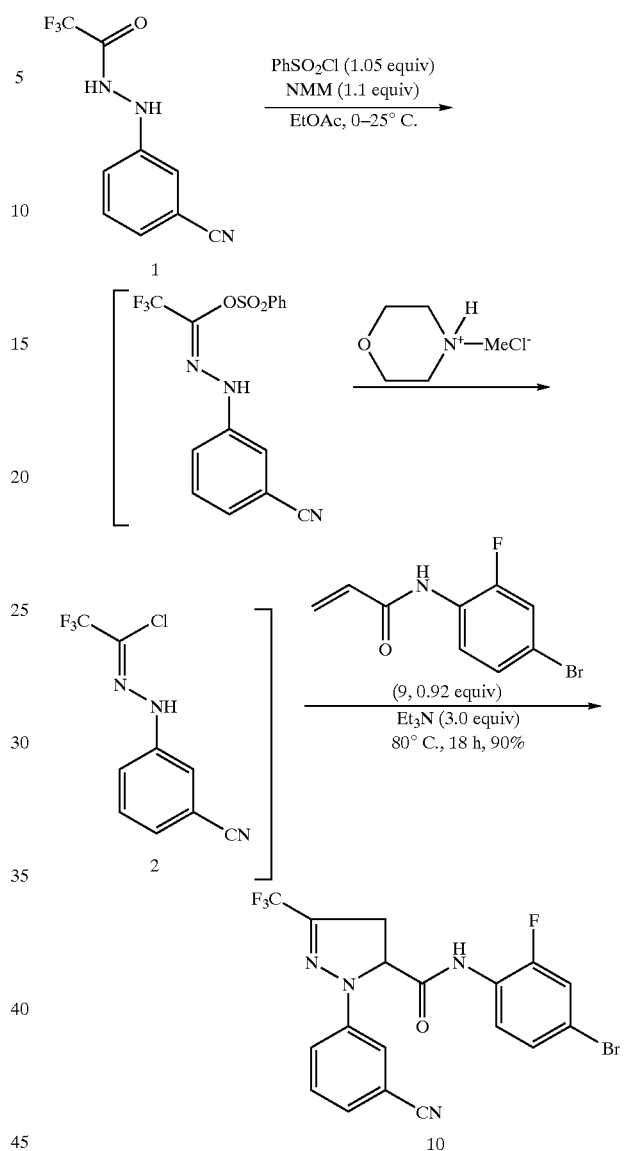

5-(4-Bromo-2-fluoro)phenylcarbamoyl-1-(3-cyano) phenyl-3-trifluoromethyl-pyrazoline (10)

A suspension of 1-(3-cyano)phenyl-2-(trifluoroacetyl) hydrazine (1, 22.9 g, 0.1 mol) in EtOAc (200 mL) was treated with benzenesulfonyl chloride (18.55 g, 13.4 mL, 0.105 mol, 1.05 equiv), and the resulting mixture was treated dropwise with N-methylmorpholine (NMM, 11.11 g, 12.1 mL, 0.11 mol, 1.1 equiv) at 0° C. under N$_2$. The resulting reaction mixture was stirred at 0–5° C. for 30 min before being gradually warmed up to 25° C. for 2 h. When HPLC showed that the transformation of starting material into the corresponding 2,2,2-trifluoro-N-(3-cyanophenyl) ethanehydrazonoyl chloride (2) was deemed complete, the reaction mixture was treated with N-(4-bromo-2-fluoro) phenyl acrylamide (9, 22.4 g, 0.092 mol, 0.92 equiv) and triethylamine (30.3 g, 43.3 mL, 0.3 mol, 3.0 equiv) at 25° C. under N$_2$. The resulting reaction mixture was subsequently warmed up to gentle reflux (80° C.) for 18 h. When HPLC showed that the cycloaddition reaction was deemed complete, the reaction mixture was cooled down to room temperature before being treated with H₂O (200 mL) and EtOAc (200 mL). The mixture was stirred at room temperature for 30 min. The two layers were separated. The aqueous layer was extracted with EtOAc (100 mL). The combined organic extracts were washed with H₂O (2×200 mL) and saturated NaCl aqueous solution (200 mL), dried over MgSO₄, and concentrated in vacuo to leave a slurry of the crude cycloaddition product (10) in about 100 mL of EtOAc. The residual slurry was then treated with heptanes (400 mL), and the resulting mixture was stirred at room temperature for 1 h before being cooled down to 0° C. for an additional 2 h. The solids were collected by filtration, washed with heptanes (2×100 mL), and dried in vacuo at 40–45° C. for 12 h to afford the crude desired 5-(4-bromo-2-fluoro) phenylcarbamoyl-1-(3-cyano)phenyl-3-trifluoromethyl-pyrazoline (10, 37.9 g, 41.86 g theoretical, 90.5%), which was found to be pure enough to do the following reaction without further purification. The analytically pure product (10) was obtained from recrystalization of the crude product obtained above from EtOAc-heptanes. For 10: CIMS m/z 453/455 (M⁺–H, C₁₈H₁₁F₄BrN₄O).

Example 16

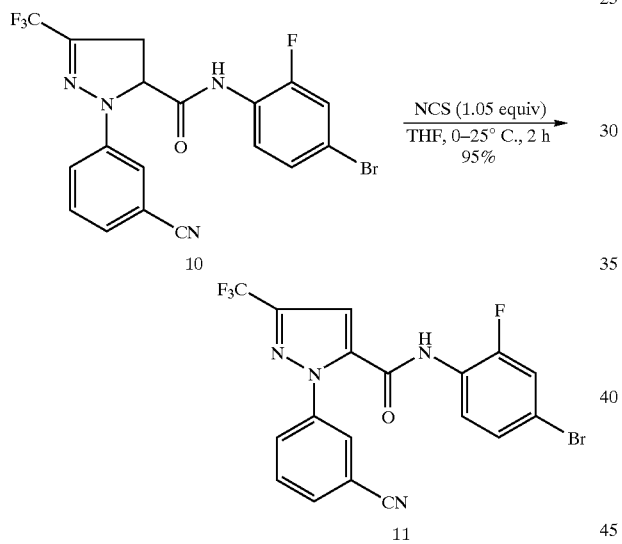

5-(4-Bromo-2-fluoro)phenylcarbamoyl-1-(3-cyano) phenyl-3-trifluoromethyl-pyrazole (11)

A suspension of 5-(4-bromo-2-fluoro)phenylcarbamoyl-1-(3-cyano)phenyl-3-trifluoromethylpyrazoline (10, 10.6 g, 23.3 mmol) in THF (100 mL) was treated with N-chlorosuccinimide (NCS, 3.17 g, 23.8 mmol, 1.05 equiv) at 0–5° C., and the resulting reaction mixture was gradually warmed to room temperature for 2 h. When the HPLC and TLC showed the reaction was deemed complete, the reaction mixture was treated with water (100 mL) and THF (100 mL). The two layers were separated, and the aqueous layer was extracted with EtOAc (100 mL). The combined organic extracts were washed with water (2×100 mL) and saturated NaCl aqueous solution (100 mL), dried over MgSO₄, and concentrated in vacuo. The residual slurry of the crude product in THF/EtOAc (about 50 mL) was treated with heptanes (200 mL), and the resulting mixture was stirred at room temperature for 1 h. The solids were collected by filtration, washed with heptanes (2×50 mL), and dried in vacuo at 40–45° C. for 12 h to afford the crude 5-(4-bromo-2-fluoro)phenylcarbamoyl-1-(3-cyano)phenyl-3-trifluoromethyl-pyrazole (11, 9.99 g, 10.55 g theoretical, 95%), which was found to be pure enough to do the following reaction without further purification. The analytically pure product (11) was obtained from recrystalization of the crude product obtained above from EtOAc/heptanes. For 11: CIMS m/z 451/453 (M⁺–H, C₁₈H₉F₄BrN₄O).

Example 17

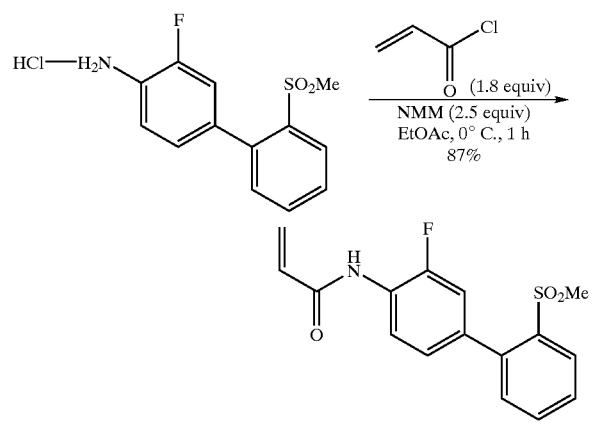

N-[2-Fluoro-4-(2-methylsulfonyl)phenyl]phenyl acrylamide (12)

A solution of 2-fluoro-4-(2-methylsulfonyl)phenylanaline hydrochloride salt (60.3 g, 0.2 mol) in EtOAc (400 mL) was treated with NMM (50.5 g, 54.9 mL, 0.5 mol. 2.5 equiv) at 0° C. under N₂, and the resulting mixture was treated dropwise with a solution of acryloyl chloride (32.58 g, 28.6 mL, 0.13 mmol, 1.8 equiv) at 0° C. under N₂. The reaction mixture was then stired at 0–5° C. for 1 h before being quenched with water (400 mL). The solids precipitated from the mixture were collected by filtration, washed with water (100 mL) and EtOAc-hexane (1:3 v/v, 2×100 mL), and dried in vacuo at 40–45° C. for 12 h to afford the first batch of the crude N-[2-fluoro-4-(2-methylsulfonyl)phenyl]phenyl acrylamide (12, 32.6 g, 63.8 g theoretical, 51.1%) as white powder, which was found to be >99.5% pure by HPLC. The two layers of the filtrates were then separated, and the aqueous layer was extracted with EtOAc (150 mL). The combined organic extracts were washed with H₂O (2×100 mL) and saturated NaCl aqueous solution (100 mL), dried over MgSO₄, and concentrated in vacuo. The residual slurry (about 50 mL) was then treated with heptanes (400 mL). The mixture was stirred at room temperature for 30 min before being filtrated. The collected solids were washed with heptanes (2×50 mL), and dried in vacuo at 40–45° C. for 12 h to afford the second batch of the crude N-[2-fluoro-4-(2-methylsulfonyl)phenyl)]phenyl acrylamide (12, 23.2 g, 63.8 g theoretical, 36.4%) as white powder, which was found to be >99.5% pure by HPLC. The crude product (55.8 g, 63.8 g theoretical, total 87.5% yield) was found to be pure enough to do the following reaction without further purification. The analytically pure product (12) was obtained from recrystalization of the crude product obtained above from EtOAc/heptanes. For 12: CIMS m/z 318 (M⁺–H, C₁₆H₁₄FNO₃S).

Example 18

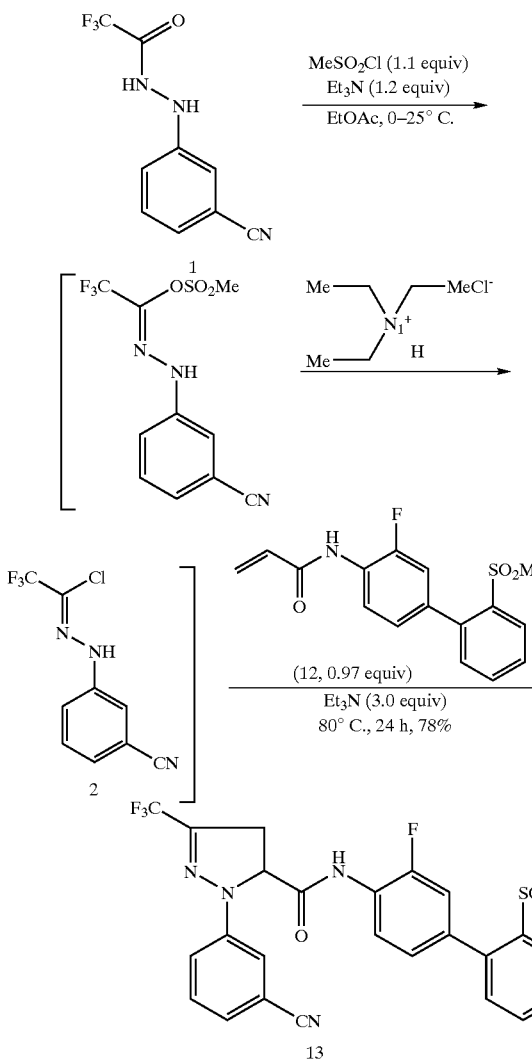

1-(3-Cyano)phenyl-5-[2-fluoro-4-(2-methylsulfonyl)phenyl]phenylcarbamoyl-3-trifluoromethylpyrazoline (13)

A suspension of 1-(3-cyano)phenyl-$^2$-(trifluoroacetyl)hydrazine (1, 6.87 g, 0.03 mol) in EtOAc (60 mL) was treated with methanesulfonyl chloride (3.78 g, 2.55 mL, 0.033 mol, 1.1 equiv), and the resulting mixture was treated dropwise with triethylamine (TEA, 3.64 g, 5.2 mL, 0.036 mol, 1.2 equiv) at 0–5° C. under $N_2$. The resulting reaction mixture was stirred at 0–5° C. for 30 min before being gradually warmed up to 25° C. for 2 h. When HPLC showed that the transformation of starting material (1) into the corresponding 2,2,2-trifluoro-N-(3-cyanophenyl)ethanehydrazonoyl chloride (2) was deemed complete, the reaction mixture was treated with N-[2-fluoro-4-(2-methylsulfonyl)phenyl]phenyl acrylamide (10, 9.28 g, 0.0291 mol, 0.97 equiv) and triethylamine (TEA, 9.09 g, 13 mL, 0.09 mol, 3.0 equiv) at 25° C. under $N_2$. The resulting reaction mixture was subsequently warmed up to gentle reflux (80° C.) for 24 h. When HPLC showed that the cycloaddition reaction was deemed complete, the reaction mixture was cooled down to room temperature before being treated with $H_2O$ (100 mL) and EtOAc (100 mL). The mixture was stirred at room temperature for 30 min. The two layers were separated. The aqueous layer was extracted with EtOAc (50 mL). The combined organic extracts were washed with $H_2O$ (2×50 mL) and saturated NaCl aqueous solution (50 mL), dried over $MgSO_4$, and concentrated in vacuo to leave a slurry of the crude cycloaddition product (13) in about 40 mL of EtOAc. The residual slurry was then treated with heptanes (200 mL), and the resulting mixture was stirred at room temperature for 1 h before being cooled down to 0° C. for an additional 2 h. The solids were collected by filtration, washed with heptanes (2×50 mL), and dried in vacuo at 40–45° C. for 12 h to afford the crude desired 1-(3-cyano)phenyl-5-[2-fluoro-4-(2-(methsulfonyl)phenyl]phenylcarbamoyl-3-trifluoromethylpyrazoline (13, 12.40 g, 15.9 g theoretical, 78%), which was found to be pure enough to do the following reaction without further purification. The analytically pure product (13) was obtained from recrystalization of the crude product obtained above from EtOAc/heptanes. For 13: CIMS m/z 529 ($M^+$–H, $C_{25}H_{18}F_4N_4O_3S$).

Example 19

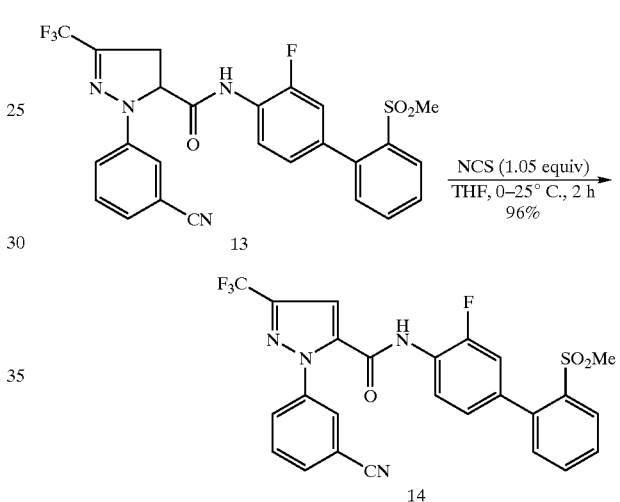

1-(3-Cyano)phenyl-5-[2-fluoro-4-(2-methylsulfonyl)phenyl]phenylcarbamoyl-3-trifluoromethylpyrazole (14)

A suspention of 1-(3-cyano)phenyl-5-[2-fluoro-4-(2-methylsulfonyl)phenyl]phenylcarbamoyl-3-trifluoromethylpyrazoline (13, 8.8 g, 16.6 mmol) in THF (60 mL) was treated with N-chlorosuccinimide (NCS, 2.33 g, 17.4 mmol, 1.05 equiv) at 0–5° C., and the resulting reaction mixture was stirred at 0–5° C. for 30 min before being warmed to 25° C. for 2 h. When HPLC and TLC showed that the reaction was deemed complete, most of the solvent (THF) was removed in vacuo. The residue was then treated with $H_2O$ (100 mL) and EtOAc (200 mL), and the resulting solution was stirred at room temperature for 10 min. The two layers were separated, and the aqueous layer was extracted with EtOAc (50 mL). The combined organic extracts were washed with $H_2O$ (2×100 mL) and saturated aqueous NaCl (50 mL), dried over $MgSO_4$, and concentrated in vacuo. The residual slurry of the crude product (14) in THF/EtOAc (40 mL) was titrated with heptanes (200 mL) to precipitate the crude desired oxidation product (14). The solids were collected by filtration, washed with heptanes (2×50 mL), and dried at 40–45° C. for 12 h to afford the crude desired 1-(3-cyano)phenyl-5-[2-fluoro-4-(2-methylsulfonyl)phenyl]phenylcarbamoyl-3-trifluoromethylpyrazole (14, 8.4 g, 8.76 g theoretical, 95.9%), which was found to be pure enough to do the following reaction without further purification. The analytically pure product (14) was obtained from recrystalization of the crude product obtained above from EtOAc/heptanes. For 14: CIMS m/z 527 ($M^+$–H, $C_{25}H_{16}F_4N_4O_3S$).

Example 20

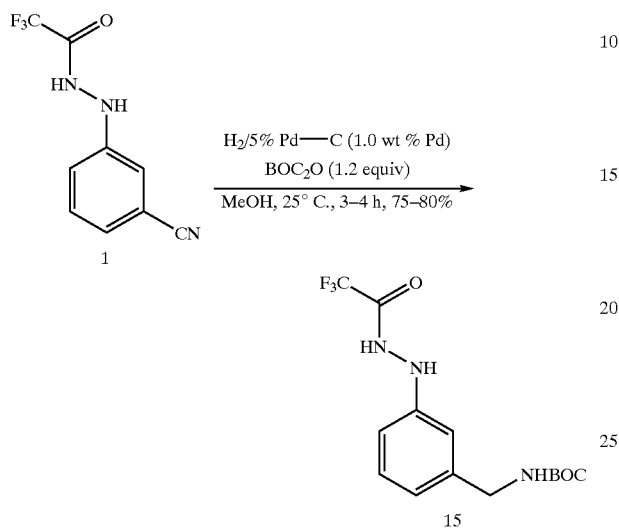

A solution of 1-(3-cyano)phenyl-2-(trifluoroacetyl) hydrazine (1, 1.20 Kg, 5.24 mol) and di-tert-butyl dicarbonate ($Boc_2O$, 1.37 Kg, 6.29 mol, 1.2 equiv) in methanol (10 L) was introduced into a 5-gallon pressure reactor (Parr model SS 1996) containing 5% palladium on carbon (50% wet catalyst, 0.42 Kg, 1.0 wet %) at 25° C. under $N_2$. The resulting reaction mixture was then degassed with a steady hydrogen stream for three times before being hydrogenated under 50–55 psig hydrogen pressure at ambient temperature for 3–4 h. When the hydrogenation reaction was deemed complete, the reaction mixture was treated with methanol (1.0 L) and charcoal (100 g). The resulting mixture was stirred at room temperature for 10 min before being filtered through a Celite® (200 g, pre-washed with methanol) bed. The Celite®/charcoal bed was washed with methanol (2×500 mL). The filtrates were then concentrated in vacuo, and the residual concentrated solution (4 L) was treated with toluene (4 L). The resulting slurry was stirred at room temperature for 12 h. The sollids were collected by filtration, washed with toluene (2×1.0 L), and dried at 60° C. in vacuo to constant weight (20 h) to afford the crude desired 1-[3-((N-tert-butoxy)carbonyl)aminomethyl]phenyl-2-(trifluoroacetyl)-hydrazine (15, 1.365 Kg, 1.745 Kg theoretical, 77%) as white powder, which was found to be >95% pure and was used in the following reaction without further purification. The analytically pure material (15) was obtained from recrystalization of the crude material obtained above from EtOAc-heptanes. For 15: CIMS m/z 332 ($M^+$–H, $C_{14}H_{18}F_3N_3O_3$).

Example 21

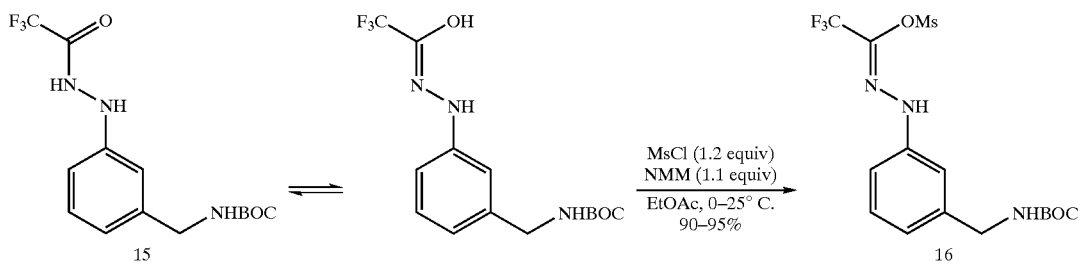

1-[3-((N-tert-Butoxy)carbonyl)aminomethyl]phenyl-2-(trifluoroacetyl)hydrazine (15)

2,2,2-Trifluoro-N-[3-((N-tert-butoxy)carbonyl) aminomethyl]phenylethane-hydrazonoyl mesylate (16)

A solution 1-[3-((N-tert-butoxy)carbonyl)aminomethyl]-phenyl-2-(trifluoroacetyl) hydrazine (15, 3.33 g, 0.01 mol) in EtOAc (20 mL) was treated with methanesulfonyl chloride (1.38 g, 0.93 mL, 0.012 mol, 1.2 equiv), and the resulting solution was added dropwise with a solution of N-methylmorpholine (NMM, 1.11 g, 1.2 ML, 0.011 mol, 1.1 equiv) in EtOAc (20 ML) at 0–5° C. under $N_2$. The resulting reaction mixture was stirred at 0–5° C. for 30 min before being gradually warmed up to 25° C. for 12 h. When HPLC and TLC showed that the reaction was deemed complete, the reaction mixture was treated with $H_2O$ (30 mL). The two layers were separated, and the aqueous layer was extracted with EtOAc (20 mL). The combined organic extracts were washed with $H_2O$ (2×20 mL) and saturated NaCl aqueous solution (20 mL), dried over $MgSO_4$, and concentrated in vacuo. The residual oily crude 2,2,2-trifluoro-N-[3-((N-tert-butoxy)carbonyl)aminomethyl]phenylethane-hydrazonoyl mesylate (16, 3.86 g, 4.11 g theoretical, 94%) was found to be >97% pure by HPLC, which can be used in the following reaction without further purification. The analytically pure product (16) was obtained by flash column chromatography (SiO$_2$, 10–30% EtOAc-hexanes gradient elution) purification of the crude product obtained above. For 16: CIMS m/z 410 (M$^+$–H, C$_{15}$H$_{20}$F$_3$N$_3$O$_5$S).

Example 22

Method A

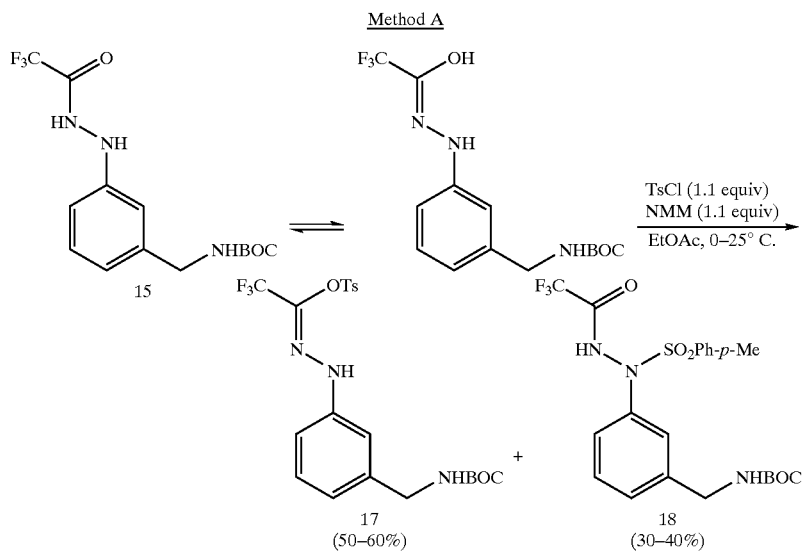

layers were separated, and the aqueous layer was extracted with EtOAc (30 mL). The combined organic extracts were washed with H$_2$O (2×20 mL) and saturated NaCl aqueous solution (20 mL), dried over MgSO$_4$, and concentrated in vacuo. The residual EtOAc slurry (15 mL) was then titrated with hexanes (50 mL), and the resulting mixture was stirred at 25° C. for 30 min to precipitate the crude desired product (17). The white solids were collected by filtration, washed with heptanes (2×30 mL), and dried at 40–45° C. in vacuo for 12 h to afford the crude desired 2,2,2-trifluoro-N-[3-((N-tert-butoxy)carbonyl)-aminomethyl]phenylethanehydrazonoyl tosylate (17, 2.63 g, 4.87 g theoretical, 54%), which was found to be pure enough

2,2,2-Trifluoro-N-[3-((N-tert-butoxy)carbonyl) aminomethyl]phenylethane-hydrazonoyl tosylate (17)

Method A. A solution 1-[3-((N-tert-butoxy)carbonyl)-aminomethyl]phenyl-2-(trifluoroacetyl)hydrazine (15, 3.33 g, 0.01 mol) in EtOAc (20 mL) was treated with p-toluenesulfonyl chloride (2.11 g, 0.011 mol, 1.1 equiv) at 0–5° C. under N$_2$, and the resulting solution was added dropwise with a solution of N-methylmorpholine (NMM, 1.11 g, 1.2 mL, 0.011 mol, 1.1 equiv) in EtOAc (10 mL) at 0–5° C. under N$_2$. The resulting reaction mixture was stirred at 0–5° C. for 30 min before being gradually warmed up to 25° C. for 4 h. When HPLC and TLC showed that the reaction was deemed complete, the reaction mixture was treated with H$_2$O (50 mL) and EtOAc (50 mL). The two (>95%) by HPLC to do the following reaction without further purification. The analytically pure product (17) was obtained from recrystalization of the crude product obtained above from EtOAc/heptanes. For 17: CIMS m/z 486 (M$^+$–H, C$_{21}$H$_{24}$F$_3$N$_3$O$_5$S). The filtrates were then evaporated in vacuo, and the residue was purified by flash column chromatography (SiO$_2$, 10–30 % EtOAc-hexanes gradient elution) to afford the corresponding undesired sulfamide (18, 1.32 g, 4.87 g theoretical, 27.1%) as yellow oil, which solidified upon standing at room temperature in vacuo. For 18: CIMS m/z 486 (M$^+$–H, C$_{21}$H$_{24}$F$_3$N$_3$O$_5$S).

Example 23

Method B

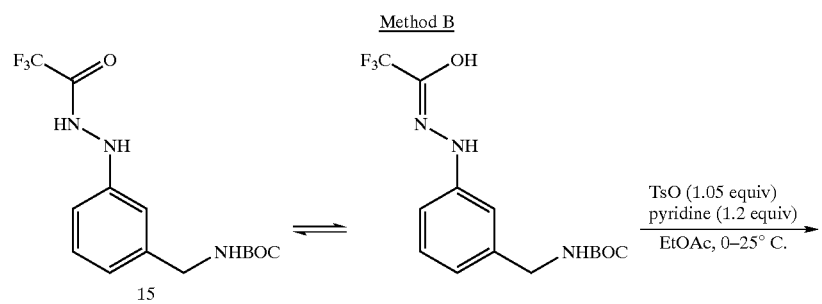

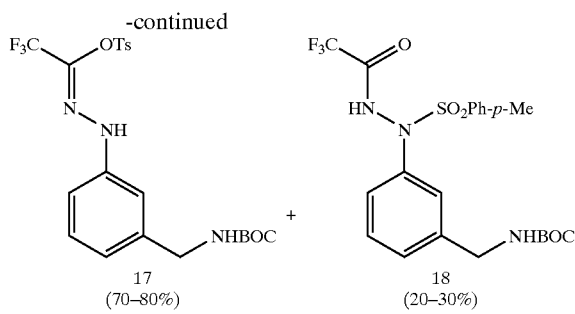

2,2,2-Trifluoro-N-[3-((N-tert-butoxy)carbonyl) aminomethyl]phenylethane-hydrazonoyl tosylate (17)

Method B. A solution 1-[3-((N-tert-butoxy)carbonyl)-aminomethyl]phenyl-2-(trifluoroacetyl)hydrazine (15, 1.332 g, 4.0 mmol) in EtOAc (8 mL) was treated with p-toluenesulfonyl anhydride (1.37 g, 4.2 mmol, 1.05 equiv) at 0–5° C. under $N_2$, and the resulting solution was treated with pyridine (379 mg, 0.39 mL, 4.8 mmol, 1.2 equiv) at 0–5° C. under $N_2$. The resulting reaction mixture was stirred at 0–5° C. for 10 min before being gradually warmed up to 25° C. for 20 min. When HPLC and TLC showed that the reaction was deemed complete, the reaction mixture was treated with $H_2O$ (10 mL) and EtOAc (20 mL). The two layers were separated, and the aqueous layer was extracted with EtOAc (10 mL). The combined organic extracts were washed with $H_2O$ (2×10 mL) and saturated NaCl aqueous solution (10 mL), dried over $MgSO_4$, and concentrated in vacuo. The residue was then purified by flash column chromatography ($SiO_2$, 10–30% EtOAc-hexanes gradient elution) to afford the desired 2,2,2-trifluoro-N-[3-((N-tert-butoxy)carbonyl)-aminomethyl]phenylethanehydrazonoyl tosylate (17, 1.47 g, 1.95 g theoretical, 75.3%), which was found to be identical as the material obtained from method A detailed above in every comparable aspect, and the corresponding undesired sulfamide (18, 0.308 g, 1.95 g theoretical, 15.8%) as yellow oil, which was also found to be identical as the material obtained from method A detailed above in every comparable aspect.

Example 24

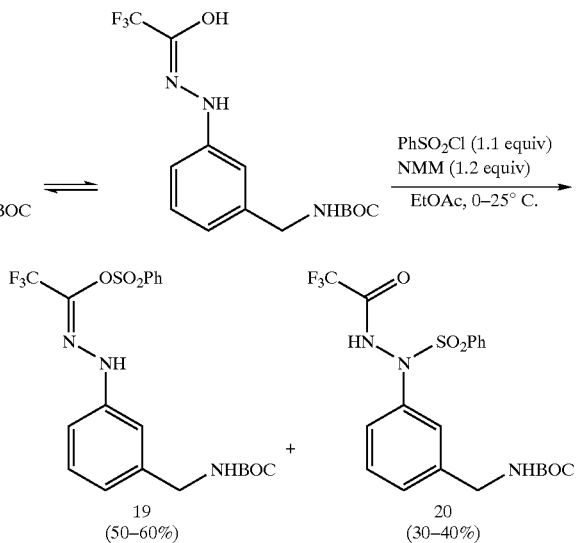

2,2,2-Trifluoro-N-[3-((N-tert-butoxy)carbonyl) aminomethyl]phenylethane-hydrazonoyl benzenesulfonate (19)

A solution of 1-[3-((N-tert-butoxy)carbonyl)-aminomethyl]phenyl-2-(trifluoroacetyl)hydrazine (15, 1.665 g, 5.0 mmol) in ethyl acetate (10 mL) was treated with phenylsulfonyl chloride (971 mg, 702 mL, 5.5 mmol, 1.1 equiv) at room temperature under $N_2$, and the resulting reaction mixture was cooled to 0–5° C. before being treated with N-methylmorpholine (NMM, 606 mg, 659 mL, 1.2 equiv) at 0–5° C. under $N_2$. The reaction mixture was stirred at 0–5° C. for 1 h before being gradually warmed to room temperature for 6 h. When HPLC and TLC showed that the reaction was deemed complete, the reaction mixture was treated with $H_2O$ (20 mL) and EtOAc (20 mL). The two layers were separated, and the aqueous layer was extracted with EtOAc (20 mL). The combined organic extracts were washed with $H_2O$ (2×20 mL) and saturated NaCl aqueous solution (20 mL), dried over $MgSO_4$, and concentrated in vacuo. The residue was purified by flash column chromatography ($SiO_2$, 10–30% EtOAc-hexanes gradient elution) to afford 2,2,2-trifluoro-N-[3-((N-tert-butoxy)carbonyl)

amino-methyl]phenylethanehydrazonoyl benzenesulfonate (19, 1.36 g, 2.365 g theoretical, 57.5%) as white solids and 1-[3-((N-tert-butoxy)carbonyl)aminomethyl]phenyl-1-phenylsulfonyl-2-(trifluoroacetyl)hydrazine (20, 733 mg, 2.365 g theoretical, 31% ) as pale-yellow oil, which solidified upon standing in vacuo at room temperature. For 19: CIMS m/z 472 (M$^+$–H, $C_{20}H_{22}F_3N_3O_5S$); For 20: CIMS m/z 472 (M$^+$–H, $C_{20}H_{22}F_3N_3O_5S$).

Example 25

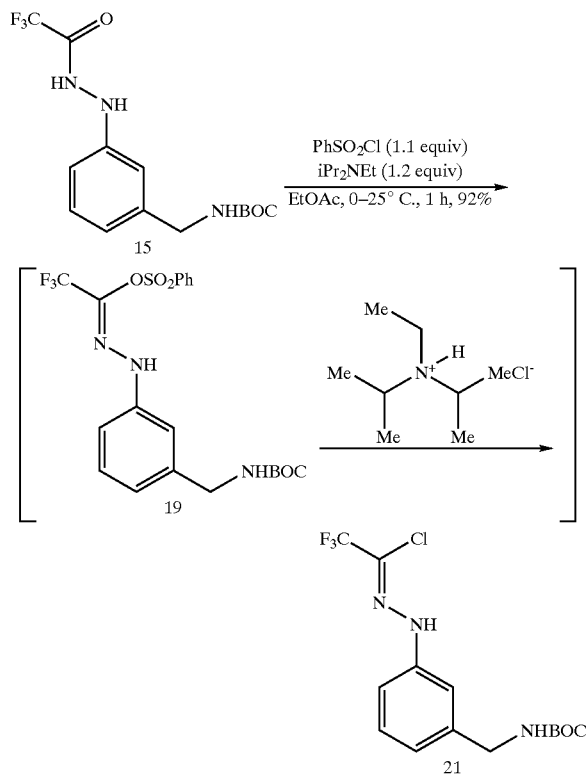

2,2,2-Trifluoro-N-[3-((N-tert-butoxy)carbonyl) aminomethyl]phenylethane-hydrazonoyl chloride (21)

A solution of 1-[3-((N-tert-butoxy)carbonyl) aminomethyl]-phenyl-2-(trifluoroacetyl)hydrazine (15, 3.33 g, 10.0 mmol) in ethyl acetate (20 mL) was treated with phenylsulfonyl chloride (1.94 g, 1.40 mL, 11.0 mmol, 1.1 equiv) at room temperature under $N_2$, and the resulting reaction mixture was cooled to 0–5° C. before being treated dropwise with N,N-diisopropylethylamine (Hunig's base, 1.55 g, 2.09 mL, 12.0 mmol, 1.2 equiv) at 0–5° C. under $N_2$. The reaction mixture was stirred at 0–5° C. for 1 h. When HPLC and TLC showed that the reaction was deemed complete, the reaction mixture was treated with $H_2O$ (30 mL) and EtOAc (20 mL). The two layers were separated, and the aqueous layer was extracted with EtOAc (20 mL). The combined organic extracts were washed with $H_2O$ (2×20 mL) and saturated NaCl aqueous solution (20 mL), dried over $MgSO_4$, and concentrated in vacuo. The residue was purified by flash column chromatography ($SiO_2$, 10–20% EtOAc-hexanes gradient elution) to afford 2,2,2-trifluoro-N-[3-((N-tert-butoxy)carbonyl)amino-methyl] phenylethanehydrazonoyl chloride (21, 3.24 g, 3.51 g theoretical, 92.3%) as white solids. For 21: CIMS m/z 350/352 (M$^+$–H, $C_{14}H_{17}F_3NO_3O_2$).

Example 26

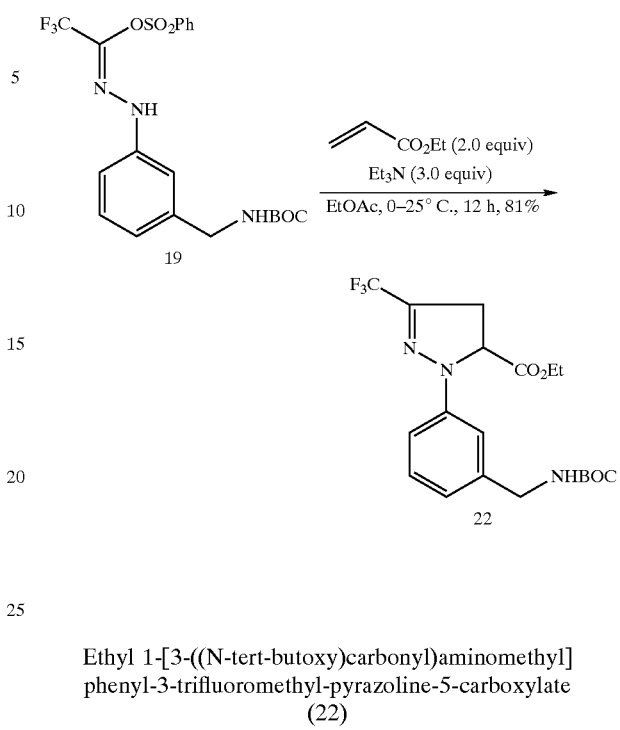

Ethyl 1-[3-((N-tert-butoxy)carbonyl)aminomethyl] phenyl-3-trifluoromethyl-pyrazoline-5-carboxylate (22)

A solution of 2,2,2-trifluoro-N-[3-((N-tert-butoxy)-carbonyl)aminomethyl]phenylethanehydrazonoyl benzene-sulfonate (19, 170 mg, 0.36 mmol) in ethyl acetate (3 mL) was treated with ethyl acrylate (72 mg, 78 μL, 0.72 mmol, 2.0 equiv) at room temperature under $N_2$, and the resulting reaction mixture was cooled down to 0–5° C. before being treated with triethylamine (TEA, 109 mg, 156 μL, 1.08 mmol, 3.0 equiv) at 0–5° C. under $N_2$. The reaction mixture was stirred at 0–5° C. for 30 min before being gradually warmed up to room temperature for 12 h. When HPLC and TLC showed that the reaction was deemed complete, the solvent were removed in vacuo, and the residue was directly purified by flash column chromatography ($SiO_2$, 10–20% EtOAc-hexanes gradient elution) to afford ethyl 1-[3-((N-tert-butoxy)carbonyl)amino-methyl]phenyl-3-trifluoromethylpyrazoline-5-carboxylate (22, 336 mg, 415 mg theoretical, 81%) as pale-yellow oil, which solidified upon standing in vacuo at room temperature. For 22: CIMS m/z 414 (M$^+$–H, $C_{19}H_{24}F_3N_3O_4$).

Example 27

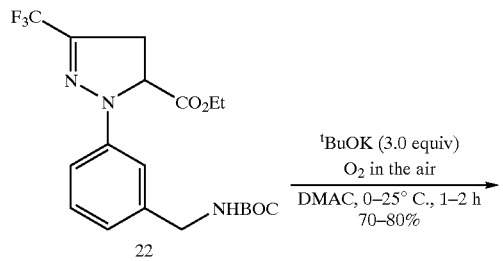

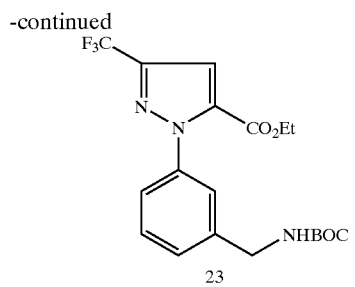

Ethyl 1-[3-((N-tert-butoxy)carbonyl)aminomethyl] phenyl-3-trifluoromethyl pyrazole-5-carboxylate (23)

A solution of ethyl 1-[3-((N-tert-butoxy)carbonyl)aminomethyl]phenyl-3-trifluoromethylpyrazoline-5-carboxylate (22, 115 mg, 0.28 mmol) in DMF (1.0 mL) was added dropwise to a solution of potassium tert-butoxide (94 mg, 0.84 mmol, 3.0 equiv) at 0–5° C. A steady stream of air was then bubbled into the reaction mixture for 30 min at 0–50C. When HPLC and TLC showed the reaction was deemed complete, the reaction mixture was treated with $H_2O$ (5 mL) and EtOAc (10 mL). The two layers were separated, and the aqueous layer was extracted with EtOAc (5 mL). The combined organic extracts were washed with H20 (2×5 ML) and saturated NaCl aqueous solution (5 mL), dried over $MgSO_4$, and concentrated in vacuo. The residue was purified by flash column chromatography ($SiO_2$, 10–20 % EtOAc-hexanes gradient elution) to afford the desired ethyl 1-[3-((N-tert-butoxy)carbonyl)aminomethyl]phenyl-3-trifluoromethylpyrazole-5-carboxylate (23, 83 mg, 115 mg theoretical, 72%) as pale-yellow oil, which solidified at room temperature in vacuo. For 23: CIMS m/z 412 ($M^+$–H, $C_{19}H_{22}F_3N_3O_4$).

Example 28

1-[3-((N-tert-Butoxy)carbonyl)aminomethyl]phenyl-5-[2-fluoro-4-(2-methyl-sulfonyl)phenyl]phenylcarbamoyl-3-trifluoromethylpyrazoline (24)

A suspension of 1-[3-(N-tert-butoxy)carbonyl)aminomethyl]phenyl-2-(trifluoroacetyl)hydrazine (15, 33.3 g, 0.1 mol) in EtOAc (200 mL) was treated with benzenesulfonyl chloride (18.55 g, 13.4 mL, 0.105 mol, 1.05 equiv) at 0–5° C. under $N_2$, and the resulting mixture was treated dropwise with N,N-diisopropylethylamine (Hunig's base, 14.22 g, 19.2 mL, 0.11 mol, 1.1 equiv) at 0–5° C. under $N_2$. The resulting reaction mixture was stirred at 0–5° C. for 45 min. When HPLC and TLC showed that the transformation of starting material (15) into the corresponding 2,2,2-trifluoro-N-[3-((N-tert-butoxy)carbonyl)aminomethyl]phenylethane-hydrazonoyl chloride (21) was deemed complete, the reaction mixture was treated with N-[2-fluoro-4-(2-methylsulfonyl)phenyl]phenyl acrylamide (12, 30.94 g, 0.092 mol, 0.97 equiv) and triethylamine (TEA, 30.3 g, 43.3 mL, 0.3 mol, 3.0 equiv) at 25° C. under $N_2$. The resulting reaction mixture was subsequently warmed up to gentle reflux (80 ° C.) for 24 h. When HPLC showed that the cycloaddition reaction was deemed complete, the reaction mixture was cooled down to room temperature before being treated with $H_2O$ (200 mL) and EtOAc (200 mL). The mixture was stirred at room temperature for 30 min. The two layers were separated. The aqueous layer was extracted with EtOAc (100 mL). The combined organic extracts were washed with $H_2O$ (2×200 mL) and saturated NaCl aqueous solution (200 mL), dried over $MgSO_4$, and concentrated in vacuo to leave a slurry of the crude cycloaddition product (24) in about 100 mL of EtOAc. The residual slurry was then treated with heptanes (500 mL), and the resulting mixture was stirred at room temperature for 1 h before being cooled down to 0° C. for an additional 2 h. The solids were collected by filtration, washed with heptanes (2×100 mL), and dried in vacuo at 40–45° C. for 12 h to afford the crude desired cycloaddition product (24, 51.2 g, 61.5 g theoretical, 83.3%). The crude cycloaddition product 24 (>98% HPLC area pure) was then directly recrystalized from EtOAc/

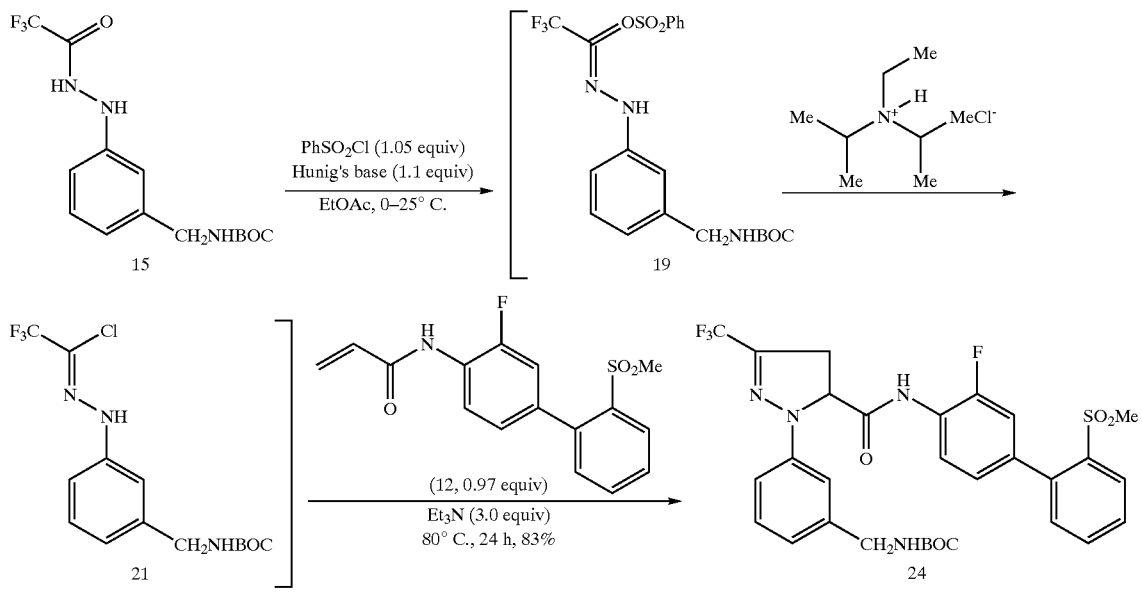

Example 29

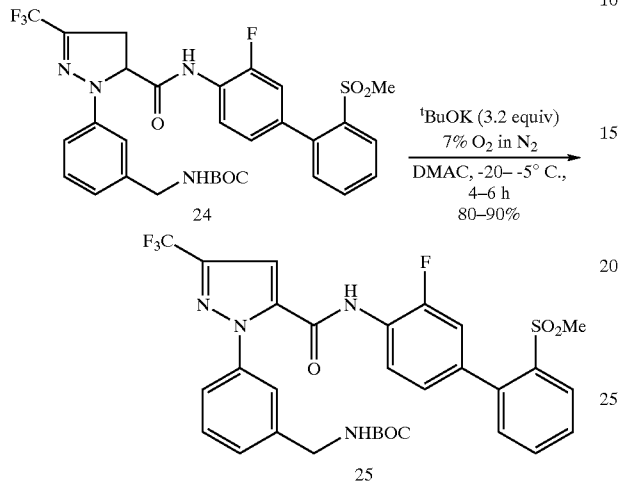

1-[3-((N-tert-Butoxy)carbonyl)aminomethyl]phenyl-5-[2-fluoro-4-(2-methyl-sulfonyl)phenyl]phenylcarbamoyl-3-trifluoromethylpyrazole (25)

A solution of 1-[3-((N-tert-butoxy)carbonyl) aminomethyl]phenyl-5-[2-fluoro-4-(2-methylsulfonyl) phenyl]-phenylcarbamoyl-2-trifluoromethylpyrazoline (24, 5.0 g, 7.9 mmol) in DMF (25 mL) was added dropwise to a solution of potassium tert-butoxide (2.7 g, 24.5 mmol, 3.1 equiv) in DMF (15 ml) at −20° C. A steady stream of 7% of $O_2$ in $N_2$ was then bubbled into the reaction mixture for 6 h at −20–25° C. When HPLC and TLC showed the reaction was deemed complete, the reaction mixture was treated with 1.0 N aqueous citric acid solution (250 mL) at 0–5° C. The resulting mixture was then stirred at room temperature for 12 h to precipitate the crude desired oxidation product. The solids were collected by filtration, washed with heptanes (2×40 mL), and dried at 40–45° C. in vacuo for 12 h to afford the crude 1-[3-((N-tert-butoxy)carbonyl)aminomethyl] phenyl-5-[2-fluoro-4-(2-methylsulfonyl)phenyl] phenylcarbamoyl-3-trifluoromethylpyrazole (25, 4.3 g, 5.0 g theoretical, 86%) as off-white crystals, which was found to be >95% pure by HPLC. The filtrates were then extracted with EtOAc (2×50 mL). The combined organic extracts were washed with $H_2O$ (2×20 mL) and saturated NaCl aqueous solution (20 mL), dried over $MgSO_4$, and concentrated in vacuo to afford an additional amount of the crude 25 (200 mg, 5.0 g theoretical, 4%; total 90% yield) as yellow solids. The crude 25 was directly used in the following reaction without further purification and the analytically pure 25 was obtained from the recrystalization of the crude product obtained above from EtOAc-heptanes. For 25: CIMS m/z 631 ($M^+$–H, $C_{30}H_{28}F_4N_4O_5S$).

Example 30

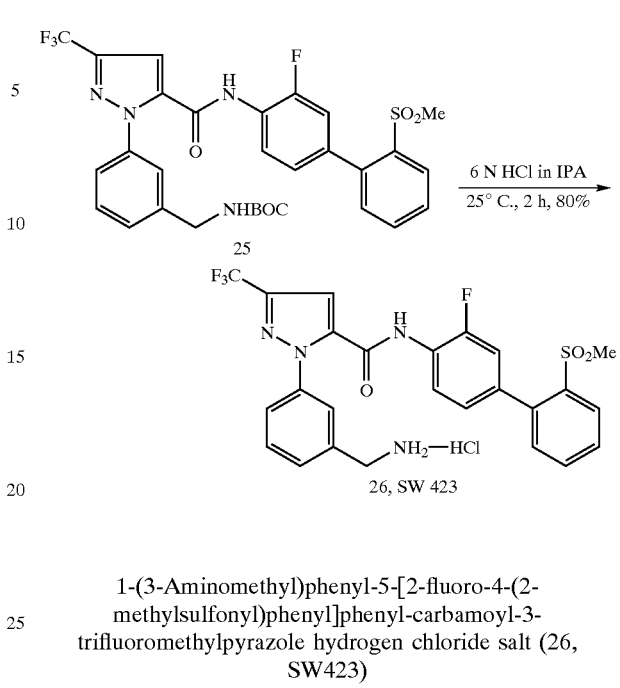

1-(3-Aminomethyl)phenyl-5-[2-fluoro-4-(2-methylsulfonyl)phenyl]phenyl-carbamoyl-3-trifluoromethylpyrazole hydrogen chloride salt (26, SW423)

A suspension of 1-[3-((N-tert-butoxy)carbonyl) aminomethyl]phenyl-5-[2-fluoro-4-(2-methylsulfonyl) phenyl]phenylcarbamoyl-3-trifluoromethylpyrazole (25, 13.7 g, 21.7 mmol) in 5–6 N HCl in isopropyl alcohol (IPA, 120 ML) was stirred at room temperature for 2 h. When HPLC and TLC showed that the reaction was deemed complete, the solvent was removed in vacuo. The residue was dissolved in MeOH (50 mL) and ethyl acetate (50 mL) at gentle reflux (60–65° C.), and the resulting hot solution was then treated with charcoal (activated carbon, 1.5 g), and the resulting mixture was refluxed for an additional 1 h. Filtration of the mixture through a Celite® bed, and the Celite® bed was washed with MeOH/EtOAc (1:1 v/v, 20 mL). The filtrates were then stirred at room temperature for 1 h before being cooled down to 0–5° C. for an additional 1 h. The white solids were collected by filtration, washed with EtOAc (30 mL), and dried in vacuo at 40–45° C. for 12 h to afford the desired 1-(3-aminomethyl)phenyl-5-[2-fluoro-4-(2-methyl-sulfonyl)phenyl]phenylcarbamoyl-3-trifluoromethylpyrazole hydrogen chloride salt (26, 9.87 g, 12.35 g theoretical, 80%) as white crystals, which was found to be >99.5% pure by HPLC and to be identical as the material obtained from another totally different synthetic approach in every comparable aspect.

Example 31

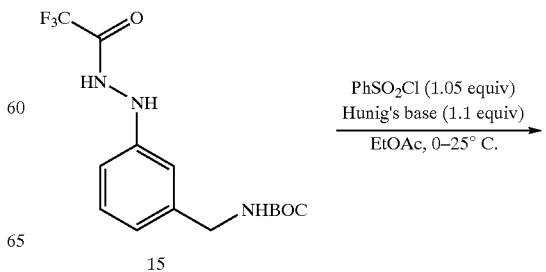

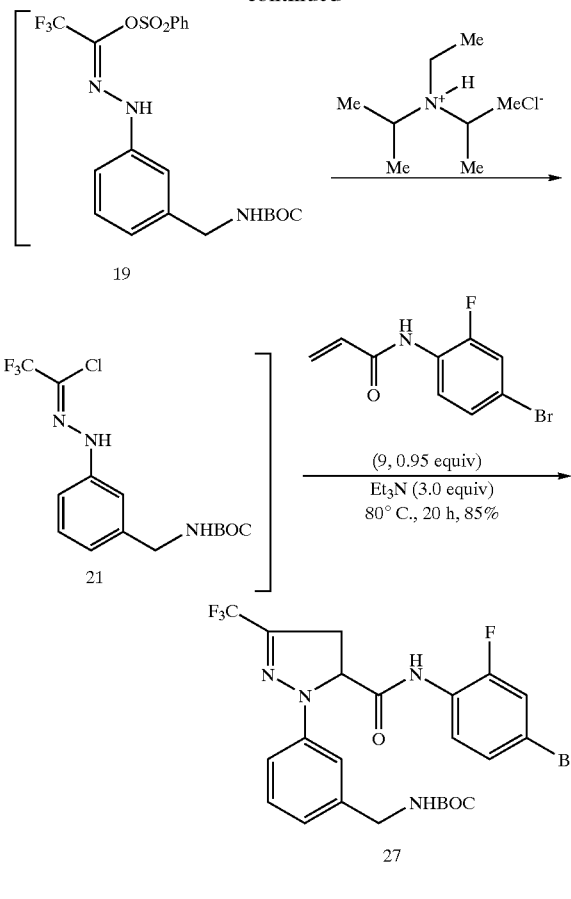

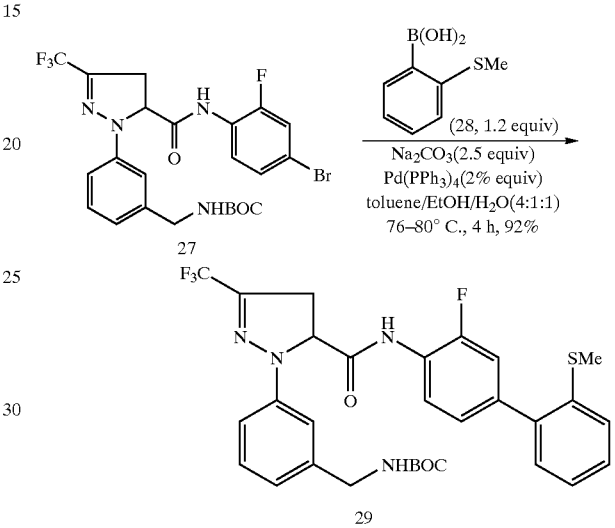

1-[3-((N-tert-Butoxy)carbonyl)aminomethyl]phenyl-5-(2-fluoro-4-bromo)phenyl-carbamoyl-3-trifluoromethylpyrazoline (27)

A suspension of 1-[3-(N-tert-butoxy)carbonyl) aminomethyl]phenyl-2-(trifluoroacetyl)hydrazine (15, 33.3 g, 0.1 mol) in EtOAc (200 mL) was treated with benzenesulfonyl chloride (18.55 g, 13.4 mL, 0.105 mol, 1.05 equiv), and the resulting mixture was treated dropwise with N,N-diisopropylethylamine (Hunig's base, 14.22 g, 19.2 mL, 0.11 mQl, 1.1 equiv) at 0° C. under $N_2$. The resulting reaction mixture was stirred at 0–5° C. for 45 min. When HPLC and TLC showed that the transformation of starting material (15) into the corresponding 2,2,2-trifluoro-N-[3-((N-tert-butoxy)carbonyl)aminomethyl] phenylethanehydrazonoyl chloride (21) was deemed complete, the reaction mixture was treated with N-(2-fluoro-4-bromo)phenyl acrylamide (9, 23.18 g, 0.095 mol, 0.95 equiv) and triethylamine (30.3 g, 43.3 mL, 0.3 mol, 3.0 equiv) at 25° C. under $N_2$. The resulting reaction mixture was subsequently warmed up to gentle reflux (80° C.) for 20 h. When HPLC showed that the cycloaddition reaction was deemed complete, the reaction mixture was cooled down to room temperature before being treated with $H_2O$ (200 mL) and EtOAc (100 mL). The mixture was stirred at room temperature for 30 min. The two layers were separated. The aqueous layer was extracted with EtOAc (100 mL). The combined organic extracts were washed with $H_2O$ (2×200 mL) and saturated NaCl aqueous solution (200 mL), dried over $MgSO_4$, and concentrated in vacuo to leave a slurry of the crude cycloaddition product (27) in about 70 mL of EtOAc. The residual slurry was then treated with heptanes (300 mL), and the resulting mixture was stirred at room temperature for 1 h before being cooled down to 0° C. for an additional 1 h. The solids were collected by filtration, washed with heptanes (2×50 mL), and dried in vacuo at 40–45° C. for 12 h to afford the crude desired cycloaddition product (27, 44.9 g, 53.1 g theoretical, 84.6%). The crude cycloaddition product 27 was found to be pure enough (>99% HPLC area pure) to do the following reaction without further purification. The analytical pure material was obtained from the recrystalization of the crude 27 from EtOAc/heptanes. For 27: CIMS m/z 558/560 ($M^+$-H, $C_{23}H_{23}F_4BrN_4O_3$).

Example 32

1-[3-((N-tert-Butoxy)carbonyl)aminomethyl]phenyl-5-[2-fluoro-4-(2-methylthio)-phenyl] phenylcarbamoyl-3-trifluoromethylpyrazoline (29)

A suspension of 1-[3-((N-tert-butoxy)carbonyl) aminomethyl]phenyl-5-(2-fluoro-4-bromo)-phenylcarbamoyl-3-trifluoromethylpyrazoline (27, 2.795 g, 5.0 mmol) in toluene (20 mL) was treated with 2-methylthiophenylboronic acid (28, 1.002 g, 6.0 mmol, 1.2 equiv), sodium carbonate ($Na_2CO_3$, 1. 33 g. 12.5 mmol, 2.5 equiv), ethanol (EtoH, 5 mL), and water (5 mL) at room temperature. The resulting mixture was degassed three times under $N_2$ before being treated with $Pd(PPh_3)_4$ (116 mg, 0.1 mmol, 2% equiv). The resulting reaction mixture was subsequently degassed three times again under $N_2$ before being warmed up to gentle reflux (76–77° C.) for 4 h. When HPLC and TLC showed that the reaction was deemed complete, the reaction mixture was cooled down to room temperature and treated with EtOAc (40 mL) and water (40 mL). The mixture was stirred at room temperature for 10 min, and the two layers were separated. The aqueous layer was extracted with EtOAc (20 mL). The combined organic extracts were washed with $H_2O$ (2×20 mL) and saturated NaCl aqueous solution (20 mL), dried over $MgSO_4$, and concentrated in vacuo. The residual solution of the crude coupling product (29) in EtOAc/toluene (20 mL) was titrated with heptanes (80 mL), and the resulting mixture was stirred at room temperature for 1 h before being cooled down to 0–5° C. for an additional 1 h. The solids were collected by filtration and washed with heptanes (2×30 mL) , dried in vacuo at 40–45° C. for 12 h to afford the crude desired 1-[3-((N-tert-butoxy)

carbonyl)aminomethyl]phenyl-5-[2-fluoro-4-(2-methylthio) phenyl]phenylcarbamoyl-3-trifluoromethylpyrazoline (29, 2.78 g, 3.01 g theoretical, 92.4%), which was found to be >99% pure by HPLC and can be used in the following reaction without further purification. The analytical pure product (29) was obtained from recrystalization of the crude 29 from EtOAc/heptanes. For 29: CIMS m/z 601 (M$^+$–H, $C_{30}H_{30}F_4N_4O_3S$).

Example 33

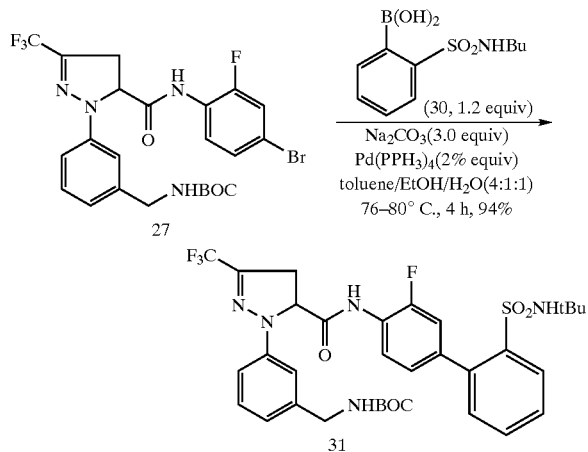

1-[3-((N-tert-Butoxy)carbonyl)aminomethyl]phenyl-5-[2-fluoro-4-(2-(N-tert-butylamino)sulfonyl) phenyl]phenylcarbamoyl-3-trifluoromethylpyrazoline (31)

A suspension of 1-[3-((N-tert-butoxy)carbonyl) aminomethyl]phenyl-5-(2-fluoro-4-bromo)-phenylcarbamoyl-3-trifluoromethylpyrazoline (27, 1.118 g, 2.0 mmol) in toluene (8 mL) was treated with 2-[(N-tert-butylamino)sulfonyl]phenylboronic acid (30, 617 mg, 2.4 mmol, 1.2 equiv), sodium carbonate ($Na_2CO_3$, 636 mg. 6.0 mmol, 3.0 equiv), ethanol (EtOH, 2 mL), and water (2 mL) at room temperature. The resulting mixture was degassed three times under $N_2$ before being treated with $Pd(PPh_3)_4$ (46 mg, 0.04 mmol, 2% equiv). The resulting reaction mixture was subsequently degassed three times again under $N_2$ before being warmed up to gentle reflux (76–77° C.) for 4 h. When HPLC and TLC showed that the reaction was deemed complete, the reaction mixture was cooled down to room temperature and treated with EtOAc (20 mL) and water (20 mL). The mixture was stirred at room temperature for 10 min, and the two layers were separated. The aqueous layer was extracted with EtOAc (10 mL). The combined organic extracts were washed with $H_2O$ (2×10 mL) and saturated NaCl aqueous solution (10 mL), dried over $MgSO_4$, and concentrated in vacuo. The residue was purified by flash column chromatography ($SiO_2$, 5–20% EtOAc-hexanes gradient elution) to afford the pure desired 1-[3-((N-tert-butoxy)carbonyl)amino-methyl]phenyl-5-[2-fluoro-4-(2-((N-tert-butyl-amino)sulfonyl)phenyl] phenylcarbamoyl-3-trifluoromethylpyrazoline (31, 1.30 g, 1.382 g theoretical, 94.1%) as white solids. For 31: CIMS m/z 690 (M$^+$–H, $C_{33}H_{37}F_4N_5O_5S$).

Example 34

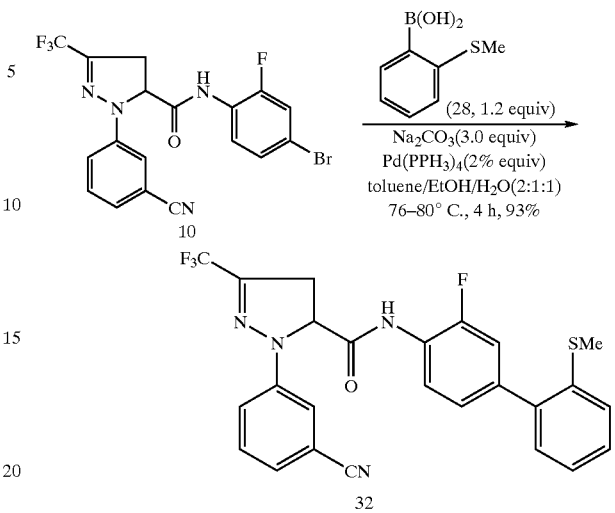

1-(3-Cyano)phenyl-5-[2-fluoro-4-(2-methylthio) phenyl]phenylcarbamoyl-3-trifluoromethylpyrazoline (32)

A suspension of 1-(3-cyano)phenyl-5-(2-fluoro-4-bromo) phenylcarbamoyl-3-trifluoromethylpyrazoline (10, 9.10 g, 20.0 mmol) in toluene (60 mL) was treated with 2-methylthiophenylboronic acid (28, 4.0 g, 24.0 mmol, 1.2 equiv), sodium carbonate ($Na_2CO_3$, 6.36 g. 60.0 mmol, 3.0 equiv), ethanol (EtOH, 30 mL), and water (30 mL) at room temperature. The resulting mixture was degassed three times under $N_2$ before being treated with $Pd(PPh_3)_4$ (462.4 mg, 0.4 mmol, 2% equiv). The resulting reaction mixture was subsequently degassed three times again under $N_2$ before being warmed up to gentle reflux (76–77° C.) for 4 h. When HPLC and TLC showed that the reaction was deemed complete, the reaction mixture was cooled down to room temperature and treated with water (100 mL). The mixture was stirred at room temperature for 2 h. The solids precipitated from the mixture were collected by filtration, washed with $H_2O$ (2×50 mL) and 25% EtOAc-heptanes (2×50 mL), and dried in vacuo at 40–45° C. for 12 h to afford the crude desired 1-(3-cyano)phenyl-5-[2-fluoro-4-(2-methylthio)phenyl] phenylcarbamoyl-3-trifluoromethylpyrazoline (32, 9.21 g, 9.96 g theoretical, 92.5%), which was found to be >99% pure by HPLC and was used in the following reaction without further purification. The analytically pure product (32) was obtained from recrystalization of the crude material obtained above from EtOAc-heptanes. For 32: CIMS m/z 497 (M$^+$–H, $C_{25}H_{18}F_4N_4OS$).

Example 35

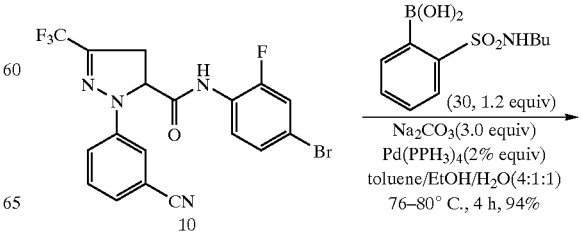

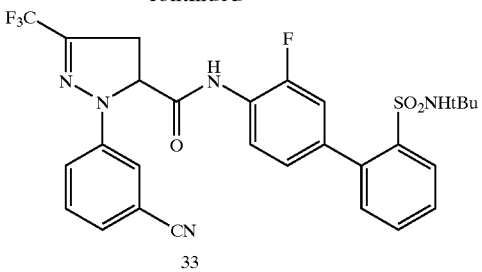

1-(3-Cyano)phenyl-5-[2-fluoro-4-(2-(N-tert-butylamino)sulfonyl)phenyl]phenyl-carbamoyl-3-trifluoromethylpyrazoline (33)

A suspension of 1-(3-cyano)phenyl-5-(2-fluoro-4-bromo)phenylcarbamoyl-3-trifluoromethylpyrazoline (10, 910 mg, 2.0 mmol) in toluene (8 mL) was treated with 2-[(N-tert-butylamino)sulfonyl]phenylboronic acid (30, 617 mg, 2.4 mmol, 1.2 equiv), sodium carbonate (Na$_2$CO$_3$, 636 mg, 6.0 mmol, 3.0 equiv), ethanol (EtOH, 2 mL), and water (2 mL) at room temperature. The resulting mixture was degassed three times under N$_2$ before being treated with Pd(PPh$_3$)$_4$ (46 mg, 0.04 mmol, 2% equiv). The resulting reaction mixture was subsequently degassed three times again under N$_2$ before being warmed up to gentle reflux (76–77° C.) for 4 h. When HPLC showed that the reaction was deemed complete, the reaction mixture was cooled down to room temperature and treated with EtOAc (20 mL) and water (20 mL). The mixture was stirred at room temperature for 10 min. The two layers were separated, and the aqueous layer was extracted with EtOAc (10 mL). The combined organic extracts were washed with H$_2$O (2×10 mL) and saturated NaCl aqueous solution (10 mL), dried over MgSO$_4$, and concentrated in vacuo. The residue was then purified by flash column chromatography (Sio$_2$, 5–20% EtOAc-heptanes gradient elution) to afford the desired 1-(3-cyano)phenyl-5-[2-fluoro-4-(2-(N-tert-butylamino)sulfonyl)phenyl]phenylcarbamoyl-3-trifluoromethylpyrazoline (33, 1.1. g, 1.174 g theoretical, 93.6%) as white solids. For 33: CIMS m/z 586 (M$^+$–H, C$_{28}$H$_{25}$F$_4$N$_5$O$_3$S).

Example 36

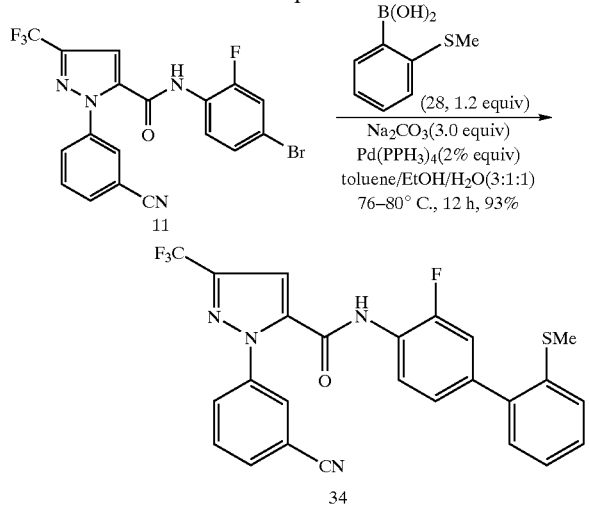

1-(3-Cyano)phenyl-5-[2-fluoro-4-(2-methylthio)phenyl]phenylcarbamoyl-3-trifluoromethylpyrazole (34)

A suspension of 1-(3-cyano)phenyl-5-(2-fluoro-4-bromo)-phenylcarbamoyl-3-trifluoromethylpyrazole (11, 4.53 g, 10.0 mmol) in toluene (20 mL) was treated with 2-(methylthio)phenylboronic acid (28, 2.0 g, 12.0 mmol, 1.2 equiv), sodium carbonate (Na$_2$CO$_3$, 3.18 g. 30.0 mmol, 3.0 equiv), ethanol (EtOH, 10 mL), and water (10 mL) at room temperature. The resulting mixture was degassed three times under N$_2$ before being treated with Pd(PPh$_3$)$_4$ (231.2 mg, 0.2 mmol, 2% equiv). The resulting reaction mixture was subsequently degassed three times again under N$_2$ before being warmed up to gentle reflux (76–77 ° C.) for 12 h. When HPLC and TLC showed that the reaction was deemed complete, the reaction mixture was cooled down to room temperature and treated with water (100 mL). The mixture was stirred at room temperature for 1 h. The solids precipitated from the mixture were collected by filtration and washed with H$_2$O (2×50 mL) and 25% EtOAc-heptanes (2×50 mL), dried in vacuo at 40–45C for 12 h to afford the crude desired 1-(3-cyano)phenyl-5-[2-fluoro-4-(2-methylthio)phenyl]phenylcarbamoyl-3-trifluoromethylpyrazole (34, 3.3 g, 4.96 g theoretical, 66.5%), which was found to be >99% pure by HPLC and can be used in the following reaction without further purification. The two layers of the filtrate were separated, and the aqueous layer was extracted with EtOAc (30 mL). The combined organic extracts were washed with H$_2$O (2×20 mL) and saturated NaCl aqueous solution (20 mL), dried over MgSO$_4$, and concentrated in vacuo. The residual slurry (15 mL) was titrated with heptanes (100 mL), and the resulting mixture was stirred at room temperature for an additional 30 min. The solids were collected by filtration and washed with 25% EtOAc-heptanes (2×20 mL), dried in vacuo at 40–45° C. for 12 h to afford the second batch of the crude desired coupling product (34, 1.30 g, 4.96 g theoretical, 26.2%), which was found to be >99% pure by HPLC and can be used in the following reaction without further purification. The analytically pure product (34) was obtained from recrystallization of the crude material obtained above from EtOAc/heptanes. For 34: CIMS m/z 495 (M$^+$–H, C$_{25}$H$_{16}$F$_4$N$_4$OS).

Example 37

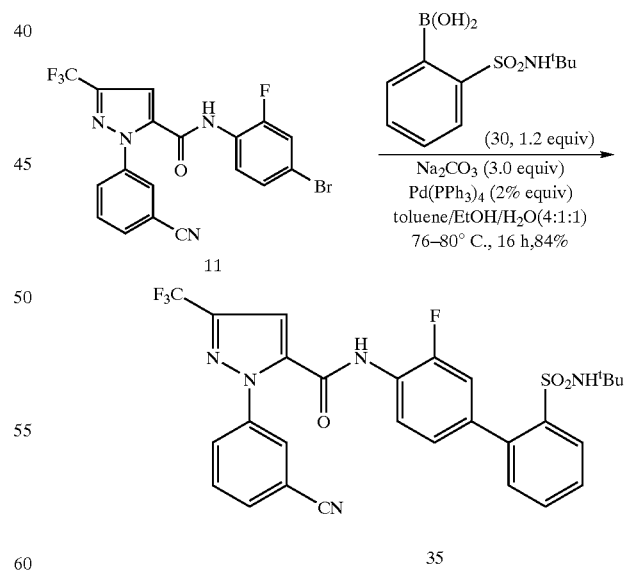

1-(3-Cyano)phenyl-5-[2-fluoro-4-(2-(N-tert-butylamino)sulfonyl)phenyl]phenyl-carbamoyl-3-trifluoromethylpyrazole (35)

A suspension of 1-(3-cyano)phenyl-5-(2-fluoro-4-bromo)phenylcarbamoyl-3-trifluoromethylpyrazole (11, 906 mg, 2.0 mmol) in toluene (8 mL) was treated with 2-[(tert-butylamino)sulfonyl]phenylboronic acid (30, 617 mg, 2.4 mmol, 1.2 equiv), sodium carbonate (Na$_2$CO$_3$, 636 mg. 6.0 mmol, 3.0 equiv), ethanol (EtOH, 2 mL), and water (2 mL) at room temperature. The resulting mixture was degassed three times under N$_2$ before being treated with Pd(PPh$_3$)$_4$ (46 mg, 0.04 mmol, 2% equiv). The resulting reaction mixture was subsequently degassed three times again under N$_2$ before being warmed up to gentle reflux (76–77° C.) for .16 h. When HPLC and TLC showed that the reaction was deemed complete, the reaction mixture was cooled down to room temperature and treated with water (20 mL) and EtOAc (20 mL). The mixture was stirred at room temperature for 10 min. The two layers were separated, and the aqueous layer was extracted with EtOAc (10 mL). The combined organic extracts were washed with H$_2$O (2×10 mL) and saturated aqueous NaCl solution (10 mL), dried over MgSO$_4$, and concentrated in vacuo. The residue was purified by flash column chromatography (SiO$_2$, 5–25% EtOAc-hexanes gradient elution) to afford the desired 1-(3-cyano)phenyl-5-[2-fluoro-4-(2-(N-tert-butylamino) sulfonyl)phenyl]phenyl-carbamoyl-3-trifluoromethyl-pyrazole (35, 984 mg, 1.17 g theoretical, 84.1%) as colorless oil, which was solidified at room temperature in vacuo. For 35: CIMS m/z 584 (M$^+$–H, C$_{28}$H$_{23}$F$_4$N$_5$O$_3$S).

Example 38

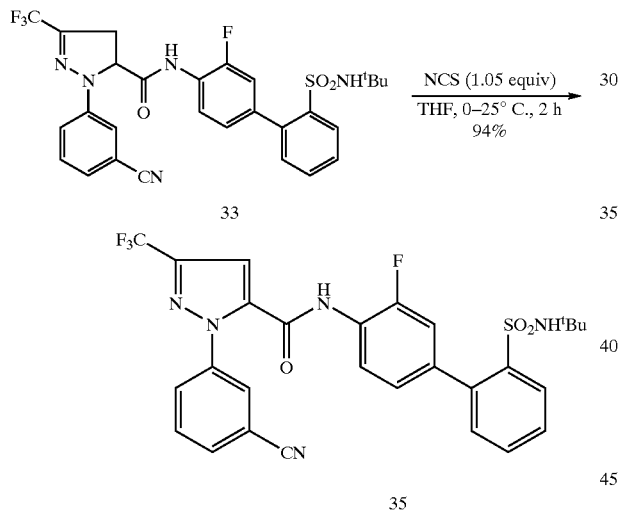

1-(3-Cyano)phenyl-5-[2-fluoro-4-(2-(N-tert-butylamino)sulfonyl)phenyl]phenyl-carbamoyl-3-trifluoromethylpyrazole (35)

A solution of 1-(3-cyano)phenyl-5-[2-fluoro-4-(2-(N-tert-butylamino)sulfonyl)phenyl]phenyl-carbamoyl-3-trifluoromethyl-pyrazoline (33, 585 mg, 1.0 mmol) in THF (4 mL) was treated with N-chlorosuccinimide (NCS, 140 mg, 1.05 mmol, 1.05 equiv) at 0–5° C., and the resulting reaction mixture was stirred at 0–5° C. for 10 min before being gradually warmed up to room temperature for 2 h. When TLC and HPLC showed that the reaction was deemed complete, the reaction mixture was treated with EtOAc (10 mL) and water (10 mL). The two layers were separated, and the aqueous layer was extracted with EtOAc (10 mL). The combined organic extracts were washed with H$_2$O (2×10 mL) and saturated NaCl aqueous solution (10 mL), dried over MgSO$_4$, and concentrated in vacuo. The residual pale-yellow oil was solidified at room temperature in vacuo to afford the crude desired 1-(3-cyano)phenyl-5-[2-fluoro-4-(2-(N-tert-butyl-amino)sulfonyl)phenyl]phenylcarbamoyl-3-trifluoromethylpyrazole(35, 550 mg, 583 mg theoretical, 94%), which was found to be >99% pure by HPLC and to be identical as the material obtained from the different synthetic approach detailed above in every comparable aspect.

Example 39

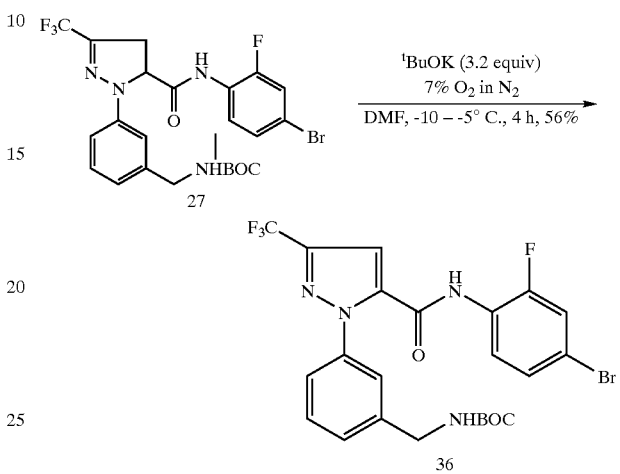

1-[3-((N-tert-Butoxy)carbonyl)aminomethyl]phenyl-5-(2-fluoro-4-bromo)phenyl-carbamoyl-3-trifluoromethylpyrazole (36)

A solution of 1-[3-((N-tert-butoxy)carbonyl) aminomethyl]phenyl-5-(2-fluoro-4-bromo) phenylcarbamoyl-3-trifluoro-methyl-pyrazoline (27, 1.0 g, 1.8 mmol) in DMF (5 mL) was added dropwise to a solution of potassium tert-butoxide (645 mg, 5.75 mmol, 3.2 equiv) in DMF (5 mL) at –10° C. A steady stream of 7% of O$_2$ in N$_2$ was then bubbled into the reaction mixture at –10–5° C. for 4 h. When HPLC and TLC showed the reaction was deemed complete, the reaction mixture was treated with 1.0 N aqueous citric acid solution (20 mL) at 0–5° C. The resulting solution was then extracted with EtOAc (3×20 mL). The combined organic extracts were washed with H$_2$O (2×10 mL) and saturated NaCl aqueous solution (10 mL), dried over MgSO$_4$, and concentrated in vacuo. The residue was then purified by flash column chromatography (SiO$_2$, 10–20 EtOAc-hexanes gradient elution) to afford the desired 1-[3-((N-tert-butoxy)carbonyl)aminomethyl]phenyl-5-(2-fluoro-4-bromo)phenyl-carbamoyl-3-trifluoromethylpyrazole (36, 560 mg, 1.0 g theoretical, 56%) as white solids. For 36: CIMS m/z 556/558 (M$^+$–H, C$_{23}$H$_{21}$F$_4$BrN$_4$O$_3$).

Example 40

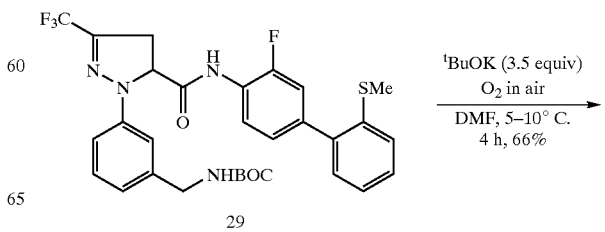

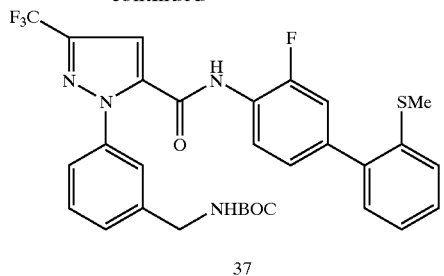

37

1-[3-((N-tert-Butoxy)carbonyl)aminomethyl]phenyl-5-[2-fluoro-4-(2-methylthio)-phenyl]phenylcarbamoyl-3-trifluoromethylpyrozole (37)

A solution of 1-[3-((N-tert-butoxy)carbonyl)aminomethyl]phenyl-5-[2-fluoro-4-(2-methylthio)phenyl]phenyl-carbamoyl-3-trifluoromethylpyrazoline (29, 637 mg, 1.1 mmol) in DMF (5 mL) was added dropwise to a solution of potassium tert-butoxide (416 mg, 3.72 mmol, 3.5 equiv) in DMF (5 ml) at 0–5° C. A steady stream of 7% of $O_2$ in $N_2$ was then bubbled into the reaction mixture at 0–10° C. for 2.5 h. When HPLC and TLC showed the reaction was deemed complete, the reaction mixture was treated with 1.0 N aqueous citric acid solution (20 mL) at 0–10° C. The resulting solution was then extracted with tert-butyl methyl ether (TBME, 3×20 mL). The combined organic extracts were washed with $H_2O$ (2×10 mL) and saturated NaCl aqueous solution (10 mL), dried over $MgSO_4$, and concentrated in vacuo. The residue was then purified by flash column chromatography ($SiO_2$, 10–20% EtOAc-hexanes gradient elution) to afford the crude 1-[3-((N-tert-butoxy)carbonyl)aminomethyl]phenyl-5-[2-fluoro-4-(2-methylthio)phenyl]phenyl-carbamoyl-3-trifluoromethylpyrazole (37, 420 mg, 637 mg theoretical, 66%) as white solids. For 37: CIMS m/z 599 ($M^+$–H, $C_{30}H_{28}F_4N_4O_3S$).

Example 41

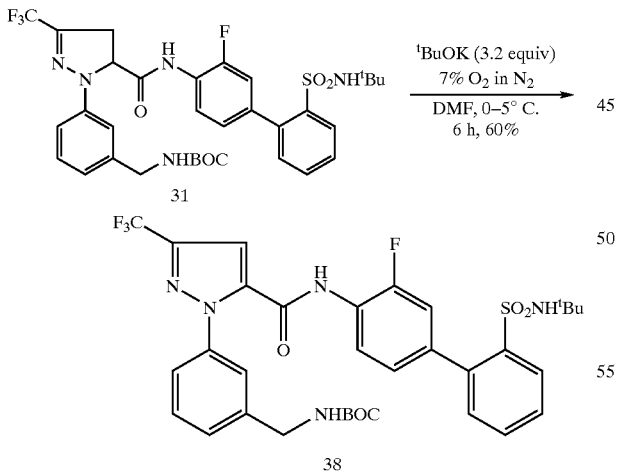

1-[3-((N-tert-Butoxy)carbonyl)aminomethyl]phenyl-5-[2-fluoro-4-(2-(N-tert-butyl-amino)sulfonyl)phenyl]phenylcarbamoyl-3-trifluoromethylpyrazole (38)

A solution of 1-[3-((N-tert-butoxy)carbonyl)aminomethyl]phenyl-5-[2-fluoro-4-(2-(N-tert-butyl-amino)sulfonyl)phenyl]phenylcarbamoyl-3-trifluoromethylpyrazoline (31, 597 mg, 0.85 mmol) in DMF (2 mL) was added dropwise to a solution of potassium tert-butoxide (305 mg, 2.72 mmol, 3.2 equiv) in DMF (2 ml) at 0–5° C. A steady stream of 7% of $O_2$ in $N_2$ was then bubbled into the reaction mixture at 0–5° C. for 6 h. When HPLC and TLC showed the reaction was deemed complete, the reaction mixture was treated with 1.0 N aqueous citric acid solution (20 mL) at 0–5° C. The resulting solution was then extracted with EtOAc (3×15 mL). The combined organic extracts were washed with $H_2O$ (2×10 mL) and saturated NaCl aqueous solution (10 mL), dried over $MgSO_4$, and concentrated in vacuo. The residue was then purified by flash column chromatography ($SiO_2$, 10–20% EtOAc-hexanes gradient elution) to afford 1-[3-((N-tert-butoxy)carbonyl)aminomethyl]-phenyl-5-[2-fluoro-4-(2-(N-tert-butylamino)sulfonyl)phenyl]phenylcarbamoyl-3-trifluoromethylpyrazoline (38, 352 mg, 587 mg theoretical, 60%) as white solids. For 38: CIMS m/z 688 ($M^+$–H, $C_{33}H_{35}F_4N_5O_5S$).

Example 42

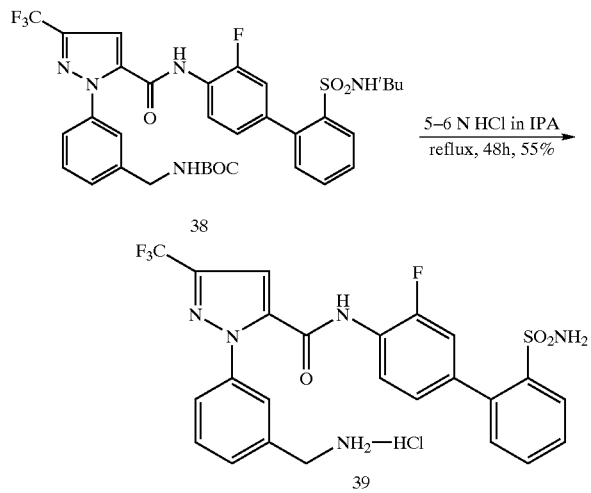

1-(aminomethyl)phenyl-5-[2-fluoro-4-(2-aminosulfonyl)-phenyl]phenylcarbamoyl-3-trifluoromethylpyrazole hydrogen chloride salt (39)

A solution of 1-[3-((N-tert-Butoxy)carbonyl)-aminomethyl]-phenyl-5-[2-fluoro-4-(2-(N-tert-butylamino)-sulfonyl)phenyl]phenylcarbamoyl-3-trifluoromethylpyrazoline (38, 128 mg, 0.2 mmol) in 5–6 N HCl in isopropyl alcohol (4 mL) was warmed up to reflux for 48 h. The solvent was removed in vacuo, and the residue was then directly recrystallized from MeOH and EtOAc to afford the desired 1-(aminomethyl)phenyl-5-[2-fluoro-4-(2-aminosulfonyl)-phenyl]phenyl-carbamoyl-3-trifluoromethylpyrazole hydrogen chloride salt (39, 57 mg, 106 mg theoretical, 55% ) as white crystals, which was found to be identical as the material obtained from totally different synthetic approach in every comparable aspect.

Example 43

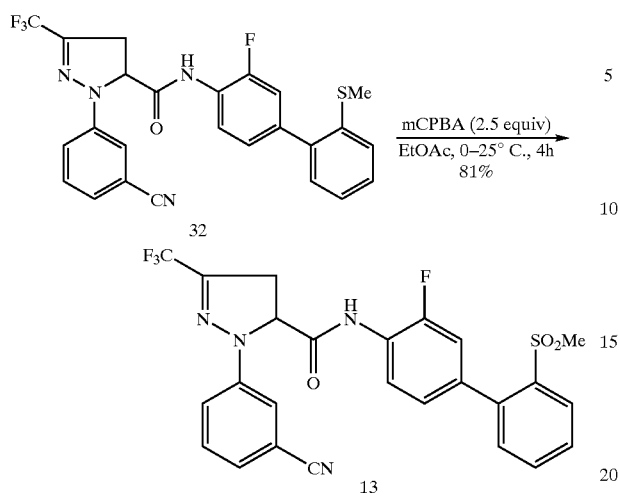

1-(3-Cyano)phenyl-5-[2-fluoro-4-(2-methylsulfonyl)phenyl]phenylcarbamoyl-3-trifluoromethylpyrazoline (13)

A suspension of 1-(3-cyano)phenyl-5-[2-fluoro-4-(2-methylthio)phenyl]phenylcarbamoyl-3-trifluoromethylpyrazoline (32, 2.49 g, 5.0 mmol) in ethyl acetate (EtOAc, 45 mL) was treated dropwise with a solution of mCPBA (57–86% pure, 3.78 g, 12.5 mmol, 2.5 equiv) in EtOAc (15 mL) at 0–5° C., and the resulting reaction mixture was stirred at 0–5° C. for 30 min before being warmed up to room temperature for 4 h. When HPLC showed the reaction was deemed complete, the reaction mixture was cooled down to 0–5° C. and treated with a saturated aqueous Na$_2$SO$_3$ solution (20 mL) and a saturated aqueous Na2CO$_2$ solution (20 mL). The resulting mixture was then gradually warmed up to room temperature and stirred at room temperature for 30 min. The two layers were separated, and the aqueous layer was extracted with EtOAc (20 mL). The combined organic extracts were washed with H$_2$O (2×20 mL) and saturated NaCl aqueous solution (20 mL), dried over MgSO$_4$, and concentrated in vacuo. The residue was purified by flash column chromatography (SiO$_2$, 10–30% EtOAc-hexanes gradient elution) to afford the desired 1-(3-cyano)phenyl-5-[2-fluoro-4-(2-methylsulfonyl)phenyl]phenylcarbamoyl-3-trifluoromethylpyrazoline (13, 2.15 g, 2.65 g theoretical, 81%) as white solids, which was found to be identical as the material obtained from the different synthetic approach detailed above in every comparable aspect.

Example 44

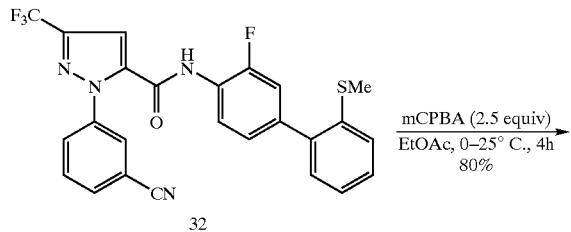

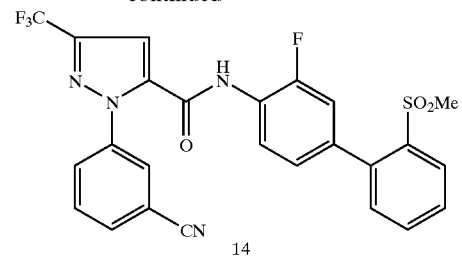

1-(3-Cyano)phenyl-5-[2-fluoro-4-(2-methylsulfonyl)phenyl]phenylcarbamoyl-3-trifluoromethylpyrazole (14)

A suspension of 1-(3-cyano)phenyl-5-[2-fluoro-4-(2-methylthio)phenyl]phenylcarbamoyl-3-trifluoromethylpyrazole (34, 2.48 g, 5.0 mmol) in ethyl acetate (EtOAc, 45 mL) was treated dropwise with a solution of mCPBA (57–86% pure, 3.78 g, 12.5 mmol, 2.5 equiv) in EtOAc (15 mL) at 0–5° C., and the resulting reaction mixture was stirred at 0–5° C. for 30 min before being warmed up to room temperature for 4 h. When HPLC showed the reaction was deemed complete, the reaction mixture was cooled down to 0–5° C. and treated with a saturated aqueous Na$_2$SO$_3$ solution (20 mL) and a saturated aqueous Na$_2$CO$_3$ solution (20 mL). The resulting mixture was then gradually warmed up to room temperature and stirred at room temperature for 30 min. The two layers were separated, and the aqueous layer was extracted with EtOAc (20 mL). The combined organic extracts were washed with H$_2$O (2×20 mL) and saturated aqueous NaCl solution (20 mL), dried over MgSO$_4$, and concentrated in vacuo. The residual slurry of the crude product in ethyl acetate (20 mL) was titrated with heptanes (50 mL) at room temperature for 30 min before the mixture was cooled down to 0–5° C. for 1 h. The solids were collected by filtration, washed with heptanes (2×20 mL), and dried at 40–45° C. in vacuo for 12 h to afford the crude desired 1-(3-cyano)phenyl-5-[2-fluoro-4-(2-methylsulfonyl)phenyl]phenylcarbamoyl-3-trifluoromethylpyrazole (14, 2.10 g, 2.64 g theoretical, 80%) as white solids, which was found to be identical as the material obtained from the different synthetic approach detailed above in every comparable aspect.

Example 45

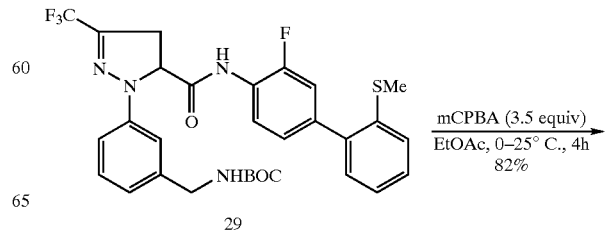

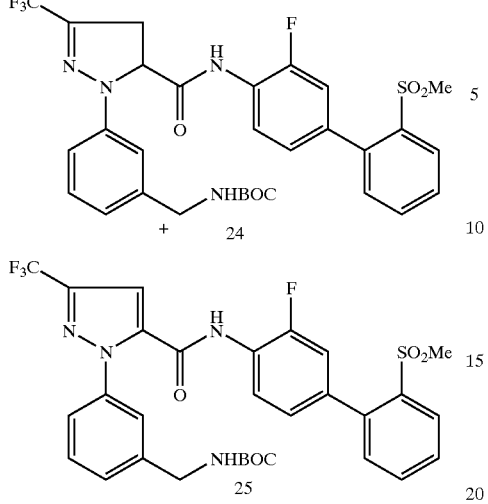

1-[3-((N-tert-Butoxy)carbonyl)aminomethyl]phenyl-5-[2-fluoro-4-(2-methyl-sulfonyl)phenyl] phenylcarbamoyl-3-trifluoromethylpyrazoline (24) and 1-[3-((N-tert-Butoxy)carbonyl)aminomethyl] phenyl-5-[2-fluoro-4-(2-methylsulfonyl)phenyl]-phenylcarbamoyl-3-trifluoromethylpyrazole (25)

A suspension of 1-[3-((N-tert-butoxy)carbonyl) aminomethyl]phenyl-5-[2-fluoro-4-(2-methylthio)phenyl] phenyl-carbamoyl-3-trifluoromethylpyrazoline (29, 1.204 g, 2.0 mmol) in ethyl acetate (EtOAc, 15 mL) was treated dropwise with a solution of mCPBA (57–86% pure, 1.513 g, 5.0 mmol, 2.5 equiv) in EtOAc (5 mL) at 0–5° C., and the resulting reaction mixture was stirred at 0–5° C. for 30 min before being warmed to room temperature for 2 h. When HPLC and TLC showed the starting material 29 was totally consumed, the reaction was found to produce a mixture of the four compounds. The reaction mixture was subsequently cooled down to 0–5° C. and treated with one additional equivalent of mCPBA (605 mg), and the resulting reaction mixture was stirred at room temperature for an additional 2 h. The HPLC showed that the reaction produced a mixture of 24 and 25 in a ratio of 4 to 5. Therefore, the reaction mixture was treated with a saturated aqueous $Na_2SO_3$ solution (10 mL) and a saturated aqueous $Na_2CO_3$ solution (20 mL) at 0–5° C. The resulting mixture was then gradually warmed up to room temperature and stirred at room temperature for 30 min. The two layers were separated, and the aqueous layer was extracted with EtOAc (20 mL). The combined organic extracts were washed with $H_2O$ (2×20 mL) and saturated NaCl aqueous solution (20 mL), dried over $MgSO_4$, and concentrated in vacuo. The residue was purified by flash column chromatography ($SiO_2$, 5–25% EtOAc-hexanes gradient elution) to afford 1-[3-((N-tert-butoxy)carbonyl)amino-methyl]phenyl-5-[2-fluoro-4-(2-methyl-sulfonyl)phenyl]-phenylcarbamoyl-3-trifluoro-methylpyrazoline (24, 362 mg, 1.268 g theoretical, 28.6%) as white solids and 1-[3-((N-tert-butoxy)carbonyl) aminomethyl]phenyl-5-[2-fluoro-4-(2-methylsulfonyl) phenyl]-phenylcarbamoyl-3-trifluoromethyl-pyrazole(25, 440 mg, 1.264 g theoretical, 34.8%) as white solids. Both compounds 24 and 25 were found to be identical as the materials obtained from the different synthetic approach detailed above in every comparable aspect.

Example 46

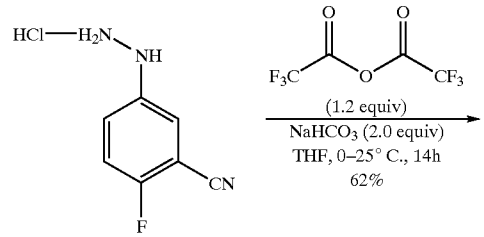

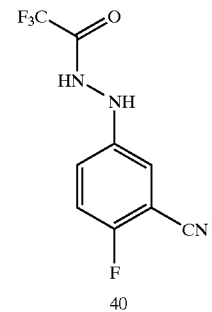

1-(4-Fluoro-3-cyano)phenyl-2-(trifluroacetyl) hydrazine (40)

A suspension of 4-fluoro-3-cyanophenylhydrazine hydrogen chloride salt (37.5 g, 0.2 mol) in THF (200 mL) was treated with solid $NaHCO_3$ (33.6 g, 0.4 mol, 2.0 equiv) at 0° C. under $N_2$, and the resulting reaction mixture was stirred at 0–50° C. for 30 min before being treated dropwise with trifluoroacetic acid anhydride (TFAA, 50.40 g, 33.9 mL, 0.24 mol, 1.2 eqiuv) at 0° C. under $N_2$. The reaction mixture was then warmed to 25° C for 12 h before being filtrated. The solvent of the filtrates were removed in vacuo, and the residue was added EtOAc (50 mL) and heptanes (30 mL), and the resulting mixture was stirred at room temperature for 15 min. The off-white solids were collected by filtration, washed with 30% EtOAc-heptanes, and dried at 40–45° C. in vacuo for 12 h to afford the crude desired 1-(4-fluoro-3-cyano)phenyl-2-(trifluroacetyl)hydrazine (40, 16.9 g, 49.4 g theoretical, 34.2%), which was found to be pure enough to do the following reaction without further purification. The filtrates were then evaporated in vacuo, and the residue was purified by flash column chromatography ($SiO_2$, 10–40% EtOAc-heptanes gradient elution) to afford an additional batch of 1-(4-fluoro-3-cyano)phenyl-2-(trifluroacetyl) hydrazine (40, 13.6 g, 49.4 g theoretical, 27.5%; total 61.7% yield) as pale-yellow solids. The analytically pure product (40) was obtained by recrystalization of crude product obtained above from EtOAc-heptanes. For 40: CIMS m/z 246 ( $M^+$–H, $C_9H_5F_4N_3O$).

Example 47

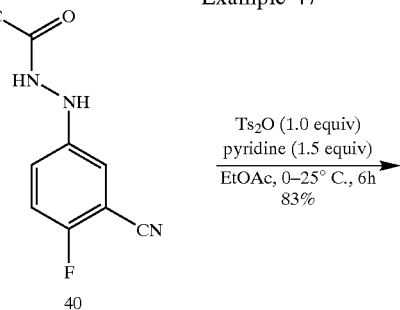

-continued

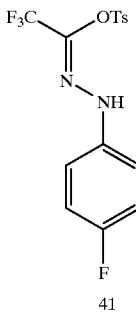

41

2,2,2-Trifluoro-N-(4-fluoro-3-cyano)phenylethanehydrazonyl tosylate (41)

A solution of 1-(4-fluoro-3-cyano)phenyl-2-(trifluoroacetyl)hydrazine (40, 12.35 g, 50 mmol) in ethyl acetate (100 mL) was treated with p-toluenesulfonyl anhydride (97% pure, 17.67 g, 52.5 mmol, 1.05 equiv) at 0° C. under $N_2$, and the resulting mixture was treated dropwise with pyridine (5.93 g, 6.1 mL, 75 mmol, 1.5 equiv) at 0 ° C. under $N_2$. The reaction mixture was then gradually warmed up to room temperature for 6 h. When HPLC and TLC showed the reaction was deemed complete, the reaction mixture was treated with water (100 mL) and EtOAc (100 mL). The two layers were separated, and the aqueous layer was extracted with EtOAc (50 mL). The combined organic extracts were washed with water (2×50 mL) and saturated NaCl aqueous solution (50 mL), dried over $MgSO_4$, and concentrated in vacuo. The crude desired product was directly recrystallized from 25% tert-butyl methyl ether (TBME)/heptanes (1:4 v/v) to afford the desired 2,2,2-trifluoro-N-(4-fluoro-3-cyano)phenylethanehydrazonyl tosylate (41, 16.64 g, 20.05 g theoretical, 83%) as pale-yellow solids, which was found to be essentially pure to do the following cycloaddition reaction without further purification. For 41, CIMS m/z 400 ($M^+$–H, $C_{16}H_{11}F_4N_3O_3S$).

Example 48

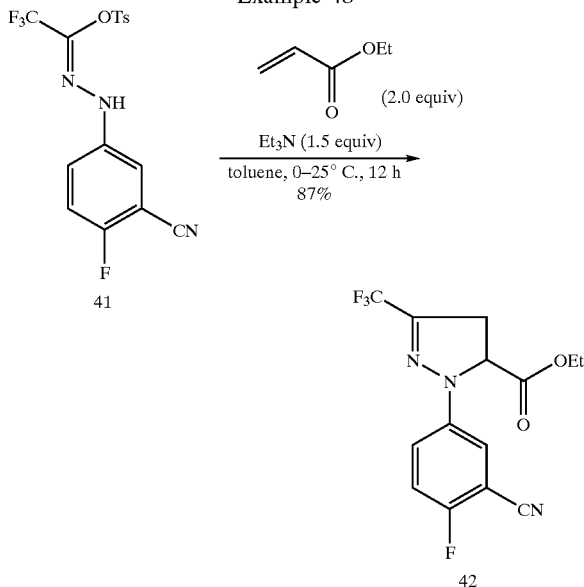

Ethyl 1-(4-fluoro-3-cyano)phenyl-3-trifluoromethylpyrazoline-5-carboxylate (42)

A suspension of 2,2,2-trifluoro-N-(4-fluoro-3-cyano)phenylethanehydrazonyl tosylate (41, 802 mg, 2.0 mmol) in toluene (8 mL) was treated ethyl acrylate (400 mg, 433 μL, 4.0 mmol, 2.0 equiv) at 0–5° C. under $N_2$, and resulting mixture was added dropwise triethylamine (303 mg, 433 μL, 3.0 mmol, 1.5 equiv) at 0–5° C. under $N_2$. The resulting reaction mixture was then stirred at 0–5° C. for 1 h before being gradually warmed up to 25° C. for 12 h. When HPLC and TLC showed that the reaction was deemed complete, the reaction mixture was directly purified by flash column chromatography ($SiO_2$, 0–20% EtOAc-hexanes gradient elution) to afford the desired ethyl 1-(4-fluoro-3-cyano)phenyl-3-trifluoromethylpyrazoline-5-carboxylate (42, 572 mg, 658 mg theoretical, 87%) as pale-yellow oil, which solidified upon standing at room temperature in vacuo. For 42: CIMS m/z 330 ($M^+$+H, $C_{14}H_{11}F_4N_3O_2$); CIMS m/z 328 ($M^+$–H, $C_{14}H_{11}F_4N_3O_2$).

Example 49

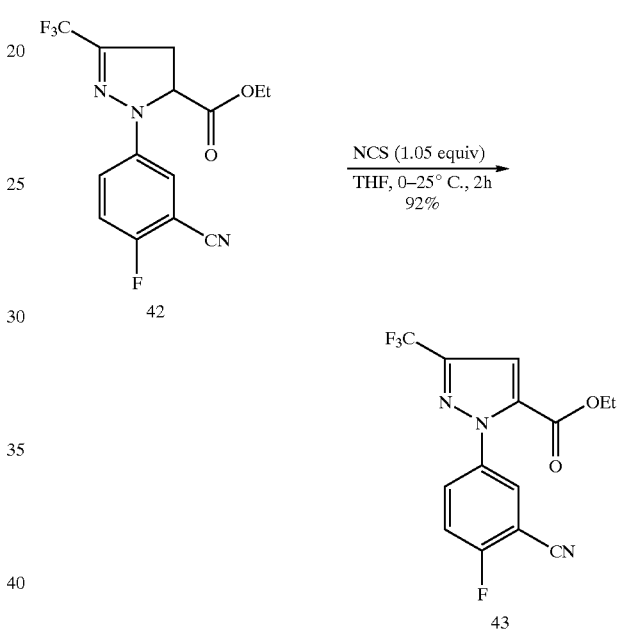

Ethyl 1-(4-fluoro-3-cyano)phenyl-3-trifluoromethylpyrazole-5-carboxylate (43)

A solution of ethyl 1-(4-fluoro-3-cyano)phenyl-3-trifluoromethylpyrazoline-5-carboxylate (42, 395 mg, 1.2 mmol) in THF (4.0 mL) was treated with N-chlorosucinimide (NCS, 168 mg, 1.26 mmol, 1.05 equiv) at 0–5° C. under $N_2$, and the resulting reaction mixture was stirred at 0–5° C. for 10 min before being gradually warmed up to 25° C. for 2 h. When TLC and HPLC showed that the reaction was deemed complete, the solvent was removed in vacuo, and the residue was treated with $H_2O$ (10 mL) and EtOAc (20 mL). The two layers were separated, and the aqueous layer was extracted with EtOAc (10 mL). The combined organic extracts were washed with $H_2O$ (2×10 mL), and saturated NaCl aqueous solution (10 mL), dried over $MgSO_4$, and concentrated in vacuo. The residue was then purified by flash column chromatography ($SiO_2$, 10–25% EtOAc-hexanes gradient elution) to afford the desired ethyl 1-(4-fluoro-3-cyano)phenyl-3-trifluoromethylpyrazole-5-carboxylate (43, 361 mg, 392 mg theoretical, 92%) as off-white solids. For 43: CIMS m/z 326 ($M^+$–H, $C_{14}H_9F_4N_3O_2$).

Example 50

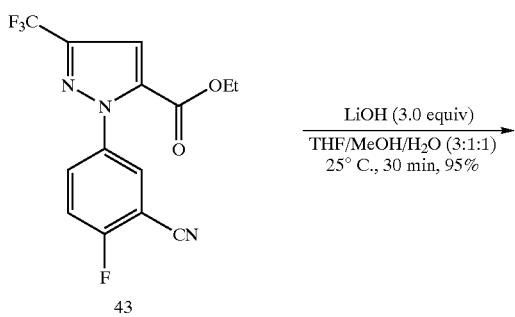

1-(4-Fluoro-3-cyano)phenyl-3-trifluoromethylpyrazole-5-carboxylic acid (44)

A solution of ethyl 1-(4-fluoro-3-cyano)phenyl-3-trifluoromethylpyrazole-5-carboxylate (43, 160 mg, 0.49 mmol) in THF—MeOH—-H$_2$O (3:1:1 v/v, 3 mL) was treated with lithium hydroxide monohydrate (LiOH—H$_2$O, 62 mg, 1.47 mmol, 3.0 equiv) at 25° C. under N$_2$, and the resulting reaction mixture was stirred at 25° C. for 30 min. When HPLC and TLC showed the hydrolysis reaction was deemed complete, the solvents was removed in vacuo. The residue was then treated with H$_2$O (10 mL) and EtOAc (5 mL). The two layers were separated, and the aqueous layer was extracted with EtOAc (5 mL). The combined organic extracts were discarded. The aqueous layer was then acidified with 2 N HCl aqueous solution to pH 3.0 before being extracted with EtOAc (2×15 mL). The combined organic extracts were then washed with H$_2$O (2×5 mL) and saturated aqueous NaCl solution (5 mL), dried over MgSO$_4$, and concentrated in vacuo. The crude 1-(4-fluoro-3-cyano)phenyl-3-trifluoromethylpyrazole-5-carboxylic acid (44, 139 mg, 147 mg theoretical, 95%) was obtained as white solids, which was found to be essentially pure to do the following reaction without further purification and to be identical with the material obtained from another totally different synthetic approach in every comparable aspect. For 44: CIMS m/z 298 (M$^+$−H, C$_{12}$H$_5$F$_4$N$_3$O$_2$).

Example 51

N-(2-Fluoro-4-iodo)phenyl acrylamide (46)

A solution of 2-fluoro-4-iodoaniline (45, 11.85 g, 0.05 mol) in EtOAc (80 mL) was treated with acryloyl chloride (6.8 g, 6.1 mL, 0.075 mol, 1.5 equiv) at 0–5° C. under N$_2$, and the resulting mixture was treated dropwise with a solution of N-methylmorpholine (NMM, 12.6 g, 13.7 mL, 0.125 mmol, 2.5 equiv) in EtOAc (20 mL) at 0–5° C. under N$_2$. The reaction mixture was stirred at 0–5 for 1 h before being quenched with water (100 mL) and EtOAc (50 mL). The solids precipitated from the mixture were collected by filtration, washed with water (100 mL) and TBME-hexane (1:2 v/v, 2×500 mL), and dried in vacuo at 40–45° C. for 12 h to afford the first batch of the crude desired N-(2-fluoro4-iodo)phenyl acrylamide (46, 9.14 g, 14.55 g theoretical, 62.8%) as white solids, which was found to be >99% pure by HPLC. The two layers of the filtrates were then separated, and the aqueous layer was extracted with EtOAc (50 mL). The combined organic extracts were washed with H$_2$O (100 mL) and saturated aqueous NaCl solution (100 mL), dried over MgSO$_4$, and concentrated in vacuo to afford the second batch of the crude desired N-(2-fluoro-4-iodo)phenyl acrylamide (46, 4.1 g, 14.55 g theoretical, 28.2%; total 91% yield) as off-white solids, which was also found to be pure enough to do the following reaction without further purification. The analytically pure product (46) was obtained from direct recrystallization of the crude 46 obtained above from EtOAc/heptanes. For 46: CIMS m/z 292 (M$^+$+H, C$_9$H$_7$FINO).

Example 52

5-(2-Fluoro-4-iodo)phenylcarbamoyl-1-(4-fluoro-3-cyano)phenyl-3-trifluoromethyl-pyrazoline (47)

A suspension of 2,2,2-trifluoro-N-(4-fluoro-3-cyano)phenylethane-hydrazonyl tosylate (41, 5.29 g, 13.2 mmol) in ethyl acetate (80 mL) was treated with N-(2-fluoro-4-iodo) phenyl acrylamide (46, 3.492 g, 12.0 mmol, 0.91 equiv) at room temperature under $N_2$, and the resulting reaction mixture was cooled down to 0–5° C. before being treated with N-methylmorpholine (NMM, 3.3 g, 3.6 mL, 30.0 mmol, 2.5 equiv) at 0–5° C. under $N_2$. The reaction mixture was stirred at 0–5° C. for 30 min before being gradually warmed up to room temperature for 1 h. The clear solution was then warmed up to 55° C. for an additional 4 h. When HPLC and TLC showed that the reaction was deemed complete, the reaction mixture was cooled down to room temperature before being treated with $H_2O$ (50 mL). The mixture was stirred at room temperature for 30 min. The precipitates were collected by filtration, washed with $H_2O$ (2×30 mL) and EtOAc/hexanes (1:1 v/v, 2×20 mL), dried at 40–45° C. in vacuo for 12 h to afford the crude desired 5-(2-fluoro-4-iodo)phenylcarbamoyl-1-(4-fluoro-3-cyano) phenyl-3-trifluoromethyl-pyrazoline (47, 2.6 g, 6.24 g theoretical, 41.7%) as white powder. The two layers of the filtrates were then separated, and the aqueous layer was extracted with EtOAc (50 mL). The combined organic extracts were washed with $H_2O$ (2×50 mL) and saturated NaCl aqueous solution (50 mL), dried over $MgSO_4$, and concentrated in vacuo. The residual slurry of the crude product (47) in EtOAc (20 mL) was the titrated with heptanes (100 ml), and the resulting mixture was stirred at room temperature for 30 min. The precipitates were then collected by filtration, washed with heptanes (2×20 mL), dried at 40–45° C. in vacuo for 12 h to afford the second batch of the crude desired 5-(2-fluoro-4-iodo) phenylcarbamoyl-1-(4-fluoro-3-cyano)phenyl-3-trifluoromethyl-pyrazoline (47, 2.2 g, 6.24 g theoretical, 35.3%; total 77% yield) as white powder. The crude product (47) obtained above was found to be pure enough to do the following reaction without further purification. The analytically pure product (47) was obtained from recrystalization of the crude material from EtOAc-heptanes. For 47: CIMS m/z 519 ($M^+$–H, $C_{18}H_{10}F_5IN_4O$).

Example 53

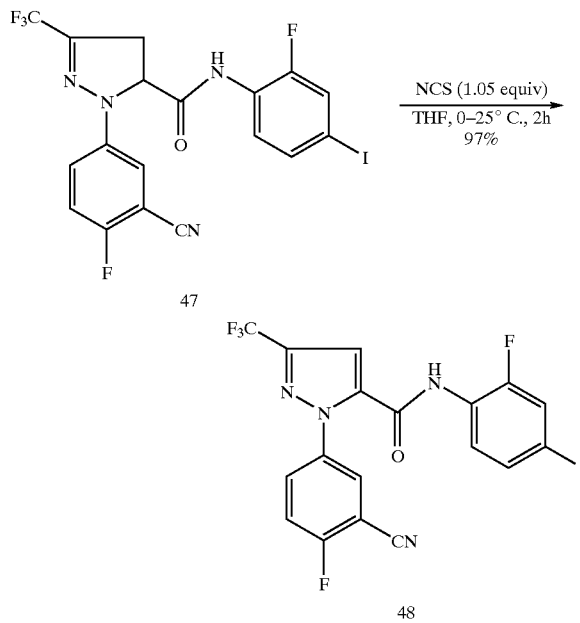

5-(2-Fluoro-4-iodo)phenylcarbamoyl-1-(4-fluoro-3-cyano)phenyl-3-trifluoromethyl-pyrazole (48)

A suspension of 5-(2-fluoro-4-iodo)phenylcarbamoyl-1-(3-cyano)phenyl-3-trifluoromethylpyrazoline (47, 3.90 g, 7.5 mmol) in THF (30 mL) was treated with N-chlorosuccinimide (NCS, 1.05 g, 7.88 mmol, 1.05 equiv) at 0–5° C., and the resulting reaction mixture was gradually warmed to room temperature for 2 h. When the HPLC and TLC showed the reaction was deemed complete, the solvent was removed in vacuo and the residue was treated with water (50 mL) and EtOAc-heptanes (1:4 v/v, 30 mL). The mixture was stirred at room temperature for 30 min, and the solids were collected by filtration, washed with EtOAc-heptanes (1:4 v/v, 2×30 mL), and dried at 40–45° C. in vacuo for 12 h to afford the crude desired 5-(2-fluoro-4-iodo) phenylcarbamoyl-1-(4-fluoro-3-cyano)phenyl-3-trifluoromethyl-pyrazole (48, 3.79 g, 3.89 g theoretical, 97.4%) as off-white powder, which was found to be >99% by HPLC and was used in the following reaction without further purification. The analytically pure product (48) was obtained from recrystallization of the crude product obtained above from EtOAc/heptanes. For 48: CIMS m/z 517 ($M^+$–H, $C_{18}H_8F_5IN_4O$).

Example 54

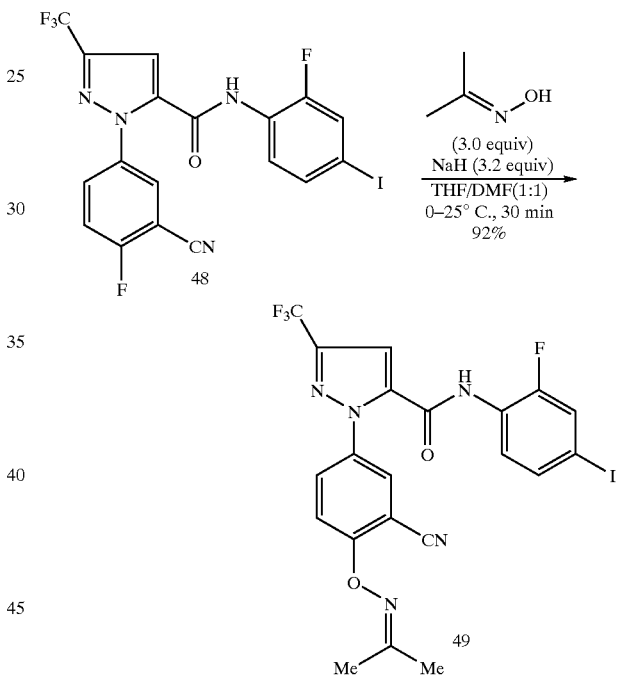

5-(2-Fluoro-4-iodo)phenylcarbamoyl-1-[3-cyano-4-(dimethylmethyleneimino)oxy]-phenyl-3-trifluoromethylpyrazole (49)

A solution of acetone oxime (657 mg, 9.0 mmol, 3.0 equiv) in anhydrous THF (4.0 mL) was added to a suspension of sodium hydride (NaH, 60% oil dispersion in mineral oil, 384 mg, 9.6 mmol, 3.2 equiv) in anhydrous THF (4.0 mL) at 0–5° C. under N2, and the resulting mixture was stirred at 0–5° C. for 30 min before being treated a solution of 5-(2-fluoro-4-iodo)phenylcarbamoyl-1-(4-fluoro-3-cyano)phenyl-3-trifluoromethyl-pyrazole (48, 1.554 g, 3.0 mmol) in anhydrous DMF (8.0 mL) at 0–5° C. under $N_2$. The resulting reaction mixture was subsequently stirred at 0–5° C. for 10 min before being gradually warmed up to 25° C. for an additional 30 min. When TLC and HPLC showed that the reaction was deemed complete, the reaction mixture was treated with $H_2O$ (50 mL), and the mixture was stirred at room temperature for 30 min. The off-white precipitates were then collected by filtration, washed with H₂O (2×10 mL) and EtOAc-heptanes (1:4 v/v, 2×20 mL), and dried at 40–45° C. in vacuo for 12 h to afford the crude desired 5-(2-fluoro-4-iodo)phenylcarbamoyl-1-[3-cyano-4-(dimethylmethyleneimino)oxy]-phenyl-3-trifluoro-methylpyrazole (49, 1.576 g, 1.713 g theoretical, 92%), Which was found to be >99% pure by HPLC and was used in the following reaction without further purification. The analytically pure product (49) was obtained by recrystallization of crude material obtained above from EtOAc-heptanes. For 49: CIMS m/z 570 (M⁺–H, $C_{22}H_{14}F_4IN_5O_2$).

Example 55

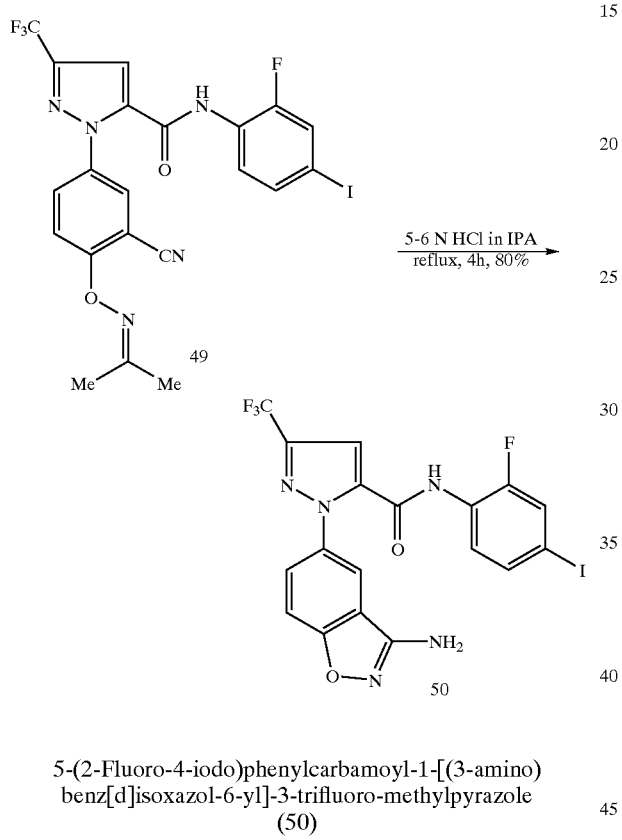

5-(2-Fluoro-4-iodo)phenylcarbamoyl-1-[(3-amino)benz[d]isoxazol-6-yl]-3-trifluoro-methylpyrazole (50)

A suspension of 5-(2-fluoro-4-iodo)phenylcarbamoyl-1-[3-cyano-4-(dimethylmethyleneimino)oxy]phenyl-3-trifluoro-methylpyrazole (49, 571 mg, 1.0 mmol) in 5–6 N HCl in isopropyl alcohol (4 mL) was warmed up to reflux for 4 h. When HPLC and TLC showed that the reaction was deemed complete, the solvent was removed in vacuo, and the residue was treated with saturated Na₂CO₃ aqueous solution (10 ml) and EtOAc (20 mL). The two layers were separated, and the aqueous layer was extracted with EtOAc (10 mL). The combined organic extracts were washed with H₂O (2×10 mL) and saturated NaCl aqueous solution (10 mL), dried over MgSO₄, and concentrated in vacuo. The residue was purified by flash column chromatography (SiO₂, 10–30% EtOAc-hexanes gradient elution) to afford the desired 5-(2-fluoro-4-iodo)phenylcarbamoyl-1-[(3-amino)benz[d]isoxazol-6-yl]-3-trifluoro-methylpyrazole (50, 427 mg, 531 mg theoretical, 80.4%) as white solids. For 50: CIMS m/z 529/531 (M⁺–H, $C_{18}H_{10}F_4IN_5O_2$).

Obviously, numerous modifications and variations of the present invention are possible in light of the above teachings. It is therefore to be understood that within the scope of the appended claims, the invention may be practiced otherwise than as specifically described herein.

What is claimed is:

1. A process for preparing a compound of formula I:

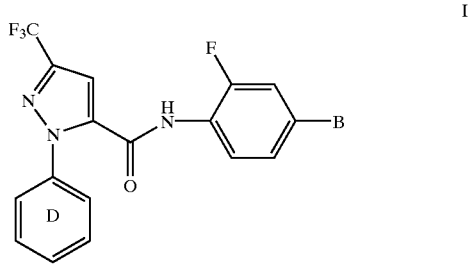

wherein ring D is 2-(aminomethyl)phenyl, 3-(aminomethyl)phenyl, or (3-amino)benz[d]isoxazol-6-yl and B is 2-MeSO₂-phenyl or 2-NH₂SO₂-phenyl, the process comprising:

(e) acylating a hydrazine of formula II to form a compound of formula III:

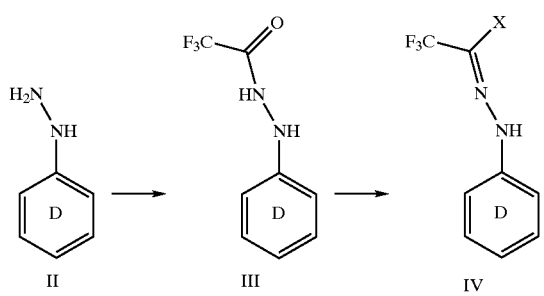

wherein ring D is selected from 2-cyanophenyl, 3-cyanophenyl, 3-cyano-4-fluorophenyl, 2-(PgNHCH₂)phenyl, and 3-(PgNHCH₂)phenyl, and Pg is an amine protecting group;

(f) converting a compound of formula III to a compound of formula IV, wherein X is selected from Cl, OMs, Br, OSO₂Ph, and OTs;

(g) contacting a compound of formula IV with a base to form a dipolar compound of formula V:

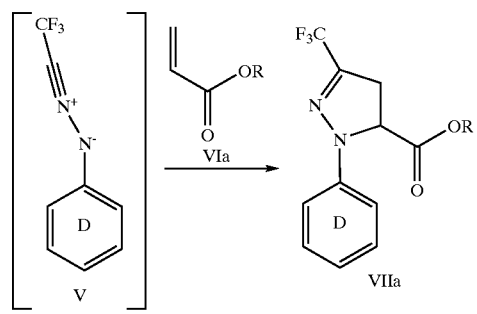

(h) contacting a compound of formula V in situ with a dipolarophile of formula VIa to form a compound of formula VIIa, wherein R is selected from H, Me, Et, and n-Pr;

(i) converting a compound of formula VIIa to a compound of formula I by subjecting it to the following reactions, which may be performed, when applicable, in any order:

(e1) oxidizing the pyrazoline to a pyrazole;
(j1) when R is other than H, hydrolyzing the compound of formula VIIa to its corresponding acid;
(j2) when R is H, contacting the acid of formula VIIa with an aniline of formula Vib to form an amide;

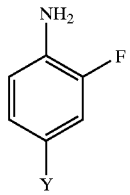

VIIb wherein Y is selected from Br, 2-MeSO$_2$-phenyl, 2-MeS-phenyl, 2-NH$_2$SO$_2$-phenyl, and 2-PgNHSO$_2$-phenyl;
(e2a') when Y=Br, converting the Br group to 2-MeS-phenyl, 2-SO$_2$Me-phenyl, or 2-SO$_2$NH$_2$-phenyl;
(e2b') when Y=2-MeS-phenyl, converting the MeS-group to MeSO$_2$—;
(e3a) when ring D is cyanophenyl, converting this group to aminomethylphenyl or (PgNHCH$_2$)phenyl;
(e3b) when ring D is 3-cyano-4-fluorophenyl, converting this ring to (3-amino)benz[d]isoxazol-6-yl; and,
(e4) when Pg is present, removing the protecting group.

2. A process according to claim 1, wherein step (b) is performed by contacting a compound of formula III with a sulfonyl chloride in the presence of an amine base to form a compound of formula IV wherein X is Cl;
wherein the sulfonyl chloride is selected from methylsulfonyl chloride, phenylsulfonyl chloride and toluenesulfonyl chloride, the amine base is selected from triethylamine, diisopropylethylamine, and N-methylmorpholine.

3. A process according to claim 2, wherein the sulfonyl chloride is phenylsulfonyl chloride the amine base is diisopropylethylamine.

4. A process according to claim 2, wherein ring D is 3-(aminomethyl)phenyl, B is 2-MeSO$_2$-phenyl, and step (i) is performed in the following order:
(e1) oxidizing the pyrazoline to a pyrazole;
(j1) when R is other than H, hydrolyzing the compound of formula VIIa to its corresponding acid;
(j2) when R is H, contacting the acid of formula VIIa with an aniline of formula VIIb to form an amide;

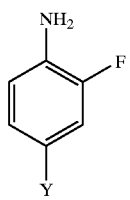

VIIb wherein Y is 2-MeS-phenyl;
(e2b') converting the MeS— group to MeSO$_2$—; and,
(e3a') converting the cyanophenyl group to 3-(aminomethyl)phenyl.

5. A process according to claim 2, wherein ring D is 3-(aminomethyl)phenyl, B is 2-MeSO$_2$-phenyl, and step (e) is performed in the following order:
(e1) oxidizing the pyrazoline to a pyrazole;
(j1) when R is other than H, hydrolyzing the compound of formula VIIa to its corresponding acid;
(j2) when R is H, contacting the acid of formula VIIa with an aniline of formula VIIb to form an amide;

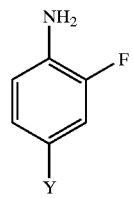

VIIb wherein Y is Br;
(e2a') converting the Br group to 2-MeS-phenyl;
(e2b') converting the MeS— group to MeSO$_2$—; and,
(e3a) converting the cyanophenyl group to 3-(aminomethyl)phenyl.

6. A process according to claim 1, wherein in (i) the compound of formula VIIa is converted to a compound of formula I by subjecting it to the following reactions, that are performed, when applicable, in the order shown:
(e1) oxidizing the pyrazoline to a pyrazole;
(j1) when R is other than H, hydrolyzing the compound of formula VIIa to its corresponding acid;
(j2) when R is H, contacting the acid of formula VIIa with an aniline of formula VIIb to form an amide;

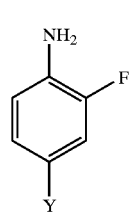

VIIb wherein Y is selected from Br, 2-MeSO$_2$-phenyl, 2-MeS-phenyl, 2-NH$_2$SO$_2$-phenyl, and 2-PgNHSO$_2$-phenyl;
(e2a') when Y=Br, converting the Br group to 2-MeS-phenyl, 2-SO$_2$Me-phenyl, or 2-SO$_2$NH$_2$-phenyl;
(e2b') when Y=2-MeS-phenyl, converting the MeS— group to MeSO$_2$—;
(e3a') when ring D is cyanophenyl, converting this group to aminomethylphenyl or (PgNHCH$_2$)phenyl;
(e3b) when ring D is 3-cyano-4-fluorophenyl, converting this ring to (3-amino)benz[d]isoxazol-6-yl; and,
(e4) when Pg is present, removing the protecting group.

7. A process according to claim 11, wherein in (i) the compound of formula VIIa is converted to a compound of formula I by subjecting it to the following reactions, that are performed, when applicable, in the order shown:
(e1) oxidizing the pyrazoline to a pyrazole;
(j1) when R is other than H, hydrolyzing the compound of formula VIIa to its corresponding acid;
(j2) when R is H, contacting the acid of formula VIIa with an aniline of formula VIIb to form an amide;

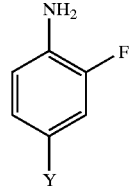

VIIb wherein Y is selected from Br, 2-MeSO$_2$-phenyl, 2-MeS-phenyl, 2-NH$_2$SO$_2$-phenyl, and 2-PgNHSO$_2$-phenyl;

(e3a) when ring D is cyanophenyl, converting this group to aminomethylphenyl or (PgNHCH$_2$)phenyl;

(e3b) when ring D is 3-cyano-4-fluorophenyl, converting this ring to (3-amino)benz[d]isoxazol-6-yl;

(e2a') when Y=Br, converting the Br group to 2-MeS-phenyl, 2-SO$_2$Me-phenyl, or 2-SO$_2$NH$_2$-phenyl;

(e2b') when Y=2-MeS-phenyl, converting the MeS— group to MeSO$_2$—; and, (e4) when Pg is present, removing the protecting group.

8. A process according to claim 1, wherein in (i) the compound of formula VIIa is converted to a compound of formula I by subjecting it to the following reactions, that are performed, when applicable, in the order shown:

(j1) when R is other than H, hydrolyzing the compound of formula VIIa to its corresponding acid;

(j2) when R is H, contacting the acid of formula VIIa with an aniline of formula VIIb to form an amide;

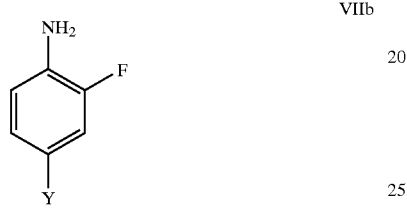

VIIb wherein Y is selected from Br, 2-MeSO$_2$-phenyl, 2-MeS-phenyl, 2-NH$_2$SO$_2$-phenyl, and 2-PgNHSO$_2$-phenyl;

(e2a') when Y=Br, converting the Br group to 2-MeS-phenyl, 2-SO$_2$Me-phenyl, or 2-SO$_2$NH$_2$-phenyl;

(e2b') when Y=2-MeS-phenyl, converting the MeS— group to MeSO$_2$—;

(e1) oxidizing the pyrazoline to a pyrazole;

(e3a) when ring D is cyanophenyl, converting this group to aminomethylphenyl or (PgNHCH$_2$)phenyl;

(e3b) when ring D is 3-cyano-4-fluorophenyl, converting this ring to (3-amino)benz[d]isoxazol-6-yl; and, (e4) when Pg is present, removing the protecting group.

9. A process according to claim 1, wherein in (i) the compound of formula VIIa is converted to a compound of formula I by subjecting it to the following reactions, that are performed, when applicable, in the order shown:

(j1) when R is other than H, hydrolyzing the compound of formula VIIa to its corresponding acid;

(j2) when R is H, contacting the acid of formula VIIa with an aniline of formula VIIb to form an amide;

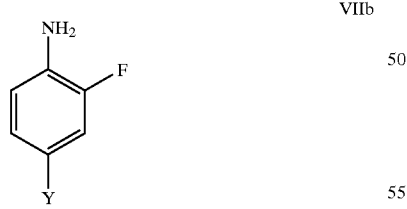

VIIb wherein Y is selected from Br, 2-MeSO$_2$-phenyl, 2-MeS-phenyl, 2-NH$_2$SO$_2$-phenyl, and 2-PgNHSO$_2$-phenyl;

(e2a') when Y=Br, converting the Br group to 2-MeS-phenyl, 2-SO$_2$Me-phenyl, or 2-SO$_2$NH$_2$-phenyl;

(e2b') when Y=2-MeS-phenyl, converting the MeS— group to MeSO$_2$—;

(e3a) when ring D is cyanophenyl, converting this group to aminomethylphenyl or (PgNHCH$_2$)phenyl;

(e3b) when ring D is 3-cyano-4-fluorophenyl, converting this ring to (3-amino)benz[d]isoxazol-6-yl;

(e1) oxidizing the pyrazoline to a pyrazole; and, (e4) when Pg is present, removing the protecting group.

10. A process according to claim 1, wherein in (i) the compound of formula VIIa is converted to a compound of formula I by subjecting it to the following reactions, that are performed, when applicable, in the order shown:

(e3a) when ring D is cyanophenyl, converting this group to aminomethylphenyl or (PgNHCH$_2$)phenyl;

(e3b) when ring D is 3-cyano-4-fluorophenyl, converting this ring to (3-amino)benz[d]isoxazol-6-yl;

(e1) oxidizing the pyrazoline to a pyrazole;

(j1) when R is other than H, hydrolyzing the compound of formula VIIa to its corresponding acid;

(j2) when R is H, contacting the acid of formula VIIa with an aniline of formula VIIb to form an amide;

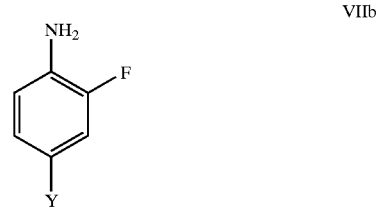

VIIb wherein Y is selected from Br, 2-MeSO$_2$-phenyl, 2-MeS-phenyl, 2-NH$_2$SO$_2$-phenyl, and 2-PgNHSO$_2$-phenyl;

(e2a') when Y=Br, converting the Br group to 2-MeS-phenyl, 2-SO$_2$Me-phenyl, or 2-SO$_2$NH$_2$-phenyl;

(e2b') when Y=2-MeS-phenyl, converting the MeS— group to MeSO$_2$—; and, (e4) when Pg is present, removing the protecting group.

11. A process according to claim 1, wherein in (i) the compound of formula VIIa is converted to a compound of formula I by subjecting it to the following reactions, that are performed, when applicable, in the order shown:

(e3a) when ring D is cyanophenyl, converting this group to aminomethylphenyl or (PgNHCH$_2$)phenyl;

(e3b) when ring D is 3-cyano-4-fluorophenyl, converting this ring to (3-amino)benz[d]isoxazol-6-yl;

(j1) when R is other than H, hydrolyzing the compound of formula VIIa to its corresponding acid;

(j2) when R is H, contacting the acid of formula VIIa with an aniline of formula VIIb to form an amide;

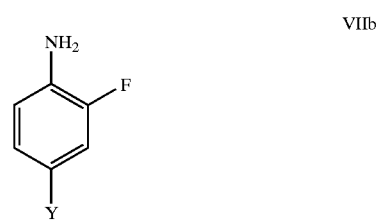

VIIb wherein Y is selected from Br, 2-MeSO$_2$-phenyl, 2-MeS-phenyl, 2-NH$_2$SO$_2$-phenyl, and 2-PgNHSO$_2$-phenyl;

(e2a') when Y=Br, converting the Br group to 2-MeS-phenyl, 2-SO$_2$Me-phenyl, or 2-SO$_2$NH$_2$-phenyl;

(e2b') when Y=2-MeS-phenyl, converting the MeS— group to MeSO$_2$—;

(e1) oxidizing the pyrazoline to a pyrazole; and, (e4) when Pg is present, removing the protecting group.

12. A compound of formula X:

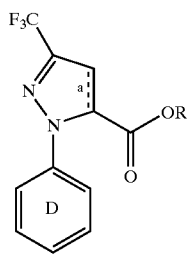

X wherein R is selected from H, Me, Et, and n-Pr;

ring D is 2-cyanophenyl, 2-(PgNHCH$_2$)phenyl, 2-(aminomethyl)phenyl, 3-cyanophenyl, 3-(PgNHCH$_2$)phenyl, 3-(aminomethyl)phenyl, 3-cyano-4-fluorophenyl, and (3-amino)benz[d]isoxazol-6-yl;

bond a is absent or is a single bond; and,

Pg is an amine protecting group selected from Boc and TFA.

13. A compound according to claim 12, wherein R is H.
14. A compound according to claim 12, wherein R is Me.
15. A compound according to claim 12, wherein R is Et.
16. A compound according to claim 12, wherein R is n-Pr.
17. A compound according to claim 12, wherein R is H and D is 3-cyanophenyl.
18. A compound according to claim 12, wherein R is Et and D is 3-cyanophenyl.
19. A compound according to claim 12, wherein R is Et and D is 3-(PgNHCH$_2$)phenyl.
20. A compound according to claim 12, wherein R is Et and D is 3-cyano-4-fluorophenyl.

* * * * *